United States Patent
Barnett et al.

(10) Patent No.: US 8,247,377 B2
(45) Date of Patent: Aug. 21, 2012

(54) NON-STEROIDAL GLUCOCORTICOID INHIBITORS AND THEIR USE IN TREATING INFLAMMATION, ALLERGY AND AUTO-IMMUNE CONDITIONS

(75) Inventors: Heather Anne Barnett, Stevenage (GB); Ian Baxter Campbell, Stevenage (GB); Diane Mary Coe, Stevenage (GB); Anthony William James Cooper, Stevenage (GB); Graham George Adam Inglis, Stevenage (GB); Haydn Terence Jones, Stevenage (GB); Steven Philip Keeling, Stevenage (GB); Simon John Fawcett MacDonald, Stevenage (GB); Iain McFarlane McLay, Stevenage (GB); Philip Alan Skone, Stevenage (GB); Gordon Gad Weingarten, Stevenage (GB); James Michael Woolven, Stevenage (GB)

(73) Assignee: Glaxo Group Limited, Middlesex (GB)

( * ) Notice: Subject to any disclaimer, the term of this patent is extended or adjusted under 35 U.S.C. 154(b) by 726 days.

(21) Appl. No.: 12/303,791

(22) PCT Filed: Jun. 11, 2007

(86) PCT No.: PCT/EP2007/055724
§ 371 (c)(1),
(2), (4) Date: Dec. 8, 2008

(87) PCT Pub. No.: WO2007/144327
PCT Pub. Date: Dec. 21, 2007

(65) Prior Publication Data
US 2010/0234441 A1   Sep. 16, 2010

(30) Foreign Application Priority Data

Jun. 12, 2006   (GB) .................................. 0611587.7
Dec. 20, 2006   (GB) .................................. 0625457.7
May 29, 2007   (GB) .................................. 0710217.1

(51) Int. Cl.
*A61K 31/44*   (2006.01)
*A61K 31/40*   (2006.01)
*A61P 23/00*   (2006.01)

(52) U.S. Cl. ........................ 514/18.3; 514/283; 514/424
(58) Field of Classification Search ................... None
See application file for complete search history.

(56) References Cited

FOREIGN PATENT DOCUMENTS

| WO | 0032584 A | 6/2000 |
|---|---|---|
| WO | 03037352 A | 5/2003 |
| WO | 2004071389 A | 8/2004 |
| WO | 2005030213 A | 4/2005 |
| WO | 2007000334 A | 1/2007 |

OTHER PUBLICATIONS

Vippagunta (Adv. Drug Deliv. Rev, 48: 3-26, 2001).*
Betageri, et al., "Trifluoromethyl group as a pharmacophore: Effect of replacing a CF3 group on binding and agonist activity of a glucocorticoid receptor ligand" Bioorganic & Medicinal Chemistry Letters, vol. 15(21), 2005, pp. 4761-4769.

* cited by examiner

*Primary Examiner* — Brandon Fetterolf
*Assistant Examiner* — Anna Pagonakis
(74) *Attorney, Agent, or Firm* — Nora L. Stein; Theodore R. Furman

(57) ABSTRACT

The present invention provides compounds of formula (I):

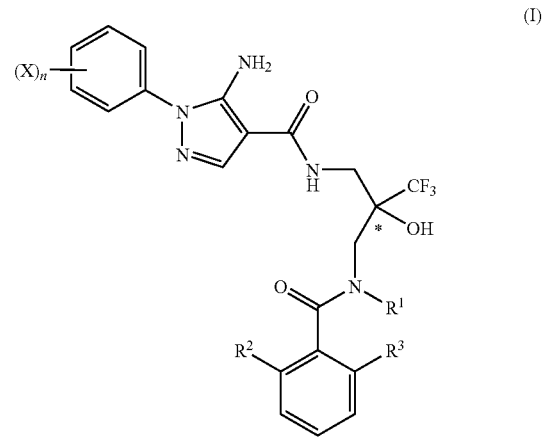

* = chiral centre a process for their preparation, to pharmaceutical compositions comprising the compounds and the preparation of said compositions, to intermediates and to use of the compounds for the manufacture of a medicament for therapeutic treatment, particularly for the treatment of inflammation, allergy and/or autoimmune conditions.

21 Claims, No Drawings

NON-STEROIDAL GLUCOCORTICOID INHIBITORS AND THEIR USE IN TREATING INFLAMMATION, ALLERGY AND AUTO-IMMUNE CONDITIONS

CROSS-REFERENCE TO RELATED APPLICATIONS

This application is filed pursuant to 35 USC 371 as a United States National Phase Application of International Patent Application Serial No. PCT/EP2007/055724 filed on 11 Jun. 2007, which claims priority from GB 0611587.7 filed 12 Jun. 2006, GB 0625457.7 filed 20 Dec. 2006, and GB 0710217.1 filed 29 May 2007 in the United Kingdom.

The present invention relates to non-steroidal glucocorticoid receptor binding compounds and a process for their preparation, to pharmaceutical compositions comprising the compounds and the preparation of said compositions, to intermediates and to use of the compounds for the manufacture of a medicament for therapeutic treatment, particularly for the treatment of inflammation, allergy and/or auto-immune conditions.

Nuclear receptors are a class of structurally related proteins involved in the regulation of gene expression. The steroid hormone receptors are a subset of this family whose natural ligands typically comprise endogenous steroids such as estradiol (estrogen receptor), progesterone (progesterone receptor) and cortisol (glucocorticoid receptor). Man-made ligands to these receptors play an important role in human health, in particular the use of glucocorticoid agonists to treat a wide range of inflammatory conditions.

Glucocorticoids exert their actions at the glucocorticoid receptor (GR) through at least two intracellular mechanisms, transactivation and transrepression (see: Schacke, H., Docke, W-D. & Asadullah, K. (2002) *Pharmacol and Therapeutics* 96:23-43; Ray, A., Siegel, M. D., Prefontaine, K. E. & Ray, P. (1995) *Chest* 107:139 S; and Konig, H., Ponta, H., Rahmsdorf, H. J. & Herrlich, P. (1992) *EMBO J.* 11:2241-2246). Transactivation involves direct binding of the glucocorticoid receptor to distinct deoxyribonucleic acid (DNA) glucocorticoid response elements (GREs) within gene promoters, usually but not always increasing the transcription of the downstream gene product. Recently, it has been shown that the GR can also regulate gene expression through an additional pathway (transrepression) in which the GR does not bind directly to DNA. This mechanism involves interaction of the GR with other transcription factors, in particular NFkB and AP1, leading to inhibition of their pro-transcriptional activity (Schacke, H., Docke, W-D. & Asadullah, K. (2002) *Pharmacol and Therapeutics* 96:23-43; and Ray, A., Siegel, M. D., Prefontaine, K. E. & Ray, P. (1995) *Chest* 107:139 S). Many of the genes involved in the inflammatory response are transcriptionally activated through the NFkB and AP1 pathways and therefore inhibition of this pathway by glucocorticoids may explain their anti-inflammatory effect (see: Barnes, P. J. & Adcock, I. (1993) *Trend Pharmacol Sci* 14: 436-441; and Cato, A. C. & Wade, E. (1996) *Bioessays* 18: 371-378).

Despite the effectiveness of glucocorticoids in treating a wide range of conditions, a number of side-effects are associated with pathological increases in endogenous cortisol or the use of exogenous, and particularly systemically administered, glucocorticoids. These include reduction in bone mineral density (Wong, C. A., Walsh, L. J., Smith, C. J. et al. (2000) *Lancet* 355:1399-1403), slowing of growth (Allen, D. B. (2000) Allergy 55: suppl 62, 15-18), skin bruising (Pauwels, R. A., Lofdahl, C. G., Latinen, L. A. et al. (1999) *N Engl J Med* 340:1948-1953), development of cataracts (Cumming, R. G., Mitchell, P. & Leeder, S. R. (1997) *N Engl J Med* 337:8-14) and dysregulation of lipid and glucose metabolism (Faul, J. L., Tormey, W., Tormey, V. & Burke, C. (1998) *BMJ* 317:1491; and Andrews, R. C. & Walker, B. R. (1999) *Clin Sci* 96:513-523). The side-effects are serious enough often to limit the dose of glucocorticoid that can be used to treat the underlying pathology leading to reduced efficacy of treatment.

It has been suggested that excessive activation of the transactivation-GRE pathway may mediate some of these side-effects (see Schacke, H., Docke, W-D. & Asadullah, K. (2002) *Pharmacol and Therapeutics* 96:23-43). Development of glucocorticoids that selectively modulate the transrepression pathway compared with the transactivation pathway may therefore have a superior anti-inflammatory to side-effect therapeutic index, allowing more effective and safer treatment of the patient. This new class of glucocorticoids could be used to treat more effectively and more safely the whole spectrum of disease currently treated by current glucocorticoids.

Current known glucocorticoids have proved useful in the treatment of inflammation, tissue rejection, auto-immunity, various malignancies, such as leukemias and lymphomas, Cushing's syndrome, rheumatic fever, polyarteritis nodosa, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, hypercalcemia, hypergylcemia, acute adrenal insufficiency, chronic primary adrenal insufficiency, secondary adrenal insufficiency, congenital adrenal hyperplasia, cerebral edema, thrombocytopenia, Little's syndrome, inflammatory scalp alopecia, panniculitis, psoriasis, discoid lupus erythemnatosus, inflamed cysts, atopic dermatitis, pyoderma gangrenosum, pemphigus vulgaris, bullous pemphigoid, dermatomyositis, herpes gestationis, eosinophilic fasciitis, relapsing polychondritis, inflammatory vasculitis, sarcoidosis, Sweet's disease, type 1 reactive leprosy, capillary hemangiomas, contact dermatitis, atopic dermatitis, lichen planus, exfoliative dermatitis, erythema nodosum, acne, hirsutism, toxic epidermal necrolysis, erythema multiform and cutaneous T-cell lymphoma.

Glucocorticoids are especially useful in disease states involving systemic inflammation such as inflammatory bowel disease, polyarteritis nodosa, Wegener's granulomatosis, giant cell arteritis, rheumatoid arthritis, osteoarthritis, seasonal rhinitis, allergic rhinitis, vasomotor rhinitis, urticaria, angioneurotic edema, chronic obstructive pulmonary disease, asthma, tendonitis, bursitis, Crohn's disease, ulcerative colitis, autoimmune chronic active hepatitis, organ transplantation, hepatitis and cirrhosis. Glucocorticoids have also been used as immunostimulants and repressors and as wound healing and tissue repair agents.

A number of conditions where a key component of the pathology is inflammation within the central nervous system (CNS) are currently treated with high doses of glucocorticoid agents. It is understood that these high doses are required primarily because the steroidal agents are actively removed from the brain by specific transporters, and therefore high systemic concentrations must be achieved in order to reach therapeutic doses within the CNS. Agents which showed a higher propensity to partition into the brain would allow these therapeutic concentrations to be achieved within the CNS with a significant reduction in the systemic glucocorticoid burden, resulting in an reduced risk from the known systemic effects of glucocorticoids (such as osteoporosis, diabetes, myopathy, skin thinning and weight gain).

Inflammatory or auto-immune conditions of the nervous system where such an approach may prove valuable include but are not limited to multiple sclerosis, cerebral vasculitis, neurosarcoidosis, Sjogren's syndrome, systemic lupus erythematosis, acute or chronic inflammatory polyradiculopathy, Alzheimer's disease, neoplastic diseases of the nervous system including meningioma, lymphoma and malignant meningitis, and trauma and infectious diseases of the nervous system such as tuberculosis. Other conditions include spinal cord injury and brain injury, for example post-infarction (stroke).

There remains a need to find further compounds which bind to the glucocorticoid receptor.

In one embodiment, the present invention provides compounds of formula (I):

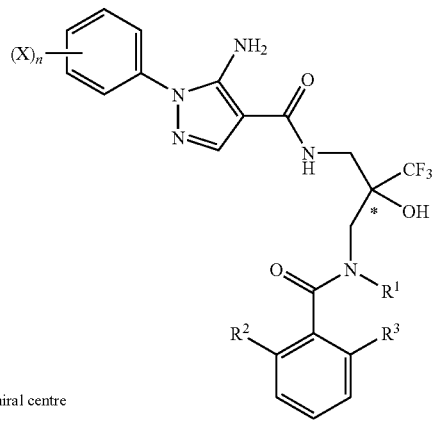

(I)

* = chiral centre wherein
$R^1$ is selected from hydrogen, methyl, ethyl and 2-fluoroethyl;
$R^2$ and $R^3$ are each independently selected from bromine, chlorine, fluorine, —$CHF_2$, —$CF_3$ and —$OCHF_2$, or $R^2$ is —$SO_2CH_3$ and $R^3$ is hydrogen;
n is an integer selected from 0, 1 and 2,
when n is 1, X is selected from chlorine and fluorine, and when n is 2, each X is fluorine;
and salts and solvates thereof (hereinafter "compounds of the invention").

In a further embodiment, the present invention provides compounds of formula (IA):

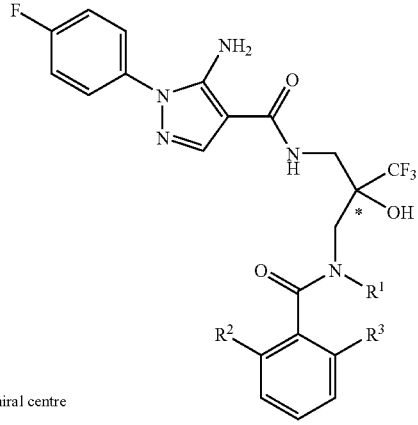

(IA)

* = chiral centre wherein
$R^1$ is selected from hydrogen, methyl and ethyl; and
when $R^1$ is hydrogen or methyl, $R^2$ and $R^3$ are each independently selected from chlorine and fluorine, or
when $R^1$ is ethyl, $R^2$ and $R^3$ are each independently selected from chlorine and fluorine, or
$R^2$ is —$SO_2CH_3$ and $R^3$ is hydrogen;
and salts and solvates thereof.

The compounds of formula (I) each contain a chiral centre and there are two possible enantiomers of each compound of formula (I).

The terms Enantiomer 1 and Enantiomer 2 are used herein to refer to the enantiomers of a compound of formula (I), based on the order of their elution using the chiral chromatography methodology described herein. Enantiomer 1 refers to the first enantiomer to elute, and Enantiomer 2 refers to the second enantiomer to elute.

It will be appreciated by those skilled in the art that although the absolute retention time on chromatography can be variable, the order of elution remains the same when the same column and conditions are employed. However, the use of a different chromatography column and conditions may alter the order of elution.

It will be appreciated by those skilled in the art that at least one isomer (e.g. one enantiomer of the racemate) has the described activity. The other isomers may have similar activity, less activity, no activity or may have some antagonist activity in a functional assay.

A mixture of enantiomers, such as a racemic mixture, may be preferred. Thus, in one embodiment of the invention the compound of formula (I) is the racemic mixture (the racemate).

Alternatively, a single enantiomer may be preferred, for example the enantiomer 1. Thus, in one embodiment of the invention the compound of formula (I) is the enantiomer 1. In a further embodiment of the invention the compound of formula (I) is the enantiomer 2.

It will be appreciated by those skilled in the art that, for compounds of formula (I) wherein rotation of the aryl-carbonyl bond becomes less facile due to ortho substitution on the aromatic ring, for example when $R^1$ is methyl or ethyl, $R^2$ is chlorine and $R^3$ is fluorine, an axis of asymmetry may be observed thus introducing atropisomerism into the compound and creating the possibility of four isomers namely atropisomer 1, enantiomer 1 (A1E1); atropisomer 1, enantiomer 2 (A1E2); atropisomer 2, enantiomer 1 (A2E1); and atropisomer 2, enantiomer 2 (A2E2). Any comment relating to the biological activity of an isomer or stereoisomer should be taken to include these atropisomers. It will be appreciated by those skilled in the art that where there is a non 1:1 ratio of atropisomers, that this ratio can change depending on the half life of interconversion.

It will be further appreciated by those skilled in the art that, for compounds of formula (I) wherein rotation is restricted around the C(O)—$NR^1$ bond due to substitution of the amide, for example when $R^1$ is ethyl or 2-fluoroethyl, rotamers may be observed. Any comment relating to the biological activity of an isomer or stereoisomer should be taken to include these rotamers. It will be appreciated by those skilled in the art that there may not be a 1:1 ratio of rotamers as the ratio can change depending on the half life of interconversion.

The terms "stereoisomer" and "isomer" as used herein encompass enantiomer, atropisomer and/or rotamer.

The compounds of the invention are glucocorticoid receptor binders. Accordingly, it has been found that at least one of the possible enantiomers of each of the compounds of formula (I) binds to the glucocorticoid receptor.

Further, it appears that at least one of the possible enantiomers of each of the compounds of formula (I) has glucocorticoid receptor agonist activity. Accordingly, at least one of the possible enantiomers of each compound of formula (I) modulates the glucocorticoid receptor. The term "modulator" as used herein refers to a compound which binds to the glucocorticoid receptor and acts as either an agonist, a partial agonist or an antagonist of the glucocorticoid receptor.

The compounds of the invention may provide agonism of the glucocorticoid receptor.

Additionally, it appears that one or more of the possible enantiomers of some of the compounds of formula (I) possess advantageous selectivity in respect of maintaining transrepression activity whilst reducing the transactivation activity. These observations are believed to be indicative that the compounds of the invention provide anti-inflammatory properties with fewer or less severe related side effects.

Certain compounds of the invention may show a propensity to partition into the brain. Agents which show a higher propensity to partition into the brain may allow therapeutic concentrations to be achieved within the CNS with a significant reduction in the systemic glucocorticoid burden, resulting in an reduced risk from the known systemic effects of glucocorticoids (such as osteoporosis, diabetes, myopathy, skin thinning and weight gain).

In one embodiment, $R^1$ is selected from hydrogen, methyl and ethyl. In another embodiment, $R^1$ is selected from methyl and ethyl. In another embodiment, Fe is selected from hydrogen and ethyl. In another embodiment, $R^1$ is hydrogen. In a further embodiment, $R^1$ is ethyl.

In one embodiment, when $R^1$ is hydrogen or methyl, $R^2$ and $R^3$ are each independently selected from chlorine and fluorine. In a further embodiment, when $R^1$ is ethyl, $R^2$ and $R^3$ are each independently selected from chlorine and fluorine, or $R^2$ is $-SO_2CH_3$ and $R^3$ is hydrogen.

In one embodiment, $R^2$ and $R^3$ are each chlorine. In another embodiment, $R^2$ and $R^3$ are each fluorine. In another embodiment, $R^2$ is chlorine and $R^3$ is fluorine. In another embodiment, $R^2$ is $-SO_2CH_3$ and $R^3$ is hydrogen. In another embodiment, $R^2$ and $R^3$ are each bromine. In a further embodiment, $R^2$ is bromine and $R^3$ is chlorine.

In one embodiment $R^2$ is fluorine and $R^3$ is bromine. In another embodiment $R^2$ is chlorine and $R^3$ is $-OCHF_2$. In another embodiment $R^2$ and $R^3$ are both $-CHF_2$. In another embodiment $R^2$ and $R^3$ are each independently selected from fluorine, chlorine, bromine, $-OCHF_2$ and $-CHF_2$. In a further embodiment $R^2$ is fluorine and $R^3$ is $-OCHF_2$.

In one embodiment, n is 1.

In one embodiment, when n is 1, X is fluorine. In a further embodiment, the fluorine is in the para position on the phenyl ring.

It is to be understood that the present invention covers all combinations of substituent groups described hereinabove.

In a further embodiment, the present invention provides compounds of formula (IB):

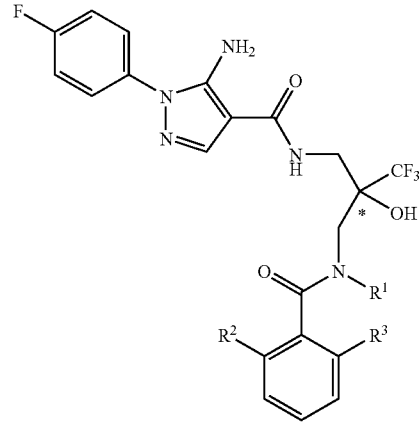

(IB)

* = chiral centre wherein
$R^1$ is selected from hydrogen and ethyl;
$R^2$ and $R^3$ are each independently selected from fluorine, chlorine, bromine, $-OCHF_2$ and $-CHF_2$; and
salts and solvates thereof.

In one embodiment, the compound of formula (I) is:
5-amino-N-(2-{[[(2,6-dichlorophenyl)carbonyl](methyl)amino]methyl}-3,3,3-trifluoro-2-hydroxypropyl)-1-(4-fluorophenyl)-1H-pyrazole-4-carboxamide;
5-amino-N-(2-{[[(2,6-dichlorophenyl)carbonyl](methyl)amino]methyl}-3,3,3-trifluoro-2-hydroxypropyl)-1-(4-fluorophenyl)-1H-pyrazole-4-carboxamide (Enantiomer 1);
5-amino-N-(2-{[[(2,6-dichlorophenyl)carbonyl](methyl)amino]methyl}-3,3,3-trifluoro-2-hydroxypropyl)-1-(4-fluorophenyl)-1H-pyrazole-4-carboxamide (Enantiomer 2);
5-amino-N-(2-{[[(2,6-dichlorophenyl)carbonyl](ethyl)amino]methyl}-3,3,3-trifluoro-2-hydroxypropyl)-1-(4-fluorophenyl)-1H-pyrazole-4-carboxamide;
5-amino-N-(2-{[[(2,6-dichlorophenyl)carbonyl](ethyl)amino]methyl}-3,3,3-trifluoro-2-hydroxypropyl)-1-(4-fluorophenyl)-1H-pyrazole-4-carboxamide (Enantiomer 1);
5-amino-N-(2-{[[(2,6-dichlorophenyl)carbonyl](ethyl)amino]methyl}-3,3,3-trifluoro-2-hydroxypropyl)-1-(4-fluorophenyl)-1H-pyrazole-4-carboxamide (Enantiomer 2);
5-amino-N-[2-({[(2,6-dichlorophenyl)carbonyl]amino}methyl)-3,3,3-trifluoro-2-hydroxypropyl]-1-(4-fluorophenyl)-1H-pyrazole-4-carboxamide;
5-amino-N-[2-({[(2,6-dichlorophenyl)carbonyl]amino}methyl)-3,3,3-trifluoro-2-hydroxypropyl]-1-(4-fluorophenyl)-1H-pyrazole-4-carboxamide (Enantiomer 1);
5-amino-N-[2-({[(2,6-dichlorophenyl)carbonyl]amino}methyl)-3,3,3-trifluoro-2-hydroxypropyl]-1-(4-fluorophenyl)-1H-pyrazole-4-carboxamide (Enantiomer 2);
5-amino-N-(2-{[[(2-chloro-6-fluorophenyl)carbonyl](ethyl)amino]methyl}-3,3,3-trifluoro-2-hydroxypropyl)-1-(4-fluorophenyl)-1H-pyrazole-4-carboxamide;
5-amino-N-(2-{[[(2-chloro-6-fluorophenyl)carbonyl](ethyl)amino]methyl}-3,3,3-trifluoro-2-hydroxypropyl)-1-(4-fluorophenyl)-1H-pyrazole-4-carboxamide (Enantiomer 1);

5-amino-N-(2-{[[(2-chloro-6-fluorophenyl)carbonyl](ethyl)
amino]methyl}-3,3,3-trifluoro-2-hydroxypropyl)-1-(4-
fluorophenyl)-1H-pyrazole-4-carboxamide (Enantiomer
2);

5-amino-N-(2-{[[(2,6-difluorophenyl)carbonyl](ethyl)
amino]methyl}-3,3,3-trifluoro-2-hydroxypropyl)-1-(4-
fluorophenyl)-1H-pyrazole-4-carboxamide;

5-amino-N-(2-{[[(2,6-difluorophenyl)carbonyl](ethyl)
amino]methyl}-3,3,3-trifluoro-2-hydroxypropyl)-1-(4-
fluorophenyl)-1H-pyrazole-4-carboxamide (Enantiomer
1);

5-amino-N-(2-{[[(2,6-difluorophenyl)carbonyl](ethyl)
amino]methyl}-3,3,3-trifluoro-2-hydroxypropyl)-1-(4-
fluorophenyl)-1H-pyrazole-4-carboxamide (Enantiomer
2);

5-amino-N-[2-({[(2,6-difluorophenyl)carbonyl]
amino}methyl)-3,3,3-trifluoro-2-hydroxypropyl]-1-(4-
fluorophenyl)-1H-pyrazole-4-carboxamide;

5-amino-N-[2-({[(2-chloro-6-fluorophenyl)carbonyl]
amino}methyl)-3,3,3-trifluoro-2-hydroxypropyl]-1-(4-
fluorophenyl)-1H-pyrazole-4-carboxamide;

5-amino-N-[2-({[(2-chloro-6-fluorophenyl)carbonyl]
amino}methyl)-3,3,3-trifluoro-2-hydroxypropyl]-1-(4-
fluorophenyl)-1H-pyrazole-4-carboxamide (Enantiomer
1);

5-amino-N-[2-({[(2-chloro-6-fluorophenyl)carbonyl]
amino}methyl)-3,3,3-trifluoro-2-hydroxypropyl]-1-(4-
fluorophenyl)-1H-pyrazole-4-carboxamide (Enantiomer
2);

5-amino-N-(2-{[[(2,6-difluorophenyl)carbonyl](methyl)
amino]methyl}-3,3,3-trifluoro-2-hydroxypropyl)-1-(4-
fluorophenyl)-1H-pyrazole-4-carboxamide;

5-amino-N-(2-{[[(2-chloro-6-fluorophenyl)carbonyl](methyl)amino]methyl}-3,3,3-trifluoro-2-hydroxypropyl)-1-
(4-fluorophenyl)-1H-pyrazole-4-carboxamide;

5-amino-N-{2-[(ethyl{[2-(methylsulfonyl)phenyl]
carbonyl}amino)methyl]-3,3,3-trifluoro-2-hydroxypropyl}-1-(4-fluorophenyl)-1H-pyrazole-4-carboxamide;

5-amino-N-{2-[(ethyl{[2-(methylsulfonyl)phenyl]
carbonyl}amino)methyl]-3,3,3-trifluoro-2-hydroxypropyl}-1-(4-fluorophenyl)-1H-pyrazole-4-carboxamide
(Enantiomer 1);

5-amino-N-{2-[(ethyl{[2-(methylsulfonyl)phenyl]
carbonyl}amino)methyl]-3,3,3-trifluoro-2-hydroxypropyl}-1-(4-fluorophenyl)-1H-pyrazole-4-carboxamide
(Enantiomer 2);

5-amino-N-[2-({[(2,6-dibromophenyl)carbonyl]
amino}methyl)-3,3,3-trifluoro-2-hydroxypropyl]-1-(4-
fluorophenyl)-1H-pyrazole-4-carboxamide;

5-amino-N-[2-({[(2,6-dibromophenyl)carbonyl]
amino}methyl)-3,3,3-trifluoro-2-hydroxypropyl]-1-(4-
fluorophenyl)-1H-pyrazole-4-carboxamide (Enantiomer
1);

5-amino-N-[2-({[(2,6-dibromophenyl)carbonyl]
amino}methyl)-3,3,3-trifluoro-2-hydroxypropyl]-1-(4-
fluorophenyl)-1H-pyrazole-4-carboxamide (Enantiomer
2);

5-amino-N-[2-({[(2-bromo-6-chlorophenyl)carbonyl]
amino}methyl)-3,3,3-trifluoro-2-hydroxypropyl]-1-(4-
fluorophenyl)-1H-pyrazole-4-carboxamide;

5-amino-N-[2-({[(2-bromo-6-chlorophenyl)carbonyl]
amino}methyl)-3,3,3-trifluoro-2-hydroxypropyl]-1-(4-
fluorophenyl)-1H-pyrazole-4-carboxamide (Enantiomer
1);

5-amino-N-[2-({[(2-bromo-6-chlorophenyl)carbonyl]
amino}methyl)-3,3,3-trifluoro-2-hydroxypropyl]-1-(4-
fluorophenyl)-1H-pyrazole-4-carboxamide (Enantiomer
2);

5-amino-N-[2-({[(2-bromo-6-fluorophenyl)carbonyl]
amino}methyl)-3,3,3-trifluoro-2-hydroxypropyl]-1-(4-
fluorophenyl)-1H-pyrazole-4-carboxamide;

5-amino-N-[2-({[(2-bromo-6-fluorophenyl)carbonyl]
amino}methyl)-3,3,3-trifluoro-2-hydroxypropyl]-1-(4-
fluorophenyl)-1H-pyrazole-4-carboxamide (Enantiomer
1);

5-amino-N-[2-({[(2-bromo-6-fluorophenyl)carbonyl]
amino}methyl)-3,3,3-trifluoro-2-hydroxypropyl]-1-(4-
fluorophenyl)-1H-pyrazole-4-carboxamide (Enantiomer
2);

5-amino-N-(2-{[(2-chloro-6-[(difluoromethyl)oxy]
phenyl}carbonyl)amino]methyl}-3,3,3-trifluoro-2-hydroxypropyl)-1-(4-fluorophenyl)-1H-pyrazole-4-carboxamide;

5-amino-N-(2-{[({2-chloro-6-[(difluoromethyl)oxy)phenyl]
carbonyl}amino]methyl}-3,3,3-trifluoro-2-hydroxypropyl)-1-(4-fluorophenyl)-1H-pyrazole-4-carboxamide
(Enantiomer 1);

5-amino-N-(2-{[({2-chloro-6-[(difluoromethyl)oxy)phenyl]
carbonyl}amino]methyl}-3,3,3-trifluoro-2-hydroxypropyl)-1-(4-fluorophenyl)-1H-pyrazole-4-carboxamide
(Enantiomer 2);

5-amino-N-{2-[({[2,6-bis(trifluoromethyl)phenyl]
carbonyl}amino)methyl]-3,3,3-trifluoro-2-hydroxypropyl}-1-(4-fluorophenyl)-1H-pyrazole-4-carboxamide;

5-amino-N-{2-[({[2,6-bis(trifluoromethyl)phenyl]
carbonyl}amino)methyl]-3,3,3-trifluoro-2-hydroxypropyl}-1-(4-fluorophenyl)-1H-pyrazole-4-carboxamide
(Enantiomer 1);

5-amino-N-{2-[({[2,6-bis(trifluoromethyl)phenyl]
carbonyl}amino)methyl]-3,3,3-trifluoro-2-hydroxypropyl}-1-(4-fluorophenyl)-1H-pyrazole-4-carboxamide
(Enantiomer 2);

5-amino-N-(2-{[[(2-bromo-6-chlorophenyl)carbonyl](methyl)amino]methyl}-3,3,3-trifluoro-2-hydroxypropyl)-1-
(4-fluorophenyl)-1H-pyrazole-4-carboxamide;

5-amino-N-(2-{[[(2,6-difluorophenyl)carbonyl](2-fluoroethyl)amino]methyl}-3,3,3-trifluoro-2-hydroxypropyl)-1-
(4-fluorophenyl)-1H-pyrazole-4-carboxamide;

5-amino-1-(4-fluorophenyl)-N-{3,3,3-trifluoro-2-[((2-fluoroethyl){[2-fluoro-6-(trifluoromethyl)phenyl]
carbonyl}amino)methyl]-2-hydroxypropyl}-1H-pyrazole-4-carboxamide;

5-amino-1-(4-fluorophenyl)-N-{3,3,3-trifluoro-2-[({[2-fluoro-6-(trifluoromethyl)phenyl]carbonyl}amino)methyl]-2-hydroxypropyl}-1H-pyrazole-4-carboxamide;

5-amino-1-(4-fluorophenyl)-N-{3,3,3-trifluoro-2-[({[2-fluoro-6-(trifluoromethyl)phenyl]carbonyl}amino)methyl]-2-hydroxypropyl}-1H-pyrazole-4-carboxamide
(Enantiomer 1);

5-amino-1-(4-fluorophenyl)-N-{3,3,3-trifluoro-2-[({[2-fluoro-6-(trifluoromethyl)phenyl]carbonyl}amino)methyl]-2-hydroxypropyl}-1H-pyrazole-4-carboxamide
(Enantiomer 2);

5-amino-N-(2-{[({2,6-bis[(difluoromethyl)oxy]
phenyl}carbonyl)amino]methyl}-3,3,3-trifluoro-2-hydroxypropyl)-1-(4-fluorophenyl)-1H-pyrazole-4-carboxamide;

5-amino-1-(4-fluorophenyl)-N-(3,3,3-trifluoro-2-{[{[2-fluoro-6-(trifluoromethyl)phenyl]carbonyl}(methyl)
amino]methyl}-2-hydroxypropyl)-1H-pyrazole-4-carboxamide;

5-amino-N-(2-{[{[2,6-bis(trifluoromethyl)phenyl]carbo-nyl}(methyl)amino]methyl}-3,3,3-trifluoro-2-hydroxypropyl)-1-(4-fluorophenyl)-1H-pyrazole-4-carboxamide;

5-amino-N-{2-[(ethyl{[2-fluoro-6-(trifluoromethyl)phenyl]carbonyl}amino)methyl]-3,3,3-trifluoro-2-hydroxypropyl}-1-(4-fluorophenyl)-1H-pyrazole-4-carboxamide;

5-amino-N-(2-{[[(2-bromo-6-chlorophenyl)carbonyl](ethyl)amino]methyl}-3,3,3-trifluoro-2-hydroxypropyl)-1-(4-fluorophenyl)-1H-pyrazole-4-carboxamide;

5-amino-N-(2-{[({2-chloro-6-[(difluoromethyl)oxy]phenyl}carbonyl)(ethyl)amino]methyl}-3,3,3-trifluoro-2-hydroxypropyl)-1-(4-fluorophenyl)-1H-pyrazole-4-carboxamide;

5-amino-N-(2-{[({2,6-bis[(difluoromethyl)oxy]phenyl}carbonyl)(ethyl)amino]methyl}-3,3,3-trifluoro-2-hydroxypropyl)-1-(4-fluorophenyl)-1H-pyrazole-4-carboxamide;

5-amino-N-(2-{[{[2,6-bis(trifluoromethyl)phenyl]carbonyl}(ethyl)amino]methyl}-3,3,3-trifluoro-2-hydroxypropyl)-1-(4-fluorophenyl)-1H-pyrazole-4-carboxamide;

5-amino-N-(2-{[[(2,6-dichlorophenyl)carbonyl](2-fluoroethyl)amino]methyl}-3,3,3-trifluoro-2-hydroxypropyl)-1-(4-fluorophenyl)-1H-pyrazole-4-carboxamide;

5-amino-N-(2-{[[(2-chloro-6-fluorophenyl)carbonyl](2-fluoroethyl)amino]methyl}-3,3,3-trifluoro-2-hydroxypropyl)-1-(4-fluorophenyl)-1H-pyrazole-4-carboxamide;

5-amino-N-(2-{[[(2-bromo-6-chlorophenyl)carbonyl](2-fluoroethyl)amino]methyl}-3,3,3-trifluoro-2-hydroxypropyl)-1-(4-fluorophenyl)-1H-pyrazole-4-carboxamide;

5-amino-N-(2-{[({2-chloro-6-[(difluoromethyl)oxy]phenyl}carbonyl)(2-fluoroethyl)amino]methyl}-3,3,3-trifluoro-2-hydroxypropyl)-1-(4-fluorophenyl)-1H-pyrazole-4-carboxamide;

5-amino-N-(2-{[({2,6-bis[(difluoromethyl)oxy]phenyl}carbonyl)(2-fluoroethyl)amino]methyl}-3,3,3-trifluoro-2-hydroxypropyl)-1-(4-fluorophenyl)-1H-pyrazole-4-carboxamide;

5-amino-1-(3,4-difluorophenyl)-N-(2-{[[(2,6-difluorophenyl)carbonyl]ethyl]amino]methyl}-3,3,3-trifluoro-2-hydroxypropyl)-1H-pyrazole-4-carboxamide;

5-amino-1-(2,4-difluorophenyl)-N-(2-{[[(2,6-difluorophenyl)carbonyl](ethyl)amino]methyl}-3,3,3-trifluoro-2-hydroxypropyl)-1H-pyrazole-4-carboxamide;

5-amino-1-(3,5-difluorophenyl)-N-(2-{[[(2,6-difluorophenyl)carbonyl](ethyl)amino]methyl}-3,3,3-trifluoro-2-hydroxypropyl)-1H-pyrazole-4-carboxamide;

5-amino-1-(2,5-difluorophenyl)-N-(2-{[[(2,6-difluorophenyl)carbonyl](ethyl)amino]methyl}-3,3,3-trifluoro-2-hydroxypropyl)-1H-pyrazole-4-carboxamide;

5-amino-1-(2,6-difluorophenyl)-N-(2-{[[(2,6-difluorophenyl)carbonyl](ethyl)amino]methyl}-3,3,3-trifluoro-2-hydroxypropyl)-1H-pyrazole-4-carboxamide;

5-amino-N-(2-{[[(2,6-difluorophenyl)carbonyl](ethyl)amino]methyl}-3,3,3-trifluoro-2-hydroxypropyl)-1-(3-fluorophenyl)-1H-pyrazole-4-carboxamide;

5-amino-1-(4-chlorophenyl)-N-(2-{[[(2,6-difluorophenyl)carbonyl](ethyl)amino]methyl}-3,3,3-trifluoro-2-hydroxypropyl)-1H-pyrazole-4-carboxamide;

5-amino-1-(2-chlorophenyl)-N-(2-{[[(2,6-difluorophenyl)carbonyl](ethyl)amino]methyl}-3,3,3-trifluoro-2-hydroxypropyl)-1H-pyrazole-4-carboxamide;

5-amino-1-(3-chlorophenyl)-N-(2-{[[(2,6-difluorophenyl)carbonyl](ethyl)amino]methyl}-3,3,3-trifluoro-2-hydroxypropyl)-1H-pyrazole-4-carboxamide;

5-amino-N-(2-{[[(2,6-difluorophenyl)carbonyl](ethyl)amino]methyl}-3,3,3-trifluoro-2-hydroxypropyl)-1-(2-fluorophenyl)-1H-pyrazole-4-carboxamide;

5-amino-N-{2-[({[2,6-bis(difluoromethyl)phenyl]carbonyl}amino)methyl]-3,3,3-trifluoro-2-hydroxypropyl}-1-(4-fluorophenyl)-1H-pyrazole-4-carboxamide;

5-amino-N-{2-[({[2,6-bis(difluoromethyl)phenyl]carbonyl}amino)methyl]-3,3,3-trifluoro-2-hydroxypropyl}-1-(4-fluorophenyl)-1H-pyrazole-4-carboxamide (Enantiomer 1);

5-amino-N-{2-[({[2,6-bis(difluoromethyl)phenyl]carbonyl}amino)methyl]-3,3,3-trifluoro-2-hydroxypropyl}-1-(4-fluorophenyl)-1H-pyrazole-4-carboxamide (Enantiomer 2);

5-amino-N-{2-[({[2-chloro-6-(trifluoromethyl)phenyl]carbonyl}amino)methyl]-3,3,3-trifluoro-2-hydroxypropyl}-1-(4-fluorophenyl)-1H-pyrazole-4-carboxamide;

5-amino-N-{2-[({[2-chloro-6-(trifluoromethyl)phenyl]carbonyl}amino)methyl]-3,3,3-trifluoro-2-hydroxypropyl}-1-(4-fluorophenyl)-1H-pyrazole-4-carboxamide (Enantiomer 1);

5-amino-N-{2-[({[2-chloro-6-(trifluoromethyl)phenyl]carbonyl}amino)methyl]-3,3,3-trifluoro-2-hydroxypropyl}-1-(4-fluorophenyl)-1H-pyrazole-4-carboxamide (Enantiomer 2);

5-amino-N-{2-[({[2-bromo-6-(trifluoromethyl)phenyl]carbonyl}amino)methyl]-3,3,3-trifluoro-2-hydroxypropyl}-1-(4-fluorophenyl)-1H-pyrazole-4-carboxamide;

5-amino-N-{2-[({[2-bromo-6-(trifluoromethyl)phenyl]carbonyl}amino)methyl]-3,3,3-trifluoro-2-hydroxypropyl}-1-(4-fluorophenyl)-1H-pyrazole-4-carboxamide (Enantiomer 1);

5-amino-N-{2-[({[2-bromo-6-(trifluoromethyl)phenyl]carbonyl}amino)methyl]-3,3,3-trifluoro-2-hydroxypropyl}-1-(4-fluorophenyl)-1H-pyrazole-4-carboxamide (Enantiomer 2);

5-amino-N-(2-{[({2-[(difluoromethyl)oxy]-6-fluorophenyl}carbonyl)amino]methyl}-3,3,3-trifluoro-2-hydroxypropyl)-1-(4-fluorophenyl)-1H-pyrazole-4-carboxamide;

5-amino-N-(2-{[({2-[(difluoromethyl)oxy]-6-fluorophenyl}carbonyl)amino]methyl}-3,3,3-trifluoro-2-hydroxypropyl)-1-(4-fluorophenyl)-1H-pyrazole-4-carboxamide (Enantiomer 1);

5-amino-N-(2-{[({2-[(difluoromethyl)oxy]-6-fluorophenyl}carbonyl)amino]methyl}-3,3,3-trifluoro-2-hydroxypropyl)-1-(4-fluorophenyl)-1H-pyrazole-4-carboxamide (Enantiomer 2);

or a salt or solvate thereof.

In another embodiment, the compound of formula (I) is:

5-amino-N-[2-({[(2,6-dichlorophenyl)carbonyl]amino}methyl)-3,3,3-trifluoro-2-hydroxypropyl]-1-(4-fluorophenyl)-1H-pyrazole-4-carboxamide;

5-amino-N-[2-({[(2,6-dichlorophenyl)carbonyl]amino}methyl)-3,3,3-trifluoro-2-hydroxypropyl]-1-(4-fluorophenyl)-1H-pyrazole-4-carboxamide (Enantiomer 1);

5-amino-N-[2-({[(2,6-dichlorophenyl)carbonyl]amino}methyl)-3,3,3-trifluoro-2-hydroxypropyl]-1-(4-fluorophenyl)-1H-pyrazole-4-carboxamide (Enantiomer 2);

5-amino-N-(2-{[[(2,6-difluorophenyl)carbonyl](ethyl)amino]methyl}-3,3,3-trifluoro-2-hydroxypropyl)-1-(4-fluorophenyl)-1H-pyrazole-4-carboxamide;

5-amino-N-(2-{[[(2,6-difluorophenyl)carbonyl](ethyl)
amino]methyl}-3,3,3-trifluoro-2-hydroxypropyl)-1-(4-
fluorophenyl)-1H-pyrazole-4-carboxamide (Enantiomer
1);
5-amino-N-(2-{[[(2,6-difluorophenyl)carbonyl](ethyl)
amino]methyl}-3,3,3-trifluoro-2-hydroxypropyl)-1-(4-
fluorophenyl)-1H-pyrazole-4-carboxamide (Enantiomer
2);
5-amino-N-[2-({[(2-chloro-6-fluorophenyl)carbonyl]
amino}methyl)-3,3,3-trifluoro-2-hydroxypropyl]-1-(4-
fluorophenyl)-1H-pyrazole-4-carboxamide;
5-amino-N-[2-({[(2-chloro-6-fluorophenyl)carbonyl]
amino}methyl)-3,3,3-trifluoro-2-hydroxypropyl]-1-(4-
fluorophenyl)-1H-pyrazole-4-carboxamide (Enantiomer
1);
5-amino-N-[2-({[(2-chloro-6-fluorophenyl)carbonyl]
amino}methyl)-3,3,3-trifluoro-2-hydroxypropyl]-1-(4-
fluorophenyl)-1H-pyrazole-4-carboxamide (Enantiomer
2);
5-amino-N-[2-({[(2-bromo-6-fluorophenyl)carbonyl]
amino}methyl)-3,3,3-trifluoro-2-hydroxypropyl]-1-(4-
fluorophenyl)-1H-pyrazole-4-carboxamide;
5-amino-N-[2-({[(2-bromo-6-fluorophenyl)carbonyl]
amino}methyl)-3,3,3-trifluoro-2-hydroxypropyl]-1-(4-
fluorophenyl)-1H-pyrazole-4-carboxamide (Enantiomer
1);
5-amino-N-[2-({[(2-bromo-6-fluorophenyl)carbonyl]
amino}methyl)-3,3,3-trifluoro-2-hydroxypropyl]-1-(4-
fluorophenyl)-1H-pyrazole-4-carboxamide (Enantiomer
2);
5-amino-N-(2-{[({2-chloro-6-[(difluoromethyl)oxy]
phenyl}carbonyl)amino]methyl}-3,3,3-trifluoro-2-hy-
droxypropyl)-1-(4-fluorophenyl)-1H-pyrazole-4-car-
boxamide;
5-amino-N-(2-{[({2-chloro-6-[(difluoromethyl)oxy]
phenyl}carbonyl)amino]methyl}-3,3,3-trifluoro-2-hy-
droxypropyl)-1-(4-fluorophenyl)-1H-pyrazole-4-car-
boxamide (Enantiomer 1);
5-amino-N-(2-{[({2-chloro-6-[(difluoromethyl)oxy]
phenyl}carbonyl)amino]methyl}-3,3,3-trifluoro-2-hy-
droxypropyl)-1-(4-fluorophenyl)-1H-pyrazole-4-car-
boxamide (Enantiomer 2);
5-amino-N-{2-[({[2,6-bis(difluoromethyl)phenyl]
carbonyl}amino)methyl]-3,3,3-trifluoro-2-hydroxypro-
pyl}-1-(4-fluorophenyl)-1H-pyrazole-4-carboxamide;
5-amino-N-{2-[({[2,6-bis(difluoromethyl)phenyl]
carbonyl}amino)methyl]-3,3,3-trifluoro-2-hydroxypro-
pyl}-1-(4-fluorophenyl)-1H-pyrazole-4-carboxamide
(Enantiomer 1);
5-amino-N-{2-[({[2,6-bis(difluoromethyl)phenyl]
carbonyl}amino)methyl]-3,3,3-trifluoro-2-hydroxypro-
pyl}-1-(4-fluorophenyl)-1H-pyrazole-4-carboxamide
(Enantiomer 2);
5-amino-N-(2-{[({2-[(difluoromethyl)oxy]-6-
fluorophenyl}carbonyl)amino]methyl}-3,3,3-trifluoro-2-
hydroxypropyl)-1-(4-fluorophenyl)-1H-pyrazole-4-car-
boxamide;
5-amino-N-(2-{[({2-[(difluoromethyl)oxy]-6-
fluorophenyl}carbonyl)amino]methyl}-3,3,3-trifluoro-2-
hydroxypropyl)-1-(4-fluorophenyl)-1H-pyrazole-4-car-
boxamide (Enantiomer 1);
5-amino-N-(2-{[({2-[(difluoromethyl)oxy]-6-
fluorophenyl}carbonyl)amino]methyl}-3,3,3-trifluoro-2-
hydroxypropyl)-1-(4-fluorophenyl)-1H-pyrazole-4-car-
boxamide (Enantiomer 2);
or a salt or solvate thereof.

In another embodiment, the compound of formula (I) is:
5-amino-N-[2-({[(2,6-dichlorophenyl)carbonyl]
amino}methyl)-3,3,3-trifluoro-2-hydroxypropyl]-1-(4-
fluorophenyl)-1H-pyrazole-4-carboxamide;
5-amino-N-[2-({[(2,6-dichlorophenyl)carbonyl]
amino}methyl)-3,3,3-trifluoro-2-hydroxypropyl]-1-(4-
fluorophenyl)-1H-pyrazole-4-carboxamide (Enantiomer
1);
5-amino-N-[2-({[(2,6-dichlorophenyl)carbonyl]
amino}methyl)-3,3,3-trifluoro-2-hydroxypropyl]-1-(4-
fluorophenyl)-1H-pyrazole-4-carboxamide (Enantiomer
2); or
a salt or solvate thereof.
In a further embodiment the compound of formula (I) is:
5-amino-N-[2-({[[(2,6-dichlorophenyl)carbonyl]amino]me-
thyl}-3,3,3-trifluoro-2-hydroxypropyl]-1-(4-fluorophe-
nyl)-1H-pyrazole-4-carboxamide (Enantiomer 2); or
a salt or solvate thereof.
In another embodiment, the compound of formula (I) is:
5-amino-N-(2-{[[(2,6-difluorophenyl)carbonyl](ethyl)
amino]methyl}-3,3,3-trifluoro-2-hydroxypropyl)-1-(4-
fluorophenyl)-1H-pyrazole-4-carboxamide;
5-amino-N-(2-{[[(2,6-difluorophenyl)carbonyl](ethyl)
amino]methyl}-3,3,3-trifluoro-2-hydroxypropyl)-1-(4-
fluorophenyl)-1H-pyrazole-4-carboxamide (Enantiomer
1);
5-amino-N-(2-{[[(2,6-difluorophenyl)carbonyl](ethyl)
amino]methyl}-3,3,3-trifluoro-2-hydroxypropyl)-1-(4-
fluorophenyl)-1H-pyrazole-4-carboxamide (Enantiomer
2); or
a salt or solvate thereof.
In another embodiment, the compound of formula (I) is:
5-amino-N-(2-{[[(2,6-difluorophenyl)carbonyl](ethyl)
amino]methyl}-3,3,3-trifluoro-2-hydroxypropyl)-1-(4-
fluorophenyl)-1H-pyrazole-4-carboxamide (Enantiomer
2); or
a salt or solvate thereof.
In another embodiment, the compound of formula (I) is:
5-amino-N-[2-({[(2-chloro-6-fluorophenyl)carbonyl]
amino}methyl)-3,3,3-trifluoro-2-hydroxypropyl]-1-(4-
fluorophenyl)-1H-pyrazole-4-carboxamide;
5-amino-N-[2-({[(2-chloro-6-fluorophenyl)carbonyl]
amino}methyl)-3,3,3-trifluoro-2-hydroxypropyl]-1-(4-
fluorophenyl)-1H-pyrazole-4-carboxamide (Enantiomer
1);
5-amino-N-[2-({[(2-chloro-6-fluorophenyl)carbonyl]
amino}methyl)-3,3,3-trifluoro-2-hydroxypropyl]-1-(4-
fluorophenyl)-1H-pyrazole-4-carboxamide (Enantiomer
2); or
a salt or solvate thereof.
In another embodiment, the compound of formula (I) is:
5-amino-N-[2-({[(2-bromo-6-fluorophenyl)carbonyl]
amino}methyl)-3,3,3-trifluoro-2-hydroxypropyl]-1-(4-
fluorophenyl)-1H-pyrazole-4-carboxamide;
5-amino-N-[2-({[(2-bromo-6-fluorophenyl)carbonyl]
amino}methyl)-3,3,3-trifluoro-2-hydroxypropyl]-1-(4-
fluorophenyl)-1H-pyrazole-4-carboxamide (Enantiomer
1);
5-amino-N-[2-({[(2-bromo-6-fluorophenyl)carbonyl]
amino}methyl)-3,3,3-trifluoro-2-hydroxypropyl]-1-(4-
fluorophenyl)-1H-pyrazole-4-carboxamide (Enantiomer
2); or
a salt or solvate thereof.

In another embodiment, the compound of formula (I) is:

5-amino-N-(2-{[({2-chloro-6-[(difluoromethyl)oxy]phenyl}carbonyl)amino]methyl}-3,3,3-trifluoro-2-hydroxypropyl)-1-(4-fluorophenyl)-1H-pyrazole-4-carboxamide;

5-amino-N-(2-{[({2-chloro-6-[(difluoromethyl)oxy]phenyl}carbonyl)amino]methyl}-3,3,3-trifluoro-2-hydroxypropyl)-1-(4-fluorophenyl)-1H-pyrazole-4-carboxamide (Enantiomer 1);

5-amino-N-(2-{[({2-chloro-6-[(difluoromethyl)oxy]phenyl}carbonyl)amino]methyl}-3,3,3-trifluoro-2-hydroxypropyl)-1-(4-fluorophenyl)-1H-pyrazole-4-carboxamide (Enantiomer 2);

or a salt or solvate thereof.

In another embodiment, the compound of formula (I) is:

5-amino-N-{2-[({[2,6-bis(difluoromethyl)phenyl]carbonyl}amino)methyl]-3,3,3-trifluoro-2-hydroxypropyl}-1-(4-fluorophenyl)-1H-pyrazole-4-carboxamide;

5-amino-N-{2-[({[2,6-bis(difluoromethyl)phenyl]carbonyl}amino)methyl]-3,3,3-trifluoro-2-hydroxypropyl}-1-(4-fluorophenyl)-1H-pyrazole-4-carboxamide (Enantiomer 1);

5-amino-N-{2-[({[2,6-bis(difluoromethyl)phenyl]carbonyl}amino)methyl]-3,3,3-trifluoro-2-hydroxypropyl}-1-(4-fluorophenyl)-1H-pyrazole-4-carboxamide (Enantiomer 2); or a salt or solvate thereof.

In a further embodiment, the compound of formula (I) is:

5-amino-N-(2-{[({2-[(difluoromethyl)oxy]-6-fluorophenyl}carbonyl)amino]methyl}-3,3,3-trifluoro-2-hydroxypropyl)-1-(4-fluorophenyl)-1H-pyrazole-4-carboxamide;

5-amino-N-(2-{[({2-[(difluoromethyl)oxy]-6-fluorophenyl}carbonyl)amino]methyl}-3,3,3-trifluoro-2-hydroxypropyl)-1-(4-fluorophenyl)-1H-pyrazole-4-carboxamide (Enantiomer 1);

5-amino-N-(2-{[({2-[(difluoromethyl)oxy]-6-fluorophenyl}carbonyl)amino]methyl}-3,3,3-trifluoro-2-hydroxypropyl)-1-(4-fluorophenyl)-1H-pyrazole-4-carboxamide (Enantiomer 2);

or a salt or solvate thereof.

One embodiment of the invention embraces compounds of formula (I) and salts and solvates thereof. Another embodiment of the invention embraces compounds of formula (I) and salts thereof. Another embodiment of the invention embraces compounds of formula (I) and solvates thereof. A further embodiment of the invention embraces compounds of formula (I) as the free base.

Salts and solvates of the compounds of formula (I) which are suitable for use in medicine are those wherein the counter-ion or associated solvent is pharmaceutically acceptable. However, salts and solvates having non-pharmaceutically acceptable counter-ions or associated solvents are within the scope of the present invention, for example, for use as intermediates in the preparation of other compounds of formula (I) and their pharmaceutically acceptable salts and solvates.

Suitable salts according to the invention include those formed with both organic and inorganic acids or bases. Pharmaceutically acceptable acid addition salts may include those formed from hydrochloric, hydrobromic, sulphuric, phosphoric, trifluoroacetic, sulphamic, sulphanilic, methanesulphonic, ethanesulphonic, formic and arylsulphonic (for example p-toluenesulphonic, benzenesulphonic, naphthalenesulphonic or naphthalenedisulphonic) acids. Pharmaceutically acceptable base salts may include alkali metal salts such as those of sodium and potassium and alkaline earth metal salts such as those of calcium.

Examples of solvates include hydrates.

The compounds of the invention may have the ability to crystallise in more than one form. This is a characteristic known as polymorphism, and it is understood that such polymorphic forms ("polymorphs") are within the scope of the present invention. Polymorphism generally can occur as a response to changes in temperature or pressure or both and can also result from variations in the crystallisation process. Polymorphs can be distinguished by various physical characteristics known in the art such as x-ray diffraction patterns, solubility, and melting point.

The compounds of the invention are expected to have beneficial anti-inflammatory and/or anti-allergic and/or auto-immune effects, particularly upon oral administration, demonstrated by, for example, their ability to bind to the glucocorticoid receptor and to elicit a response via that receptor. Hence, the compounds of the invention may be of use in the treatment of an inflammatory and/or allergic disorder and/or auto-immune condition.

Examples of disease states associated with glucocorticoid receptor activity include skin diseases such as eczema, psoriasis, allergic dermatitis, neurodermatitis, pruritis, exfoliative dermatitis, pemphigus and hypersensitivity reactions; inflammatory conditions of the nose, throat or lungs such as asthma (including allergen-induced asthmatic reactions), rhinitis (including seasonal (hayfever), allergic and vasomotor), nasal polyps, chronic obstructive pulmonary disease (COPD), interstitial lung disease, and fibrosis; inflammatory bowel conditions such as ulcerative colitis and Crohn's disease; auto-immune diseases such as rheumatoid arthritis, termporal arteritis, polyarteritis nodosa, polymyositis, ankylosing spondylitis, sarcoidosis, autoimmune hepatitis; cancers such as acute and lymphatic leukaemia, myeloma, lymphoma; nephritic syndrome; septic shock; adrenal insufficiency; ophthalmic inflammation and allergic conjunctivitis; obesity; diabetes; chronic inflammatory pain including musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea; psychiatric disease for example schizophrenia, depression (which term is used herein to include bipolar depression, unipolar depression, single or recurrent major depressive episodes with or without psychotic features, catatonic features, melancholic features, atypical features or postpartum onset, seasonal affective disorder, dysthymic disorders with early or late onset and with or without atypical features, neurotic depression and social phobia, depression accompanying dementia for example of the Alzheimer's type, schizoaffective disorder or the depressed type, and depressive disorders resulting from general medical conditions including, but not limited to, myocardial infarction, diabetes, miscarriage or abortion, etc), anxiety disorders (including generalised anxiety disorder and social anxiety disorder), panic disorder, agoraphobia, social phobia, obsessive compulsive disorder and post-traumatic stress disorder, memory disorders, including dementia, amnesic disorders and age-associated memory impairment, disorders of eating behaviours, including anorexia nervosa and bulimia nervosa, sleep disorders (including disturbances of circadian rhythm, dyssomnia, insomnia, sleep apnea and narcolepsy), withdrawal from abuse of drugs such as of cocaine, ethanol, nicotine, benzodiazepines, alcohol, caffeine, phencyclidine (phencyclidine-like compounds), opiates (e.g. cannabis, heroin, morphine), amphetamine or amphetamine-related drugs (e.g. dextroamphetamine, methylamphetamine) or a combination thereof. Compounds having glucocorticoid receptor activity may also have utility in inducing suppression of the immune system during organ transplantation, in acute transplant reject, angioedema of the upper respiratory tract and anaphylactic shock.

Examples of disease states in which the compounds of the present invention are expected to have utility include rheumatoid arthritis, asthma, COPD, allergy and rhinitis.

Further examples of disease states include multiple sclerosis, cerebral vasculitis, neurosarcoidosis, Sjogren's syndrome, systemic lupus erythematosis, acute or chronic inflammatory polyradiculopathy, Alzheimer's disease, neoplastic diseases of the nervous system including meningioma, lymphoma and malignant meningitis, and trauma and infectious diseases of the nervous system such as tuberculosis. Other conditions include spinal cord injury and brain injury, for example post-infarction (stroke).

An example of a disease state in which the compounds of the present invention are expected to have utility includes neurosarcoidosis.

It will be appreciated by those skilled in the art that reference herein to treatment extends to prophylaxis as well as the treatment of established conditions.

As mentioned above, compounds of formula (I) and pharmaceutically acceptable salts and solvates thereof are expected to be of use in human or veterinary medicine, in particular as anti-inflammatory and/or anti-allergic agents. Compounds of formula (I) and pharmaceutically acceptable salts and solvates thereof are also expected to be of use in the treatment of patients with an inflammatory and/or auto-immune condition.

There is thus provided as one aspect of the invention a compound of formula (I) or a pharmaceutically acceptable salt or solvate thereof for use in therapy.

In another aspect of the invention there is provided a compound of formula (I) or a pharmaceutically acceptable salt or solvate thereof for use in the treatment of patients with an inflammatory and/or allergic condition.

In another aspect of the invention there is provided a compound of formula (I) or a pharmaceutically acceptable salt or solvate thereof for use in the treatment of patients with rheumatoid arthritis, asthma, COPD, allergy and/or rhinitis.

In another aspect of the invention there is provided a compound of formula (I) or a pharmaceutically acceptable salt or solvate thereof for use in the treatment of patients with rheumatoid arthritis.

In another aspect of the invention there is provided a compound of formula (I) or a pharmaceutically acceptable salt or solvate thereof for use in the treatment of patients with skin disease.

In another aspect of the invention there is provided a compound of formula (I) or a pharmaceutically acceptable salt or solvate thereof for use in the treatment of patients with eczema, psoriasis, allergic dermatitis, neurodermatitis, pruritis and/or hypersensitivity reactions.

In another aspect of the invention there is provided a compound of formula (I) or a pharmaceutically acceptable salt or solvate thereof for use in the treatment of patients with an inflammatory and/or auto-immune condition.

In another aspect of the invention there is provided a compound of formula (I) or a pharmaceutically acceptable salt or solvate thereof for use in the treatment of patients with inflammation within the central nervous system.

In another aspect of the invention there is provided a compound of formula (I) or a pharmaceutically acceptable salt or solvate thereof for use in the treatment of patients with multiple sclerosis, cerebral vasculitis, neurosarcoidosis, Sjogren's syndrome, systemic lupus erythematosis, acute or chronic inflammatory polyradiculopathy, Alzheimer's disease, neoplastic diseases of the nervous system including meningioma, lymphoma and malignant meningitis, trauma or infectious diseases of the nervous system such as tuberculosis, spinal cord injury or brain injury such as post-infarction (stroke).

In a further aspect of the invention there is provided a compound of formula (I) or a pharmaceutically acceptable salt or solvate thereof for use in the treatment of patients with neurosarcoidosis.

According to another aspect of the invention, there is provided the use of a compound of formula (I) or a pharmaceutically acceptable salt or solvate thereof for the manufacture of a medicament for the treatment of patients with an inflammatory and/or allergic condition.

According to another aspect of the invention, there is provided the use of a compound of formula (I) or a pharmaceutically acceptable salt or solvate thereof for the manufacture of a medicament for the treatment of patients with rheumatoid arthritis, asthma, COPD, allergy and/or rhinitis.

According to another aspect of the invention, there is provided the use of a compound of formula (I) or a pharmaceutically acceptable salt or solvate thereof for the manufacture of a medicament for the treatment of patients with rheumatoid arthritis.

According to another aspect of the invention, there is provided the use of a compound of formula (I) or a pharmaceutically acceptable salt or solvate thereof for the manufacture of a medicament for the treatment of patients with skin disease.

According to another aspect of the invention, there is provided the use of a compound of formula (I) or a pharmaceutically acceptable salt or solvate thereof for the manufacture of a medicament for the treatment of patients with eczema, psoriasis, allergic dermatitis, neurodermatitis, pruritis and/or hypersensitivity reactions.

According to another aspect of the invention, there is provided the use of a compound of formula (I) or a pharmaceutically acceptable salt or solvate thereof for the manufacture of a medicament for the treatment of patients with an inflammatory and/or auto-immune condition.

According to another aspect of the invention, there is provided the use of a compound of formula (I) or a pharmaceutically acceptable salt or solvate thereof for the manufacture of a medicament for the treatment of patients with inflammation within the central nervous system.

According to another aspect of the invention, there is provided the use of a compound of formula (I) or a pharmaceutically acceptable salt or solvate thereof for the manufacture of a medicament for the treatment of patients with multiple sclerosis, cerebral vasculitis, neurosarcoidosis, Sjogren's syndrome, systemic lupus erythematosis, acute or chronic inflammatory polyradiculopathy, Alzheimer's disease, neoplastic diseases of the nervous system including meningioma, lymphoma and malignant meningitis, trauma or infectious diseases of the nervous system such as tuberculosis, spinal cord injury or brain injury such as post-infarction (stroke).

According to a further aspect of the invention, there is provided the use of a compound of formula (I) or a pharmaceutically acceptable salt or solvate thereof for the manufacture of a medicament for the treatment of patients with neurosarcoidosis.

In another aspect of the present invention, there is provided a method for the treatment of a human or animal subject with an inflammatory and/or allergic condition which method comprises administering to said human or animal subject an effective amount of a compound of formula (I) or a pharmaceutically acceptable salt or solvate thereof.

In a another aspect, there is provided a method for the treatment of a human or animal subject with rheumatoid arthritis, asthma, COPD, allergy and/or rhinitis which method comprises administering to said human or animal subject an effective amount of a compound of formula (I) or a pharmaceutically acceptable salt or solvate thereof.

In another aspect, there is provided a method for the treatment of a human or animal subject with rheumatoid arthritis which method comprises administering to said human or animal subject an effective amount of a compound of formula (I) or a pharmaceutically acceptable salt or solvate thereof.

In another aspect, there is provided a method for the treatment of a human or animal subject with skin disease which method comprises administering to said human or animal subject an effective amount of a compound of formula (I) or a pharmaceutically acceptable salt or solvate thereof.

In another aspect, there is provided a method for the treatment of a human or animal subject with eczema, psoriasis, allergic dermatitis, neurodermatitis, pruritis and/or hypersensitivity reactions which method comprises administering to said human or animal subject an effective amount of a compound of formula (I) or a pharmaceutically acceptable salt or solvate thereof.

In another aspect, there is provided a method for the treatment of a human or animal subject with an inflammatory and/or auto-immune condition which method comprises administering to said human or animal subject an effective amount of a compound of formula (I) or a pharmaceutically acceptable salt or solvate thereof.

In another aspect, there is provided a method for the treatment of a human or animal subject with a condition involving inflammation within the central nervous system which method comprises administering to said human or animal subject an effective amount of a compound of formula (I) or a pharmaceutically acceptable salt or solvate thereof.

In another aspect, there is provided a method for the treatment of a human or animal subject with multiple sclerosis, cerebral vasculitis, neurosarcoidosis, Sjogren's syndrome, systemic lupus erythematosis, acute or chronic inflammatory polyradiculopathy, Alzheimer's disease, neoplastic diseases of the nervous system including meningioma, lymphoma and malignant meningitis, trauma or infectious diseases of the nervous system such as tuberculosis, spinal cord injury or brain injury such as post-infarction (stroke), which method comprises administering to said human or animal subject an effective amount of a compound of formula (I) or a pharmaceutically acceptable salt or solvate thereof.

In a further aspect, there is provided a method for the treatment of a human or animal subject with neurosarcoidosis which method comprises administering to said human or animal subject an effective amount of a compound of formula (I) or a pharmaceutically acceptable salt or solvate thereof.

The compounds of formula (I) or a pharmaceutically acceptable salt or solvate thereof may be formulated for administration in any convenient way, and the invention therefore also includes within its scope pharmaceutical compositions comprising a compound of formula (I) or a pharmaceutically acceptable salt or solvate thereof together, if desirable, in admixture with one or more pharmaceutically acceptable diluents or carriers.

Further, there is provided a process for the preparation of such pharmaceutical compositions which comprises mixing the ingredients.

The compounds of formula (I) or a pharmaceutically acceptable salt or solvate thereof may, for example, be formulated for oral, nasal, inhaled, buccal, sublingual, parenteral, topical rectal administration or other topical administration.

For systemic administration the compounds according to the invention may, for example, be formulated in conventional manner for oral, parenteral or rectal administration. Formulations for oral administration include solutions, syrups, elixirs, powders, granules, tablets and capsules which typically contain conventional excipients such as binding agents, fillers, lubricants, disintegrants, wetting agents, suspending agents, emulsifying agents, preservatives, buffer salts, flavouring, colouring and/or sweetening agents as appropriate. Dosage unit forms may be preferred as described below.

For instance, for oral administration in the form of a tablet or capsule, the active drug component can be combined with an oral, non-toxic pharmaceutically acceptable inert carrier such as ethanol, glycerol, water and the like. The tablets may also contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Examples of excipients in this regard include lactose, starch, a cellulose, milk sugar or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

Powders are prepared by comminuting the compound to a suitable fine size and mixing with a similarly comminuted pharmaceutical carrier such as an edible carbohydrate, as, for example, starch or mannitol. Flavouring, preservative, dispersing and colouring agent can also be present.

Capsules can be made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavoured aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavour additives such as peppermint oil or saccharin, and the like can also be added. Where appropriate, dosage unit formulations for oral administration can be microencapsulated. The formulation can also be prepared to prolong or sustain the release as for example by coating or embedding particulate material in polymers, wax or the like.

The compounds of formula (I) or a pharmaceutically acceptable salt or solvate thereof can also be administered in the form of liposome emulsion delivery systems, such as small unilamellar vesicles, large unilamellar vesicles and multilamellar vesicles. Liposomes can be formed from a variety of phospholipids, such as cholesterol, stearylamine or phosphatidylcholines.

In one embodiment the compound of formula (I) or a pharmaceutically acceptable salt or solvate thereof is in the form of a tablet or capsule for oral administration for the treatment of rheumatoid arthritis. In another embodiment the compound of formula (I) or a pharmaceutically acceptable salt or solvate thereof is in the form of a tablet or capsule for oral administration for the treatment of neurosarcoidosis.

In one embodiment the compound of formula (I) or a pharmaceutically acceptable salt or solvate thereof is in the form of a solution, syrup or elixir for oral administration for the treatment of rheumatoid arthritis. In another embodiment the compound of formula (I) or a pharmaceutically acceptable salt or solvate thereof is in the form of a solution, syrup or elixir for oral administration for the treatment of neurosarcoidosis.

Topical administration as used herein, includes administration by insufflation and inhalation. Examples of various types of preparation for topical administration include ointments, lotions, creams, gels, foams, preparations for delivery by transdermal patches, powders, sprays, aerosols, capsules or cartridges for use in an inhaler or insufflator or drops (e.g. eye or nose drops), solutions/suspensions for nebulisation, suppositories, pessaries, retention enemas and chewable or suckable tablets or pellets (e.g. for the treatment of aphthous ulcers) or liposome or microencapsulation preparations.

Formulations for administration topically to the nose for example, for the treatment of rhinitis, include pressurised aerosol formulations and aqueous formulations administered to the nose by pressurised pump. Formulations which are non-pressurised and adapted to be administered topically to the nasal cavity are of particular interest. Suitable formulations contain water as the diluent or carrier for this purpose. Aqueous formulations for administration to the lung or nose may be provided with conventional excipients such as buffering agents, tonicity modifying agents and the like. Aqueous formulations may also be administered to the nose by nebulisation.

In one embodiment the compounds of formula (I) or a pharmaceutically acceptable salt or solvate thereof may be formulated for administration topically to the nose as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO05/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. In one embodiment, the fluid dispenser is of the general type illustrated in FIGS. 30-40 of WO05/044354.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application, for example to the skin, may be formed with the aid of any suitable powder base, for example, talc, lactose or starch. Drops may be formulated with an aqueous or non-aqueous base also comprising one or more dispersing agents, solubilising agents, suspending agents or preservatives.

In one embodiment the compounds of formula (I) or a pharmaceutically acceptable salt or solvate thereof may be formulated as a dry powder for administration by inhalation.

Optionally, in particular for dry powder inhalable compositions, a composition suitable for inhaled administration may be incorporated into a plurality of sealed dose containers (e.g. containing the dry powder composition) mounted longitudinally in a strip or ribbon inside a suitable inhalation device. The container is rupturable or peel-openable on demand and the dose of e.g. the dry powder composition may be administered by inhalation via a device such as the DISKUS™ device, marketed by GlaxoSmithKline. The DISKUS™ inhalation device is, for example, described in GB2242134A, and in such a device, at least one container for the composition in powder form (the container or containers preferably being a plurality of sealed dose containers mounted longitudinally in a strip or ribbon) is defined between two members peelably secured to one another; the device comprises: a means of defining an opening station for the said container or containers; a means for peeling the members apart at the opening station to open the container; and an outlet, communicating with the opened container, through which a user can inhale the composition in powder form from the opened container.

Spray compositions for inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain a compound of formula (I) or a pharmaceutically acceptable salt or solvate thereof and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants e.g. oleic acid, lecithin or an oligolactic acid derivative e.g. as described in WO94/21229 and WO98/34596 and cosolvents e.g. ethanol.

There is thus provided as a further aspect of the invention a pharmaceutical aerosol formulation comprising a compound of formula (I) or a pharmaceutically acceptable salt or solvate thereof and a fluorocarbon or hydrogen-containing chlorofluorocarbon as propellant, optionally in combination with a surfactant and/or a cosolvent.

According to another aspect of the invention, there is provided a pharmaceutical aerosol formulation wherein the propellant is selected from 1,1,1,2-tetrafluoroethane, 1,1,1,2,3,3,3-heptafluoro-n-propane and mixtures thereof.

The formulations of the invention may be buffered by the addition of suitable buffering agents.

Aerosol formulations are preferably arranged so that each metered dose or "puff" of aerosol contains from 20 µg to 10 mg, preferably from 20 µg to 2000 µg, more preferably from about 20 µg to 50 µg of a compound of formula (I). Administration may be once daily or several times daily, for example 2, 3, 4 or 8 times, giving for example 1, 2 or 3 doses each time. The overall daily dose with an aerosol will be within the range from 100 µg to 10 mg, preferably from 200 µg to 2000 µg. The overall daily dose and the metered dose delivered by capsules and cartridges in an inhaler or insufflator will generally be double that delivered with aerosol formulations.

In the case of suspension aerosol formulations, the particle size of the particulate (e.g., micronised) drug should be such as to permit inhalation of substantially all the drug into the lungs upon administration of the aerosol formulation and will thus be less than 100 microns, desirably less than 20 microns, and in particular in the range of from 1 to 10 microns, such as from 1 to 5 microns, more preferably from 2 to 3 microns.

The formulations of the invention may be prepared by dispersal or dissolution of the medicament and a compound of the invention in the selected propellant in an appropriate container, for example, with the aid of sonication or a high-shear mixer. The process is desirably carried out under controlled humidity conditions.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The stability of the suspension aerosol formulations according to the invention may be measured by conventional techniques, for example, by measuring flocculation size distribution using a back light scattering instrument or by measuring particle size distribution by cascade impaction or by the "twin innpinger" analytical process. As used herein reference to the "twin innpinger" assay means "Determination of the deposition of the emitted dose in pressurised inhalations using apparatus A" as defined in British Pharmacopaeia 1988, pages A204-207, Appendix XVII C. Such techniques enable the "respirable fraction" of the aerosol formulations to be calculated. One method used to calculate the "respirable fraction" is by reference to "fine particle fraction" which is the amount of active ingredient collected in the lower impingement chamber per actuation expressed as a percentage of the total amount of active ingredient delivered per actuation using the twin impinger method described above.

MDI canisters generally comprise a container capable of withstanding the vapour pressure of the propellant used such as a plastic or plastic-coated glass bottle or preferably a metal can, for example, aluminium or an alloy thereof which may optionally be anodised, lacquer-coated and/or plastic-coated (for example incorporated herein by reference WO96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (e.g. see Byron, above and WO96/32099). Preferably the canister is fitted with a cap assembly, wherein a drug-metering valve is situated in the cap, and said cap is crimped in place.

The term "metered dose inhaler" or MDI means a unit comprising a can, a secured cap covering the can and a formulation metering valve situated in the cap. MDI system includes a suitable channelling device. Suitable channelling devices comprise for example, a valve actuator and a cylindrical or cone-like passage through which medicament may be delivered from the filled canister via the metering valve to the nose or mouth of a patient such as a mouthpiece actuator.

In one embodiment of the invention the metallic internal surface of the can is coated with a fluoropolymer, most preferably blended with a non-fluoropolymer. In another embodiment of the invention the metallic internal surface of the can is coated with a polymer blend of polytetrafluoroethylene (PTFE) and polyethersulfone (PES). In a further embodiment of the invention the whole of the metallic internal surface of the can is coated with a polymer blend of polytetrafluoroethylene (PTFE) and polyethersulfone (PES).

The metering valves are designed to deliver a metered amount of the formulation per actuation and incorporate a gasket to prevent leakage of propellant through the valve. The gasket may comprise any suitable elastomeric material such as, for example, low density polyethylene, chlorobutyl, bromobutyl, EPDM, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, LIK (e.g. BK300, BK357) and 3M-Neotechnic Ltd, UK (e.g. Spraymiser™)

In various embodiments, the MDIs may also be used in conjunction with other structures such as, without limitation, overwrap packages for storing and containing the MDIs, including those described in U.S. Pat. Nos. 6,119,853; 6,179,118; 6,315,112; 6,352,152; 6,390,291; and 6,679,374, as well as dose counter units such as, but not limited to, those described in U.S. Pat. Nos. 6,360,739 and 6,431,168.

Conventional bulk manufacturing methods and machinery well known to those skilled in the art of pharmaceutical aerosol manufacture may be employed for the preparation of large-scale batches for the commercial production of filled canisters. Thus, for example, in one bulk manufacturing method for preparing suspension aerosol formulations a metering valve is crimped onto an aluminium can to form an empty canister. The particulate medicament is added to a charge vessel and liquefied propellant together with the optional excipients is pressure filled through the charge vessel into a manufacturing vessel. The drug suspension is mixed before recirculation to a filling machine and an aliquot of the drug suspension is then filled through the metering valve into the canister. In one example bulk manufacturing method for preparing solution aerosol formulations a metering valve is crimped onto an aluminium can to form an empty canister. The liquefied propellant together with the optional excipients and the dissolved medicament is pressure filled through the charge vessel into a manufacturing vessel.

In an alternative process, an aliquot of the liquefied formulation is added to an open canister under conditions which are sufficiently cold to ensure the formulation does not vaporise, and then a metering valve crimped onto the canister.

Typically, in batches prepared for pharmaceutical use, each filled canister is check-weighed, coded with a batch number and packed into a tray for storage before release testing.

Capsules and cartridges for use in an inhaler or insufflator, of for example gelatine, may be formulated containing a powder mix for inhalation of a compound of the invention and a suitable powder base such as lactose or starch. Each capsule or cartridge may generally contain from 20 µg to 10 mg of the compound of formula (I) or a pharmaceutically acceptable salt or solvate thereof. Alternatively, the compound of formula (I) or a pharmaceutically acceptable salt or solvate thereof may be presented without excipients such as lactose.

The proportion of the active compound of formula (I) or a pharmaceutically acceptable salt or solvate thereof in the local compositions according to the invention depends on the precise type of formulation to be prepared but will generally be within the range of from 0.001 to 10% by weight. Generally, for most types of preparations, the proportion used will be within the range of from 0.005 to 1%, for example from 0.01 to 0.5%. However, in powders for inhalation or insufflation the proportion used will normally be within the range of from 0.1 to 5%.

Topical preparations may be administered by one or more applications per day to the affected area; over skin areas occlusive dressings may advantageously be used. Continuous or prolonged delivery may be achieved by an adhesive reservoir system.

Typically, a physician will determine the actual dosage which will be most suitable for an individual subject. The specific dose level and frequency of dosage for any particular individual may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

For oral administration to humans, the daily dosage level of the agent may be in single or divided doses.

For systemic administration the daily dose as employed for adult human treatment will range from 0.5-100 mg/kg body weight, preferably 0.5-60 mg/kg body weight, which may be administered in 1 to 4 daily doses, for example, depending on the route of administration and the condition of the patient. When the composition comprises dosage units, each unit will preferably contain 5 mg to 1 g of active ingredient. The duration of treatment will be dictated by the rate of response rather than by arbitrary numbers of days.

The compounds of the invention may in general be given by internal administration in cases wherein systemic glucocorticoid receptor agonist therapy is indicated.

Slow release or enteric coated formulations may be advantageous, particularly for the treatment of inflammatory bowel disorders.

In some embodiments, the compounds of the invention will be formulated for oral administration. In other embodiments, the compounds of the invention will be formulated for inhaled administration. In further embodiments, the compounds of the invention will be formulated for intranasal administration.

The compounds and pharmaceutical formulations according to the invention may be used in combination with or include one or more other therapeutic agents, for example when the compounds of the invention are administered intranasally or by inhalation. Suitable other therapeutic agents may be selected from for example anti-inflammatory agents, anticholinergic agents (particularly an $M_1/M_2/M_3$ receptor antagonist), $\beta_2$-adrenoreceptor agonists, antiinfective agents such as antibiotics or antivirals, or antihistamines (for example an H1 antagonist or an H1/H3 antagonist). The invention thus provides, in a further aspect, a combination comprising a compound of the invention together with one or more other therapeutically active agents, for example selected from an anti-inflammatory agent such as a corticosteroid or an NSAID, an anticholinergic agent, a $\beta_2$-adrenoreceptor agonist, an antiinfective agent such as an antibiotic or an antiviral, or an antihistamine. One embodiment of the invention encompasses combinations comprising a compound of the invention together with a $\beta_2$-adrenoreceptor agonist, and/or an anticholinergic, and/or a PDE-4 inhibitor, and/or an antihistamine.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

In one embodiment, the invention encompasses a combination comprising a compound of the invention together with a $\beta_2$-adrenoreceptor agonist.

Examples of $\beta_2$-adrenoreceptor agonists include salmeterol (e.g. as the racemate or a single enantiomer, such as the R-enantiomer), salbutamol (e.g. as the racemate or a single enantiomer such as the R-enantiomer), formoterol (e.g. as the racemate or a single diastereomer such as the R,R-diastereomer), salmefamol, fenoterol, carmoterol, etanterol, naminterol, clenbuterol, pirbuterol, flerobuterol, reproterol, bambuterol, indacaterol or terbutaline and salts thereof, for example the xinafoate (1-hydroxy-2-naphthalenecarboxylate) salt of salmeterol, the sulphate salt or free base of salbutamol or the fumarate salt of formoterol. In one embodiment, the $\beta_2$-adrenoreceptor agonists are long-acting $\beta_2$-adrenoreceptor agonists, for example compounds which provide effective bronchodilation for about 12 hours or longer.

Examples of $\beta_2$-adrenoreceptor agonists may include those described in WO02/066422A, WO02/070490, WO02/076933, WO03/024439, WO03/072539, WO 03/091204, WO04/016578, WO04/022547, WO04/037807, WO04/037773, WO04/037768, WO04/039762, WO04/039766, WO01/42193 and WO03/042160.

Examples of $\beta_2$-adrenoreceptor agonists include:
3-(4-{[6-({(2R)-2-hydroxy-2-[4-hydroxy-3-(hydroxymethyl)phenyl]ethyl}amino) hexyl]oxy}butyl)benzenesulfonamide;
3-(3-{[7-({(2R)-2-hydroxy-2-[4-hydroxy-3-hydroxymethyl)phenyl]ethyl}-amino)heptyl]oxy}propyl)benzenesulfonamide;
4-{(1R)-2-[(6-{2-[(2,6-dichlorobenzyl)oxy]ethoxy}hexyl) amino]-1-hydroxyethyl}-2-(hydroxymethyl)phenol;
4-{(1R)-2-[(6-{4-[3-(cyclopentylsulfonyl)phenyl] butoxy}hexyl)amino]-1-hydroxyethyl}-2-(hydroxymethyl)phenol;
N-[2-hydroxyl-5-[(1R)-1-hydroxy-2-[[2-4-[[(2R)-2-hydroxy-2-phenylethyl]amino]phenyl]ethyl]amino]ethyl] phenyl}foramide,
N-2{2-[4-(3-phenyl-4-methoxyphenyl)aminophenyl]ethyl}-2-hydroxy-2-(8-hydroxy-2(1H)-quinolinon-5-yl)ethylamine, and
5-[(R)-2-(2-{4-[4-(2-amino-2-methyl-propoxy)-phenylamino]-phenyl}-ethylamino)-1-hydroxy-ethyl]-8-hydroxy-1H-quinolin-2-one, and salts thereof.

The $\beta_2$-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

Suitable anti-inflammatory agents include corticosteroids. Examples of corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-1,3-hydroxy-16α-methyl-3-oxo-androsta-1,4-diene-17β-carbothioic acid S-fluoromethyl ester (fluticasone furoate), 6α,9α-difluoro-1,3-hydroxy-16α-methyl-3-oxo-17α-propionyloxy-androsta-1,4-diene-17β-carbothioic acid S-(2-oxo-tetrahydro-furan-3S-yl) ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-1,3-hydroxy-16α-methyl-17α-(1-methycyclopropylcarbonyl)oxy-3-oxo-androsta-1,4-diene-17β-carbothioic acid S-fluoromethyl ester, beclomethasone esters (for example the 17-propionate ester or the 17,21-dipropionate ester), budesonide, flunisolide, mometasone esters (for example mometasone furoate), triamcinolone acetonide, rofleponide, ciclesonide (16α,17-[[(R)-cyclohexylmethylene]bis(oxy)]-11β,21-dihydroxy-pregna-1,4-diene-3,20-dione), butixocort propionate, RPR-106541, and ST-126. In one embodiment corticosteroids include fluticasone propionate, 6α,9α-difluoro-1,3-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-1,3-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester. In one embodiment the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Examples of corticosteroids may include those described in WO02/088167, WO02/100879, WO02/12265, WO02/12266, WO05/005451, WO05/005452, WO06/072599 and WO06/072600.

Non-steroidal compounds having glucocorticoid agonism that may possess selectivity for transrepression over transactivation and that may be useful in combination therapy include those covered in the following published patent applications and patents: WO2003/082827, WO1998/54159, WO2004/005229, WO2004/009017, WO2004/018429, WO2003/104195, WO2003/082787, WO2003/082280, WO2003/059899, WO2003/101932, WO2002/02565, WO2001/16128, WO2000/66590, WO2003/086294, WO2004/026248, WO2003/061651, WO2003/08277, WO2006/000401, WO2006/000398 and WO2006/015870.

Examples of anti-inflammatory agents include non-steroidal anti-inflammatory drugs (NSAID's).

Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example, montelukast), iNOS inhibitors, tryptase and elastase inhibitors, beta-2 integrin antagonists and adenosine receptor agonists or antagonists (for example, adenosine 2a agonists), cytokine antagonists (for example, chemokine antagonists, such as a CCR3 antagonist) or inhibitors of cytokine synthesis, or 5-lipoxygenase inhibitors. An iNOS (inducible nitric oxide synthase inhibitor) is preferably for oral administration. Suitable iNOS inhibitors include those disclosed in WO93/13055, WO98/30537, WO02/50021, WO95/34534 and WO99/62875. Suitable CCR3 inhibitors include those disclosed in WO02/26722. Adenosine 2a agonists include those discussed in WO05/116037.

In one embodiment, the invention provides the use of the compounds of the invention in combination with a phosphodiesterase 4 (PDE4) inhibitor, for example in the case of a formulation adapted for inhalation. The PDE4-specific inhibitor may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl) cyclohexan-1-ol]. Another compound is cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep. 1996; this patent and the compounds it discloses are incorporated herein in full by reference.

Other compounds include AWD-12-281 (N-(3,5-dichloro-4-pyridinyl)-1-[4-fluorophenyl)methyl]-5-hydroxy-α-oxo-1H-indol-3-acetamide) from Elbion (Hofgen, N. et al. 15th EFMC Int Symp Med Chem (September 6-10, Edinburgh) 1998, Abst P. 98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P 2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6] naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds are disclosed in the published international patent application WO04/024728 (Glaxo Group Ltd), WO04/056823 (Glaxo Group Ltd) and WO04/103998 (Glaxo Group Ltd).

Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$ receptors or pan-antagonists of the $M_1/M_2/M_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS 136310-93-5, sold under the name Spiriva). Also of interest are revatropate (for example, as the hydrobromide, CAS 262586-79-8) and LAS-34273 which is disclosed in WO01/04118. Exemplary compounds for oral administration include pirenzepine (for example, CAS 28797-61-7), darifenacin (for example, CAS 133099-04-4, or CAS 133099-07-7 for the hydrobromide sold under the name Enablex), oxybutynin (for example, CAS 5633-20-5, sold under the name Ditropan), terodiline (for example, CAS 15793-40-5), tolterodine (for example, CAS 124937-51-5, or CAS 124937-52-6 for the tartrate, sold under the name Detrol), otilonium (for example, as the bromide, CAS 26095-59-0, sold under the name Spasmomen), trospium chloride (for example, CAS 10405-02-4) and solifenacin (for example, CAS 242478-37-1, or CAS 242478-38-2, or the succinate also known as YM-905 and sold under the name Vesicare).

Additional compounds are disclosed in WO 2005/037280, WO 2005/046586 and WO 2005/104745, incorporated herein by reference. The present combinations include, but are not limited to:

(3-endo)-3-(2,2-di-2-thienylethenyl)-8,8-dimethyl-8-azoniabicyclo[3.2.1]octane iodide;

(3-endo)-3-(2-cyano-2,2-diphenylethyl)-8,8-dimethyl-8-azoniabicyclo[3.2.1]octane bromide;

4-[hydroxy(diphenyl)methyl]-1-{2-[(phenylmethyl)oxy] ethyl}-1-azoniabicyclo[2.2.2]octane bromide; and (1R,5S)-3-(2-cyano-2,2-diphenylethyl)-8-methyl-8-{2-[(phenylmethyl)oxy]ethyl}-8-azoniabicyclo[3.2.1]octane bromide.

Other anticholinergic agents include compounds of formula (XXX), which are disclosed in U.S. patent application 60/487,981:

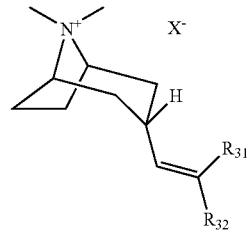

(XXX)

in which the preferred orientation of the alkyl chain attached to the tropane ring is endo; $R^{31}$ and $R^{32}$ are, independently, selected from the group consisting of straight or branched chain lower alkyl groups having preferably from 1 to 6 carbon atoms, cycloalkyl groups having from 5 to 6 carbon atoms, cycloalkyl-alkyl having from 6 to 10 carbon atoms, 2-thienyl, 2-pyridyl, phenyl, phenyl substituted with an alkyl group having not in excess of 4 carbon atoms and phenyl substituted with an alkoxy group having not in excess of 4 carbon atoms;

$X^-$ represents an anion associated with the positive charge of the N atom. $X^-$ may be but is not limited to chloride, bromide, iodide, sulfate, benzene sulfonate, and toluene sulfonate, including, for example:

(3-endo)-3-(2,2-di-2-thienylethenyl)-8,8-dimethyl-8-azoniabicyclo[3.2.1]octane bromide;

(3-endo)-3-(2,2-diphenylethenyl)-8,8-dimethyl-8-azoniabicyclo[3.2.1]octane bromide;

(3-endo)-3-(2,2-diphenylethenyl)-8,8-dimethyl-8-azoniabicyclo[3.2.1]octane 4-methylbenzenesulfonate;

(3-endo)-8,8-dimethyl-3-[2-phenyl-2-(2-thienyl)ethenyl]-8-azoniabicyclo[3.2.1]octane bromide; and/or (3-endo)-8,8-dimethyl-3-[2-phenyl-2-(2-pyridinyl)ethenyl]-8-azoniabicyclo[3.2.1]octane bromide.

Further anticholinergic agents include compounds of formula (XXXI) or (XXXII), which are disclosed in U.S. patent application 60/511,009:

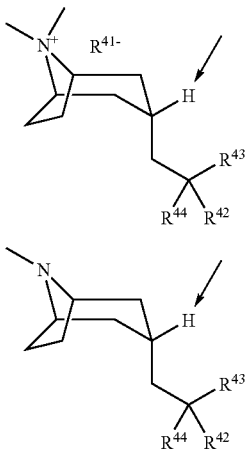

(XXXI)

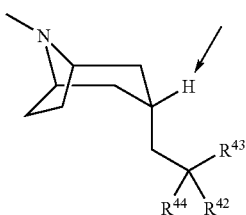

(XXXII)

wherein:
the H atom indicated is in the exo position;
$R^{41-}$ represents an anion associated with the positive charge of the N atom; $R^{41-}$ may be but is not limited to chloride, bromide, iodide, sulfate, benzene sulfonate and toluene sulfonate;
$R^{42}$ and $R^{43}$ are independently selected from the group consisting of straight or branched chain lower alkyl groups (having preferably from 1 to 6 carbon atoms), cycloalkyl groups (having from 5 to 6 carbon atoms), cycloalkyl-alkyl (having from 6 to 10 carbon atoms), heterocycloalkyl (having from 5 to 6 carbon atoms) and N or O as the heteroatom, heterocycloalkyl-alkyl (having from 6 to 10 carbon atoms) and N or O as the heteroatom, aryl, optionally substituted aryl, heteroaryl, and optionally substituted heteroaryl;
$R^{44}$ is selected from the group consisting of $(C_1-C_6)$alkyl, $(C_3-C_{12})$cycloalkyl, $(C_3-C_7)$heterocycloalkyl, $(C_1-C_6)$alkyl $(C_3-C_{12})$cycloalkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl, —$OR^{45}$, —$CH_2OR^{45}$, —$CH_2OH$, —$CN$, —$CF_3$, —$CH_2O(CO)R^{46}$, —$CO_2R^{47}$, —$CH_2NH_2$, —$CH_2N(R^{47})SO_2R^{45}$, —$SO_2N(R^{47})(R^{48})$, —$CON(R^{47})(R^{48})$, —$CH_2N(R^{48})CO(R^{46})$, —$CH_2N(R^{48})SO_2(R^{46})$, —$CH_2N(R^{48})CO_2(R^{45})$, —$CH_2N(R^{48})CONH(R^{47})$;
$R^{45}$ is selected from the group consisting of $(C_1-C_6)$alkyl, $(C_1-C_6)$alkyl$(C_3-C_{12})$cycloalkyl, $(C_1-C_6)$alkyl$(C_3-C_7)$heterocycloalkyl, $(C_1-C_6)$alkyl-aryl, $(C_1-C_6)$alkyl-heteroaryl;
$R^{46}$ is selected from the group consisting of $(C_1-C_6)$alkyl, $(C_3-C_{12})$cycloalkyl, $(C_3-C_7)$heterocycloalkyl, $(C_1-C_6)$alkyl $(C_3-C_{12})$cycloalkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl;
$R^{47}$ and $R^{48}$ are, independently, selected from the group consisting of H, $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$ alkyl$(C_3-C_7)$heterocycloalkyl, $(C_1-C_6)$alkyl-aryl, and $(C_1-C_6)$alkyl-heteroaryl, including, for example:
(endo)-3-(2-methoxy-2,2-di-thiophen-2-yl-ethyl)-8,8-dimethyl-8-azonia-bicyclo[3.2.1]octane iodide;
3-((endo)-8-methyl-8-aza-bicyclo[3.2.1]oct-3-yl)-2,2-diphenyl-propionitrile;
(endo)-8-methyl-3-(2,2,2-triphenyl-ethyl)-8-aza-bicyclo [3.2.1]octane;
3-((endo)-8-methyl-8-aza-bicyclo[3.2.1]oct-3-yl)-2,2-diphenyl-propionamide;
3-((endo)-8-methyl-8-aza-bicyclo[3.2.1]oct-3-yl)-2,2-diphenyl-propionic acid;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
3-((endo)-8-methyl-8-aza-bicyclo[3.2.1]oct-3-yl)-2,2-diphenyl-propan-1-ol;
N-benzyl-3-((endo)-8-methyl-8-aza-bicyclo[3.2.1]oct-3-yl)-2,2-diphenyl-propionamide;
(endo)-3-(2-carbamoyl-2,2-diphenyl-ethyl)-8,8-dimethyl-8-azonia-bicyclo[3.2.1]octane iodide;
1-benzyl-3-[3-((endo)-8-methyl-8-aza-bicyclo[3.2.1]oct-3-yl)-2,2-diphenyl-propyl]-urea;
1-ethyl-3-[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-acetamide;
N-[3-((endo)-8-methyl-8-aza-bicyclo[3.2.1]oct-3-yl)-2,2-diphenyl-propyl]-benzamide;
3-((endo)-8-methyl-8-aza-bicyclo[3.2.1]oct-3-yl)-2,2-di-thiophen-2-yl-propionitrile;
(endo)-3-(2-cyano-2,2-di-thiophen-2-yl-ethyl)-8,8-dimethyl-8-azonia-bicyclo[3.2.1]octane iodide;
N-[3-((endo)-8-methyl-8-aza-bicyclo[3.2.1]oct-3-yl)-2,2-diphenyl-propyl]-benzenesulfonamide;
[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-methanesulfonamide; and/or
(endo)-3-{2,2-diphenyl-3-[(1-phenyl-methanoyl)-amino]-propyl}-8,8-dimethyl-8-azonia-bicyclo[3.2.1]octane bromide.
Further compounds include:
(endo)-3-(2-methoxy-2,2-di-thiophen-2-yl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
(endo)-3-(2-carbamoyl-2,2-diphenyl-ethyl)-8,8-dimethyl-8-azonia-bicyclo[3.2.1]octane iodide;
(endo)-3-(2-cyano-2,2-di-thiophen-2-yl-ethyl)-8,8-dimethyl-8-azonia-bicyclo[3.2.1]octane iodide; and/or
(endo)-3-{2,2-diphenyl-3-[(1-phenyl-methanoyl)-amino]-propyl}-8,8-dimethyl-8-azonia-bicyclo[3.2.1]octane bromide.

Examples of antihistamines (also referred to as H1-receptor antagonists) include any one or more of the numerous antagonists known which inhibit H1-receptors, and are safe for human use. First generation antagonists, include derivatives of ethanolamines, ethylenediamines, and alkylamines, such as diphenylhydramine, pyrilamine, clemastine, chlorpheniramine. Second generation antagonists, which are non-sedating, include loratidine, desloratidine, terfenadine, astemizole, acrivastine, azelastine, levocetirizine fexofenadine and cetirizine.

Examples of anti-histamines include loratidine, desloratidine, fexofenadine, cetirizine, levocabastine, olopatadine, amlexanox and epinastine.

Suitable H1 antagonists include, without limitation, amlexanox, astemizole, azatadine, azelastine, acrivastine, brompheniramine, cetirizine, levocetirizine, efletirizine, chlorpheniramine, clemastine, cyclizine, carebastine, cyproheptadine, carbinoxannine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine. Another combination of interest is a combination comprising a compound of formula (I), or a pharmaceutically acceptable salt thereof together with an H3 antagonist (and/or inverse agonist). Suitable H3 antagonists include, for example, those compounds disclosed in WO2004/035556 and in WO2006/045416. Other histamine receptor antagonists which may be used in combination with the compounds of the present invention include antagonists (and/or inverse agonists) of the H4 receptor, for example, the compounds disclosed in Jablonowski et al., *J. Med. Chem.* 46:3957-3960 (2003). In a further embodiment, the invention provides a combination comprising a compound of formula (I) or a pharmaceutically acceptable salt thereof together with a dual H1/H3 antagonist. Examples of dual H1/H3 antagonists include 4-[(4-chlorophenyl)methyl]-2-({(2R)-1-[4-(4-{[3-(hexahydro-1H-azepin-1-yl)propyl]oxy}phenyl)butyl]-2-pyrrolidinyl}methyl)-1(2H)-phthalazinone or a pharmaceutically acceptable salt thereof as described in priority application GB0607839.8.

The invention thus provides, in a further aspect, a combination comprising a compound of the invention together with a PDE4 inhibitor.

The invention thus provides, in a further aspect, a combination comprising a compound of the invention together with a $\beta_2$-adrenoreceptor agonist.

The invention thus provides, in a further aspect, a combination comprising a compound of the invention together with a corticosteroid.

The invention thus provides, in a further aspect, a combination comprising a compound of the invention together with another non-steroidal GR agonist.

The invention thus provides, in a further aspect, a combination comprising a compound of the invention together with an anticholinergic.

The invention thus provides, in a further aspect, a combination comprising a compound of the invention together with an antihistamine.

The invention thus provides, in a further aspect, a combination comprising a compound of the invention together with an H1 antagonist.

The invention thus provides, in a further aspect, a combination comprising a compound of the invention together with an H1/H3 antagonist.

The invention thus provides, in a further aspect, a combination comprising a compound of the invention together with a PDE4 inhibitor and a $\beta_2$-adrenoreceptor agonist.

The invention thus provides, in a further aspect, a combination comprising a compound of the invention together with an anticholinergic and a PDE-4 inhibitor.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The individual compounds of such combinations may be administered either sequentially or simultaneously in separate or combined pharmaceutical compositions. In one embodiment, the individual compounds may be administered simultaneously in a combined pharmaceutical composition. Appropriate doses of known therapeutic agents will be readily appreciated by those skilled in the art.

The invention thus provides, in a further aspect, a pharmaceutical composition comprising a combination of a compound of the invention together with another therapeutically active agent.

The invention thus provides, in a further aspect, a pharmaceutical composition comprising a combination of a compound of the invention together with a PDE4 inhibitor.

The invention thus provides, in a further aspect, a pharmaceutical composition comprising a combination of a compound of the invention together with a $\beta_2$-adrenoreceptor agonist.

The invention thus provides, in a further aspect, a pharmaceutical composition comprising a combination of a compound of the invention together with a corticosteroid.

The invention thus provides, in a further aspect, a pharmaceutical composition comprising a combination of a compound of the invention together with another non-steroidal GR agonist.

The invention thus provides, in a further aspect, a pharmaceutical composition comprising a combination of a compound of the invention together with an anticholinergic.

The invention thus provides, in a further aspect, a pharmaceutical composition comprising a combination of a compound of the invention together with an antihistamine.

The invention thus provides, in a further aspect, a pharmaceutical composition comprising a combination of a compound of the invention together with an H1 antagonist.

The invention thus provides, in a further aspect, a pharmaceutical composition comprising a combination of a compound of the invention together with an H1/H3 antagonist.

The invention thus provides, in a further aspect, a pharmaceutical composition comprising a combination of a compound of the invention together with a PDE4 inhibitor and a $\beta_2$-adrenoreceptor agonist.

The invention thus provides, in a further aspect, a pharmaceutical composition comprising a combination of a compound of the invention together with an anticholinergic and a PDE-4 inhibitor.

The compounds of the invention may be prepared by the processes described below.

A process according to the invention for the preparation of compounds of formula (I) comprises reaction of an amine of formula (II)

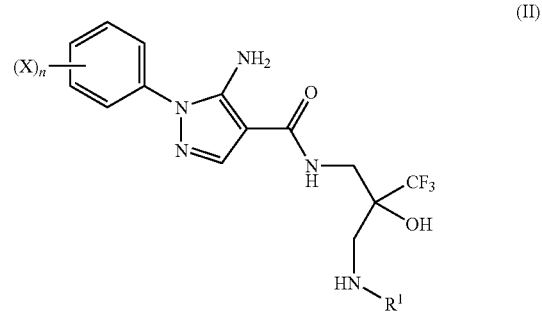

wherein $R^1$, X and n are as defined above for compounds of formula (I), with a compound of formula (III)

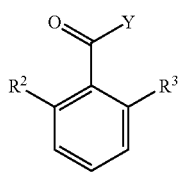

wherein $R^2$ and $R^3$ are as defined above for compounds of formula (I) and Y is chlorine or hydroxy.

When Y is chlorine, the reaction may be carried out in a conventional organic solvent, for example tetrahydrofuran, in the presence of a base, for example potassium carbonate, triethylamine, pyridine or diisopropylethylamine. In one embodiment, the reaction is carried out in the presence of diisopropylethylamine. The reaction may be carried out at a temperature of from −10° C. to 100° C., for example at room temperature.

Alternatively, when Y is hydroxy, the reaction may be carried out in a conventional organic solvent, for example dimethylformamide, in the presence of a coupling agent such as those described in Tetrahedron 2005, 61, 10827, for example 0-(7-azabenzotriazol-1-yl)-N,N,N',N'-tetramethyluronium hexafluorophosphate (HATU), and a base, for example triethylamine or diisopropylethylamine. In one embodiment, the reaction is carried out in the presence of diisopropylethylamine. The reaction may be carried out at a temperature of from −10° C. to 100° C., for example at room temperature.

Compounds of formula (II) wherein $R^1$ represents hydrogen, methyl, ethyl or 2-fluoroethyl may be prepared by reaction of a compound of formula (IV)

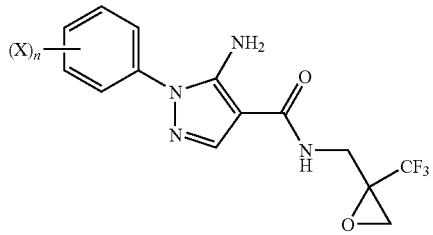

wherein X and n are as defined above for compounds of formula (I), with ammonia, methylamine, ethylamine or 2-fluoroethylamine (which can be generated from the hydrochloride salt and triethylamine) as appropriate. The reaction may be carried out in a conventional organic solvent, for example acetonitrile or tetrahydrofuran, and at a temperature of from −10° C. to 100° C., for example at room temperature.

In a further embodiment, a compound of formula (II) wherein $R^1$ is hydrogen may be prepared by hydrogenating a compound of formula (XXVI)

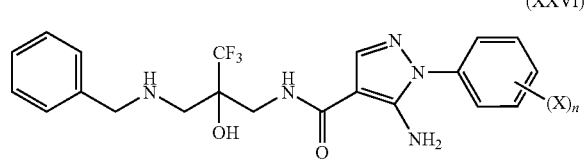

over 10% palladium on carbon.

A compound of formula (XXVI) may be prepared by treating a compound of formula (IV) as above, with benzylamine. The reaction may be carried out in dioxane at room temperature.

Alternatively, a compound of formula (II) wherein $R^1$ is hydrogen may be prepared by reacting a compound of formula (V)

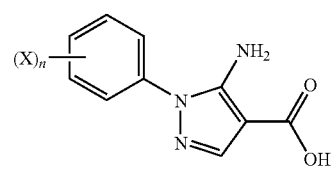

wherein X and n are as defined above for compounds of formula (I), with a compound of formula (VI)

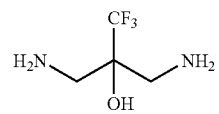

or alternatively with a compound of formula (XIX)

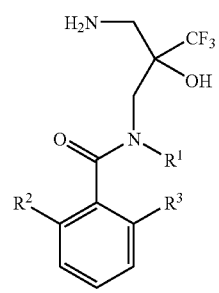

wherein $R^1$, $R^2$ and $R^3$ areas defined above for compounds of formula (I).

The reaction may be carried out in a conventional organic solvent, for example dimethylformamide, in the presence of a coupling agent such as those described in Tetrahedron 2005, 61, 10827, for example 0-(7-azabenzotriazol-1-yl)-N,N,N', N'-tetramethyluronium hexafluorophosphate (HATU), and a base, for example triethylamine or diisopropylethylamine. In one embodiment, the reaction is carried out in the presence of diisopropylethylamine. The reaction may be carried out at a temperature of from −10° C. to 100° C., for example at room temperature.

Example of acids of formula (V) suitable for use in this coupling reaction include:
5-amino-1-(2-fluorophenyl)-1H-pyrazole-4-carboxylic acid;
5-amino-1-(3-fluorophenyl)-1H-pyrazole-4-carboxylic acid;
5-amino-1-(4-fluorophenyl)-1H-pyrazole-4-carboxylic acid;
5-amino-1-(4-chlorophenyl)-1H-pyrazole-4-carboxylic acid;
5-amino-1-(3-chlorophenyl)-1H-pyrazole-4-carboxylic acid;
5-amino-1-(2-chlorophenyl)-1H-pyrazole-4-carboxylic acid;

5-amino-1-(2,3-difluorophenyl)-1H-pyrazole-4-carboxylic acid;
5-amino-1-(2,4-difluorophenyl)-1H-pyrazole-4-carboxylic acid;
5-amino-1-(2,5-difluorophenyl)-1H-pyrazole-4-carboxylic acid;
5-amino-1-(2,6-difluorophenyl)-1H-pyrazole-4-carboxylic acid;
5-amino-1-(3,4-difluorophenyl)-1H-pyrazole-4-carboxylic acid;
5-amino-1-(3,5-difluorophenyl)-1H-pyrazole-4-carboxylic acid; and
5-amino-1-phenyl-1H-pyrazole-4-carboxylic acid.

Acids of formula (V) may be prepared by, for example, reaction of a suitable aryl hydrazine with ethyl 2-cyano-3-ethoxyacrylate followed by conversion of the resulting ethyl ester to the corresponding acid by treatment with, for example, lithium hydroxide in a solvent such as aqueous ethanol.

Alternatively, a compound of formula (II) may be prepared by treating a compound of formula (VII)

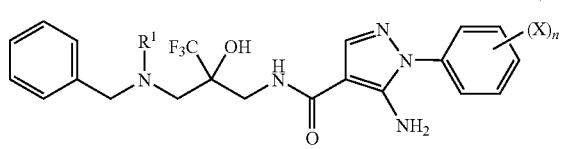
(VII)

wherein $R^1$, X and n are as defined above for compounds of formula (I), with a transition metal catalyst, for example palladium hydroxide on carbon, in the presence of a hydrogen atmosphere. The reaction may be carried out in a conventional organic solvent, for example ethanol. The reaction may be carried out at a temperature of from −10° C. to 100° C., for example at room temperature.

A compound of formula (VII) may be prepared by treating a compound of formula (V) as defined above, with a compound of formula (VIII)

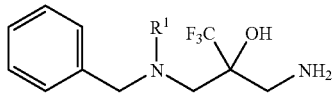
(VIII)

wherein $R^1$ is as defined above for compounds of formula (I), for example methyl, ethyl or 2-fluoroethyl.

The reaction may be carried out using similar conditions to those described above for the reaction of a compound of formula (V) with a compound of formula (VI).

A compound of formula (VIII) may be prepared by treating a compound of formula (IX)

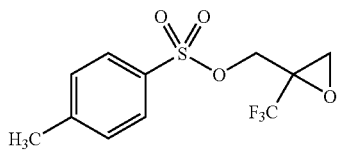
(IX)

initially with an N-alkyl benzylamine. The reaction may be carried out in a conventional organic solvent, for example 1,4-dioxan. The reaction may be carried out at a temperature of from −10° C. to 100° C., for example at room temperature. Subsequently, the reaction mixture can then be treated with a solution of ammonia in 1,4-dioxan. This reaction may be carried out at a temperature of from −10° C. to 100° C., for example at 100° C.

A compound of formula (IV) may be prepared by treating a compound of formula (X)

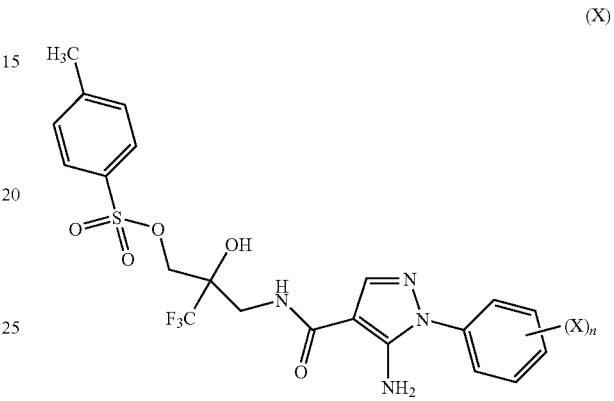
(X)

wherein X and n are as defined above for compounds of formula (I), with a polymer supported carbonate resin. The reaction may be carried out in a conventional organic solvent, for example tetrahydrofuran. The reaction may be carried out at a temperature of from −10° C. to 100° C., for example at room temperature.

A compound of formula (X) may be prepared by treating a compound of formula (XI)

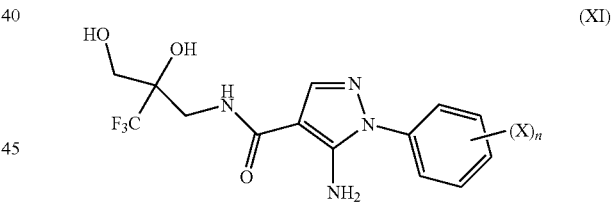
(XI)

wherein X and n are as defined above for compounds of formula (I), with 4-methylbenzenesulphonyl chloride. The reaction may be carried out in a conventional organic solvent, for example dichloromethane, in the presence of an organic base, for example pyridine. The reaction may be carried out at a temperature of from −10° C. to 100° C., for example at room temperature.

A compound of formula (XI) may be prepared by reacting a compound of formula (V) as defined above, with a compound of formula (XII)

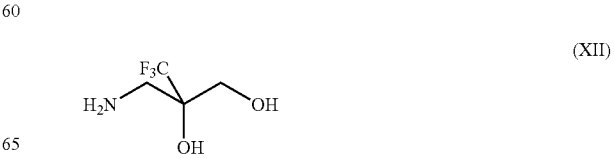
(XII)

The reaction may be carried out using similar conditions to those described above for the reaction of a compound of formula (V) with a compound of formula (VI).

A compound of formula (XII) may be prepared by treating a compound of formula (XIII)

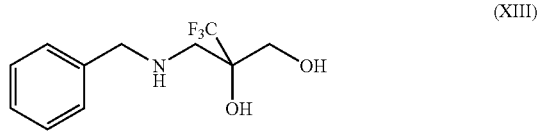

(XIII)

with a transition metal catalyst, for example palladium hydroxide on carbon, in the presence of a hydrogen atmosphere. The reaction may be carried out in a conventional organic solvent, for example ethanol. The reaction may be carried out at a temperature of from −10° C. to 100° C., for example at room temperature.

A compound of formula (XIII) may be prepared by treating a compound of formula (IX) as defined above with benzylamine followed by treatment with a base, for example sodium hydroxide. The reaction may be carried out in a conventional organic solvent, for example 1,4-dioxan. The treatment with benzylamine may be carried out at a temperature of from −10° C. to 100° C., for example at room temperature, and the treatment with base may be carried out at a temperature of from −10° C. to 100° C., for example at about 90° C.

A compound of formula (IX) may be prepared by treating a compound of formula (XIV)

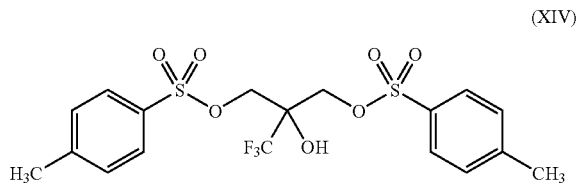

(XIV)

with a polymer supported carbonate resin. The reaction may be carried out in a conventional organic solvent, for example dichloromethane. Batch processes or flow processes are suitable equipment for this cyclisation. The reaction may be carried out at a temperature of from −10° C. to 100° C., for example at room temperature for a batch process or at about 50° C. for a flow process.

A compound of formula (XIV) may be prepared by treating a compound of formula (XV)

(XV)

with 4-methylbenzenesulphonyl chloride in the presence of an organic base, for example pyridine. The reaction may be carried out at a temperature of from −10° C. to 100° C., for example at room temperature. Alternatively, when a flow process is used, the compound of formula (XV) may be treated with 4-methylsulphonyl chloride in the presence of an organic base, for example N,N,N',N'-tetramethyl-1,6-hexanediamine, in dichloromethane at room temperature.

A compound of formula (XV) may be prepared by treating a compound of formula (XVI)

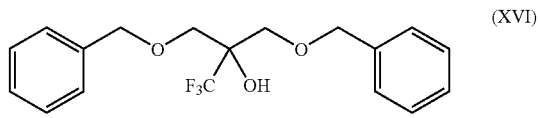

(XVI)

with a transition metal catalyst, for example 5% palladium on carbon, in the presence of a hydrogen atmosphere. The reaction may be carried out in a conventional organic solvent, for example ethanol. The reaction may be carried out at a temperature of from −10° C. to 100° C., for example at room temperature for a batch process or at about 80° C. for a flow process. Batch processes or flow processes are suitable for this hydrogenation.

A compound of formula (XVI) may be prepared by treating a compound of formula (XVII)

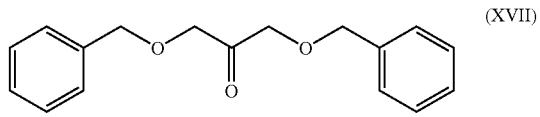

(XVII)

with trimethyl(trifluoromethyl)silane and tetra-n-butylammonium fluoride. The reaction may be carried out in a conventional organic solvent, for example tetrahydrofuran or dichloromethane. The reaction may be carried out at a temperature of from −10° C. to 100° C., for example at 0° C. rising to room temperature. Batch processes or flow processes are suitable for this transformation.

A compound of formula (XVII) may be prepared by oxidation of 1,3-dibenzylglycerol. In one embodiment, the oxidation may be carried out using 3 A molecular sieves, N-methylmorpholine N-oxide and tetrapropylammonium perruthhenate in dichloromethane at 0° C. to reflux, for example at room temperature. In another embodiment, the oxidation may be carried out using aqueous sodium hypochlorite, saturated sodium bicarbonate solution and 2,2,6,6-tetramethyl-1-piperidinyloxy free radical in toluene at 0° C. to 50° C., for example at room temperature. In a further embodiment, the oxidation may be carried out using sulphur trioxide-pyridine complex in the presence of base such as triethylamine in dimethylsulphoxide at 10° C. to 50° C., for example at room temperature. Batch processes or flow processes are suitable for this oxidation.

A compound of formula (VI) may be prepared by treating a compound of formula (XVIII)

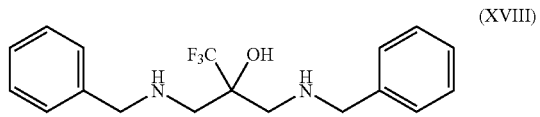

(XVIII)

with a transition metal catalyst, for example palladium hydroxide on carbon, in the presence of a hydrogen atmosphere. The reaction may be carried out in a conventional organic solvent, for example ethanol. The reaction may be carried out at a temperature of from −10° C. to 100° C., for example at room temperature.

A compound of formula (XVIII) may be prepared by treating a compound of formula (IX) as defined above with benzylamine. The reaction may be carried out in a conventional organic solvent, for example 1,4-dioxan. The reaction may be carried out at a temperature of from −10° C. to 100° C., for example at room temperature and then about 100° C.

Alternatively, a compound of formula (I) may be prepared by coupling a compound of formula (V) as defined above with a compound of formula (XIX)

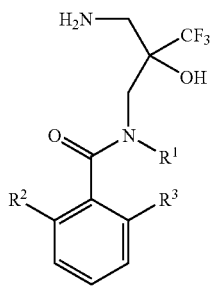

(XIX)

wherein $R^1$, $R^2$ and $R^3$ areas defined above for compounds of formula (I).

This alternative process is particularly suitable for the preparation of compounds of formula (I) wherein $R^2$ and $R^3$ are not chlorine. The reaction may be carried out in a conventional organic solvent, for example dimethylformamide, in the presence of a coupling agent such as those described in Tetrahedron 2005, 61, 10827, for example O-(7-azabenzotriazol-1-yl)-N,N,N',N'-tetramethyluronium hexafluorophosphate (HATU), and a base, for example triethylamine or diisopropylethylamine. In one embodiment, the reaction is carried out in the presence of diisopropylethylamine. The reaction may be carried out at a temperature of from −10° C. to 100° C., for example at room temperature.

Example of acids of formula (V) suitable for use in this coupling reaction include:
5-amino-1-(2-fluorophenyl)-1H-pyrazole-4-carboxylic acid;
5-amino-1-(3-fluorophenyl)-1H-pyrazole-4-carboxylic acid;
5-amino-1-(4-fluorophenyl)-1H-pyrazole-4-carboxylic acid;
5-amino-1-(4-chlorophenyl)-1H-pyrazole-4-carboxylic acid;
5-amino-1-(3-chlorophenyl)-1H-pyrazole-4-carboxylic acid;
5-amino-1-(2-chlorophenyl)-1H-pyrazole-4-carboxylic acid;
5-amino-1-(2,3-difluorophenyl)-1H-pyrazole-4-carboxylic acid;
5-amino-1-(2,4-difluorophenyl)-1H-pyrazole-4-carboxylic acid;
5-amino-1-(2,5-difluorophenyl)-1H-pyrazole-4-carboxylic acid;
5-amino-1-(2,6-difluorophenyl)-1H-pyrazole-4-carboxylic acid;
5-amino-1-(3,4-difluorophenyl)-1H-pyrazole-4-carboxylic acid;
5-amino-1-(3,5-difluorophenyl)-1H-pyrazole-4-carboxylic acid; and
5-amino-1-phenyl-1H-pyrazole-4-carboxylic acid.

Acids of formula (V) may be prepared by, for example, reaction of a suitable aryl hydrazine with ethyl 2-cyano-3-ethoxyacrylate followed by conversion of the resulting ethyl ester to the corresponding acid by treatment with, for example, lithium hydroxide in a solvent such as aqueous ethanol.

A compound of formula (XIX) may be prepared by hydrogenating a compound of formula (XX)

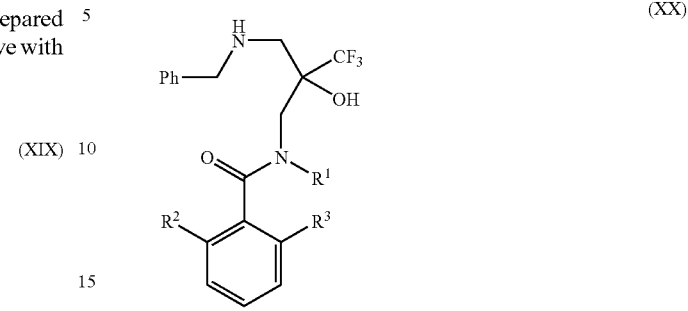

wherein $R^1$, $R^2$ and $R^3$ are as defined above for compounds of formula (I).

The reaction may be carried out in an organic solvent such as ethanol in the presence of an acid such as 2M hydrochloric acid and a catalyst such as palladium hydroxide on carbon. The reaction may be carried out at a temperature of from 0° C. to 60° C., for example at room temperature.

A compound of formula (XX) may be prepared by reaction of benzylamine with an epoxide of formula (XXI).

(XXI)

wherein $R^1$, $R^2$ and $R^3$ are as defined above for compounds of formula (I).

The reaction may be carried out in an organic solvent such as tetrahydrofuran at a temperature of from 0° C. to 65° C., for example at room temperature.

A compound of formula (XXI) may be prepared from a compound of formula (XXII)

(XXII)

wherein $R^1$, $R^2$ and $R^3$ are as defined above for compounds of formula (I), and a compound of formula (IX) as defined above.

The reaction may be carried out in a polar solvent such as tetrahydrofuran, dimethylformamide or dimethoxyethane, preferably dimethoxyethane in the presence of a strong base such as sodium hydride. The reaction may be carried out at a temperature of from −70° C. to +65° C., for example at room temperature.

A compound of formula (XXII) may be prepared by standard methods from the corresponding amine and acid or acid chloride.

Compounds of formula (I) may be prepared in the form of mixtures of enantiomers when mixtures of isomers are used as intermediates in the synthesis. For example, the use of a compound of formula (II) as a racemic mixture of enantiomers will lead to a racemic mixture of enantiomers in the final product. These enantiomers may, if desired, be separated by conventional methods (e.g. HPLC on a chiral column).

Alternatively, separation of enantiomers may be performed earlier in the synthesis, for example individual enantiomers of compounds of formula (II) or earlier stage intermediates. This may obviate the need to perform a separation of enantiomers as a final stage in the synthesis. The later process is, in theory, more efficient and is therefore preferred.

A chiral method of preparing a compound of formula (IV) is shown in Scheme 1:

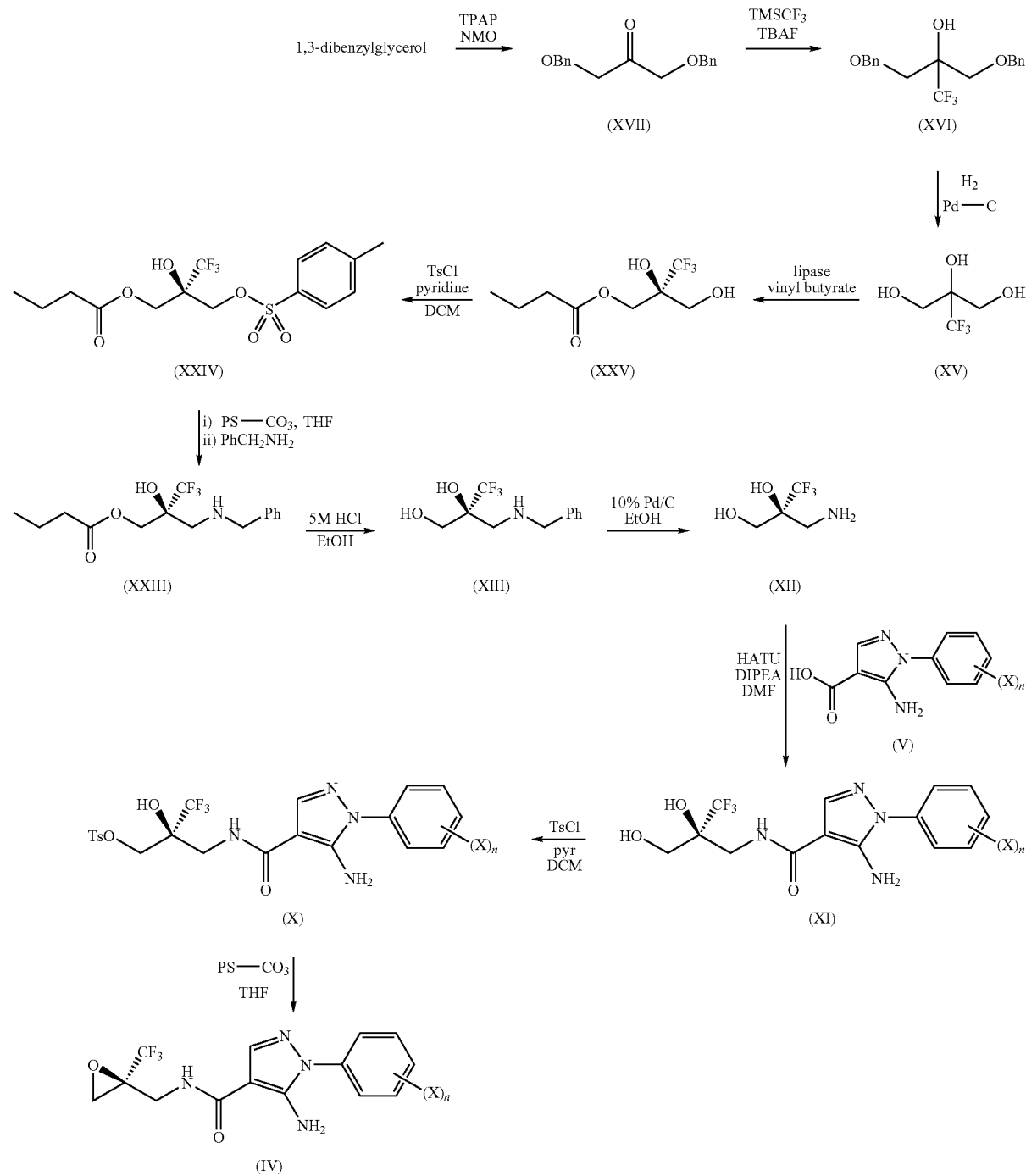

ABBREVIATIONS

| | |
|---|---|
| TPAP | Tetrapropylammonium perruthenate |
| Bn | Benzyl |
| Ph | Phenyl |
| NMO | N-methylmorpholine N-oxide |
| TMSCF$_3$ | Trimethyl(trifluoromethyl)silane |
| TBAF | Tetrabutylammonium fluoride |
| TsCl | P-Toluenesulphonyl chloride |
| DCM | Dichloromethane |
| PS-CO$_3$ | Polymer supported carbonate resin |
| THF | Tetrahydrofuran |
| HCl | Hydrochloric acid |
| EtOH | Ethanol |
| HATU | O-(7-Azabenzotriazol-1-yl)-N,N,N',N'-tetramethyl uranium hexafluorophosphate |
| DIPEA | Diisopropylethylamine |
| DMF | Dimethylformamide |
| pyr | Pyridine |

Certain compounds of formula (II), (IV), (VI), (VII), (VIII), (IX), (X), (XI), (XII), (XIII), (XIV), (XVI), (XVIII), (XIX), (XX) and (XXI) are new and form an aspect of the present invention.

In addition, processes for preparing formulations including one or more compounds of formula (I) form an aspect of this invention.

Compositions comprising a compound of the invention also constitute an aspect of the invention.

Solvates of compounds of formula (I) or salts thereof, which are not pharmaceutically acceptable, may be useful as intermediates in the preparation of other compounds of formula (I), solvates or salts thereof.

The invention will now be illustrated by way of the following non-limiting examples.

EXAMPLES

The following non-limiting Examples illustrate the invention:

General

Abbreviations

| | |
|---|---|
| DMF | dimethylformamide |
| DMSO | dimethyl sulfoxide |
| hr | hours |
| LCMS | liquid chromatography/mass spectrometry |
| MDAP | mass directed autopreparative HPLC |
| Me | methyl |
| MeCN | acetonitrile |
| mins | minutes |
| RT | room temperature |
| SPE | solid phase extraction |
| TFA | trifluoroacetic acid |
| TEMPO | 2,2,6,6,-tetramethyl-1-piperidinyloxy free radical |
| NaOCl | sodium hypochlorite |
| NaHCO$_3$ | sodium bicarbonate |
| Na$_2$S$_2$O$_5$ | sodium metabisulfite |
| HCl | hydrochloric acid |
| MgSO$_4$ | magnesium sulphate |
| AIBN | azo isobutyronitrile |
| THF | tetrahydrofuran |
| TBAF | tetrabutylammonium fluoride |
| EtOAc | ethyl acetate |
| TBME | 1,1-dimethylethyl methyl ether |
| $^t$BuOH | 2-methyl propan-2-ol |

Chromatography

Chromatographic purification was performed using pre-packed Bond Elut silica gel cartridges available commercially from Varian.

The Flashmaster 2 is an automated multi user flash chromatography system which utilises disposable SPE cartridges (2 g to 100 g). It provides quaternary on-line solvent mixing to enable gradient methods to be run. Samples are queued using the multi functional open access software which manages flow rates, gradient profile and collection conditions. The system is equipped with a Knauer variable wavelength uv detector and 2 Gilson FC204 fraction collectors enabling automated peak cutting, collection and tracking.

Mass Directed Autopreparative HPLC (MDAP)

Agilent 1100 series LC/MSD hardware, using electrospray positive mode (ES+ve) running chemstation 32 purification software.

Column: Zorbax Eclipse XDB-C18 prep HT (dimensions 212×100 mm, 5 μm packing), 20 ml/min solvent speed.

Aqueous solvent=Water+0.1% TFA

Organic solvent=MeCN+0.1% TFA

Specific Gradients Used:
Gradient 1 (collects on uv/mass ion trigger)
1 min 70% Water (0.1% TFA): 30% MeCN (0.1% TFA) increasing over 9 mins to 5% Water (0.1% TFA): 95% MeCN (0.1% TFA) to elute compounds.
Gradient 2 (collects on uv only)
1 min 70% Water (0.1% TFA): 30% MeCN (0.1% TFA) increasing over 9 mins to 5% Water (0.1% TFA): 95% MeCN (0.1% TFA) to elute compounds.
CAT MDAP System Column details: Zorbax Eclipse XDB-C18 prep HT (dimensions 212×100 mm, 5 um packing).

Cat_norm method, collects on uv/Mass ion trigger.

Agilent 1100 series LC/MSD hardware, running chemstation 32 purification software.

20 ml/min solvent speed, gradient elution:
1 min 90% water (0.1% TFA):10% MeCN (0.1% TFA) increasing over 9 mins to 5% water (0.1% TFA):95% MeCN (0.1% TFA) to elute compounds.

Cat_gr method, collects on uv/mass ion trigger.
1 min 70% water (0.1% TFA):30% MeCN (0.1% TFA) increasing over 9 mins to 5% water (0.1% TFA):95% MeCN (0.1% TFA) to elute compounds.

Cat_lipo uv method is the same as Cat_gr, collecting on uv only.

LCMS System

The LCMS system used was as follows:
Column: 3.3 cm×4.6 mm ID, 3 μm ABZ+PLUS from Supelco
Flow Rate: 3 ml/min
Injection Volume: 5 μl
Temp: RT
UV Detection Range: 215 to 330 nm
Solvents:
A: 0.1% Formic Acid+10 mMolar Ammonium Acetate.
B: 95% Acetonitrile+0.05% Formic Acid
Gradient:

| Time | A % | B % |
|---|---|---|
| 0.00 | 100 | 0 |
| 0.70 | 100 | 0 |

-continued

| Time | A % | B % |
| --- | --- | --- |
| 4.20 | 0 | 100 |
| 5.30 | 0 | 100 |
| 5.50 | 100 | 0 |

NMR $^1$H NMR spectra were recorded in DMSO-$d_6$ or chloroform-d or MeOD on a Bruker DPX 400, a Bruker AV 400 working at 400 MHz or a Bruker DPX 250 working at 250 MHz. The internal standard used was either tetramethylsilane or the residual protonated solvent at 2.50 ppm for DMSO-$d_6$ or at 7.27 ppm for chloroform-d or at 3.35 ppm for MeOD.

Circular Dichroism

Circular dichroism was carried out on an Applied Photophysics Chirascan spectrophotometer at room temperature, using acetonitrile as solvent, over the range 200-350 nm.

Intermediate 1: 1,3-Bis[(benzyl)oxy]-2-propanone

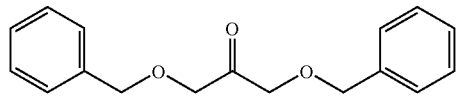

3 A Molecular sieve powder (50 g) was dried at 100° C. in a vacuum oven. The sieves and N-methylmorpholine N-oxide (35.1 g, 300 mmol) were suspended in dry dichloromethane (700 ml) before 1,3-dibenzyloxy-2-propanol (41 ml, 165 mmol) in dichloromethane (100 ml) was added to the stirred suspension. The mixture was stirred under an atmosphere of nitrogen for 90 minutes before tetrapropylammonium perruthenate (3 g, 8.53 mmol) was added. (The reaction was sufficiently exothermic to cause the dichloromethane to boil and therefore a reflux condenser was fitted.) The reaction was stirred at 21° C. for 23 hours before being filtered through celite. It was then washed with 2M hydrochloric acid (400 ml) and saturated brine (500 ml). The combined aqueous washings were filtered through celite and re-extracted with dichloromethane (500 ml) and then this was washed with saturated brine (200 ml). The organic extracts were combined, dried over magnesium sulphate and concentrated under reduced pressure to give a dark oil (43.6 g). Diethyl ether (ca. 200 ml) was added and the resultant black solid was filtered off. The filtrate was concentrated under reduced pressure to give the title compound (42 g) as a grey white solid.

$^1$H NMR (400 MHz, CHLOROFORM-d) δ ppm 7.31-7.40 (m, 10H) 4.59 (s, 4H) 4.26 (s, 4H).

LC-MS Retention Time 3.27 mins, MNH$_4^+$ 288.

Alternative Preparation A of Intermediate 1

A mixture of sodium hypochlorite (100 ml, 13% w/v) and saturated sodium bicarbonate (25 ml) was added in one charge to a stirred solution of 1,3-dibenzyloxy-2-propanol (10 g) and 2,2,6,6-tetramethyl-1-piperidinyloxy free radical, (TEMPO) (0.3 g) in toluene (40 ml). The biphasic mixture was stirred at 20-25° C. for 15 minutes when HPLC analysis showed reaction to be complete. The reaction mixture was stirred for a total of 25 minutes at 23° C. The reaction mixture was separated and the organic extract was washed with 5% w/v sodium thiosulfate solution (40 ml) and separated. The organic extract was washed with 1% w/v sodium chloride solution (2×25 ml). The organic extract was then concentrated in vacuo to give an oil which crystallised on standing to give 8.8 g of 1,3-dibenzyloxy-2-propanone in 88.7% yield. The NMR spectrum of the product was concordant with a reference sample.

Alternative Preparation B of Intermediate 1

A mixture of sulfur trioxide/pyridine complex (2.33 g, 4 equivalents) in DMSO (3 ml) and triethylamine (2.05 ml, 4 equivalents) was stirred to give a pale yellow solution. To this was added a solution of 1,3-dibenzyloxy-2-propanol (1 g) in DMSO (1 ml) over 2 minutes. (The reaction mixture was kept in a water bath). The temperature of the reaction mixture reached 30° C. After 10 minutes the water bath was removed and the reaction mixture was stirred at room temperature (ca 20-25° C.) for 3 hours. The reaction mixture was diluted with ethyl acetate (15 ml) and water (15 ml), stirred and the organic extract was separated. The organic extract was washed with 5% w/v sodium chloride (2×10 ml) and water (10 ml). The separated organic extract was concentrated in vacuo to give an oil which solidified to provide 0.75 g of 1,3-dibenzyloxy-2-propanone in 75.8% yield. An NMR spectrum of product was concordant with a reference sample.

Alternative Preparation C of Intermediate 1

The title compound was prepared via a 'flow' process using the following starting materials and solvents.

The title compound was prepared via a CPC Cytos Lab System made up of a 47 ml reactor block with two Jasco PU—2080 Plus HPLC pumps. Reactor temperature was maintained at 60° C. via a Huber Unistat 360 unit.

Two solutions were prepared. Solution A—1,3-dibenzyloxy-2-propanol (120 g, 440 mmol) in acetonitrile (489 ml). Solution B—tetrapropylammonium perruthenate (7.72 g, 22 mmol, 5 mol %) and N-methylmorpholine N-oxide (87.5 g, 748 mmol) in acetonitrile (611 ml). Solutions A and B were pumped through the Cytos Lab system in the ratio of solution A to solution B of 1:1.25 with a total flow rate of 7.8 ml/min and residence time of 6 minutes. This gave a total reaction time of 2 hours 21 minutes. The total reacted solution was split equally into 2 batches and each was concentrated in vacuo. Diethyl ether (250 ml) was added before being washed with sodium sulphite, brine and cupric sulphate and then filtered through celite, dried and evaporated. The batches were recombined to give upon evaporation in vacuo the title compound (71.64 g).

Alternative Preparation D of Intermediate 1

A solution of 1,3-dibenzyloxy-2-propanol (500 g, 1.84 mol, 1.0 eq.), TEMPO (5.5 g, 0.034 mol) in dichloromethane (1.25 L) was placed in a 10 L flange flask fitted with overhead stirrer. A solution of potassium bromide (48 g, 0.40 mol) in water (185 ml) was added and the reaction stirred and cooled to −10° C. A 14% aqueous NaOCl solution was diluted to 1M (2145 g diluted to 4050 ml). The pH of this solution was then adjusted to 9.5 by dissolving NaHCO$_3$ (80 g) immediately before use. This NaOCl solution was added over 1 hour, keeping the temperature of the reaction mixture between 10-15° C. The mixture was the stirred for 60 minutes. The orange coloured organic phase was separated and the aqueous layer was extracted with dichloromethane (5.0 L, 2.0 L). The combined organics were washed with 10% aq. HCl (10.75 L) containing potassium iodide (143 g), 10% aq. Na$_2$S$_2$O$_5$ (5.0 L) and water (5.0 L). The organics were dried over MgSO$_4$ and concentrated under reduced pressure to give the crude title compound (893 g, 90%). This compound was taken through to the next step without further purification.

Intermediate 2: 1,1,1-Trifluoro-3-[(benzyl)oxy]-2-{[(benzyl)oxy]methyl}-2-propanol

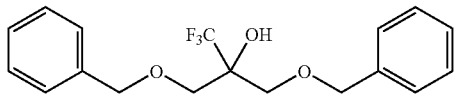

To a solution of 1,3-bis[(benzyl)oxy]-2-propanone (42 g, 155 mmol) in anhydrous tetrahydrofuran (600 ml) was added trimethyl(trifluoromethyl)silane (35 ml, 236 mmol) under nitrogen. The mixture was then cooled in an ice/ethanol bath to −3° C. before tetrabutylammonium fluoride (1M in THF, 180 ml, 180 mmol) was added dropwise (initial 10 ml of addition resulted in a slight exotherm with the temperature rising to 9° C. before being allowed to cool to 6° C. and then the addition was resumed, the temperature dropping to the range of −1° C. to +3° C.). The addition was completed after 30 minutes. The mixture was stirred for a further 4 hours during which, gas was evolved all the time and then 2M hydrochloric acid (750 ml) was added with stirring. Diethyl ether (600 ml) was added and the separated aqueous phase was reextracted with diethyl ether (1×600 ml, 1×300 ml) and the combined organic extracts were washed with saturated brine (1×300 ml), dried over sodium sulphate and concentrated under reduced pressure to give an oil (52.9 g). This oil was purified via flash chromatography (Silica, 800 g) using cyclohexane:ethyl acetate (9:1) as eluent. This gave the title compound as a yellow oil (39.5 g).

$^1$H NMR (400 MHz, CHLOROFORM-d) δ ppm 7.29-7.39 (m, 10H) 4.60 (s, 4H) 3.72 (s, 4H) 3.38 (s, 1H).

LC-MS Retention Time 3.69 mins, MNH$_4^+$ 358.

Alternative Preparation A of Intermediate 2

A mixture of 1,3-dibenzyloxy-2-propanone (2 g) and (trifluoromethyl)trimethylsilane (2.56 ml, 2.3 equivalents) in dichloromethane (20 ml) was stirred and cooled to 0° C. A solution of 1M tetrabutylammonium fluoride in THF (4 ml) was added dropwise over 3 minutes. Initial addition of a few drops gave an exotherm of 10° C. Throughout the addition the batch temperature was maintained below 10° C. After completing the addition the dark brown mixture was stirred at +5° C. for 5 minutes when HPLC analysis indicated the reaction to be complete. The reaction mixture was stirred for an additional 5 minutes and then washed with 1M aqueous hydrochloric acid (15 ml), saturated sodium bicarbonate (15 ml) and 1% w/v aqueous sodium chloride solution (2×15 ml). The organic extract was concentrated in vacuo to give 2.5 g of the desired product as dark oil in 99.3% yield. The NMR spectrum of the product was concordant with a reference sample.

Alternative Preparation B of Intermediate 2

Tetrabutylammonium fluoride trihydrate (TBAF 3H$_2$O) (2.9 g, 0.5 equivalent) was dissolved in THF (5 ml). This was added cautiously to a stirred and cooled (+15° C.) solution of 1,3-dibenzyloxy-2-propanone in toluene (24.65 g, equivalent to 5 g of the ketone) and (trifluoromethyl)trimethylsilane (7.5 ml). There was an exotherm and a lot of gas evolution on addition of the first 1 ml of TBAF solution. The temperature rose from 18 to 40° C. The TBAF addition was carried out over 3 minutes and then the mixture was stirred at 15-30° C. for a further 2 minutes and then cooled to +10° C. while carrying out an HPLC analysis. The reaction mixture was sequentially washed with 1M aqueous hydrochloric acid (50 ml), 1% aqueous sodium chloride solution (2×25 ml) and a mixture of 1% sodium chloride (25 ml) and saturated sodium bicarbonate (5 ml) solution. The separated organic extract was concentrated in vacuo to give 6.41 g of the desired product as dark brown oil in 101.8% yield. The NMR spectrum showed the presence of residual toluene (8.8%) and starting material (ca 3%).

Alternative Preparation C of Intermediate 2

The title compound was prepared via a 'flow' process using the following starting materials and solvents.

The title compound was prepared via a CPC Cytos Lab System made up of a 32 ml reactor block with two Jasco PU—2080 Plus HPLC pumps. Reactor temperature was maintained at 22° C. via a Huber Unistat 360 unit. The reactor outlet was fitted with a 100 psi backflow regulator.

Two solutions were prepared. Solution A—1,3-dibenzyloxy-2-propanone (71.64 g, 265 mmol) and trimethyl(trifluoromethyl)silane (86.7 g, 96 ml, 609.5 mmol) in tetrahydrofuran (99 ml). Solution B—tetrabutylammonium fluoride (0.5M in THF, 265 ml, 132.5 mmol).

Solutions A and B were pumped through the Cytos Lab System with a flow rate of 6.4 ml/min and a 5 minute residence time giving a total reaction time of 82 minutes. The reaction mixture was quenched with 2M hydrochloric acid (560 ml) and then divided into 2 equal batches (2×280 ml). Diethyl ether (100 ml) was added to each batch, extracted and then washed with brine (2×100 ml), dried (MgSO$_4$) and evaporated to give a residue (82.99 g). Part of the residue was taken up in dichloromethane and applied to SPE silica cartridges. Using 10% hexane in dichloromethane as eluent and concentration of the relevant 15 ml fractions, the title compound was obtained. The bulk of the crude sample was purified on the Combiflash Companion XL. 8 g of material was run on a 120 g column with a solvent gradient of 10%-70% dichloromethane in hexane as eluent. Any mixed fractions from each run were combined and repurified in an identical manner. All pure fractions were combined and evaporated to give the title compound (68.68 g).

Alternative Preparation D of Intermediate 2

A solution of 1,3-dibenzyloxy-2-propanone (310 g, 1.15 mol, 1.0 eq.) was placed in a 10 L flange flask, equipped with magnetic stirrer, condenser under argon, followed by THF (3.5 L). This was stirred at 15° C. Trimethyl(trifluoromethyl) silane (TMS-CF$_3$) (Matrix, 231 g, 1.62 mol, 1.41 eq.) was added dropwise over 1 hour. The solution was then cooled to 0° C. using an ice-water bath and tetrabutylammonium fluoride (TBAF) (337 g, 1.29 L, 1M in THF, 1.29 mol, 1.12 eq.) was added dropwise keeping the temperature in the range 0-8° C. (initial sharp delayed exotherms). After the addition was complete, the temperature was raised cautiously to 20° C. and the reaction stirred at 27° C. overnight (oil bath). (TLC Rf starting material=0.3, product=0.4, 80:20 petroleum ether/ethyl acetate showed reaction was essentially complete). Reaction mixture was then cooled to 15° C. using an ice-water bath, then quenched by slow addition of 1M HCl (10.5 L) (transfer to a 20 L separator after 1.0 L added). The mixture was extracted with diethyl ether (3×5.0 L). The combined organics were washed with water (2.5 L) and brine (2.5 L). The organics were dried over MgSO$_4$ and concentrated under reduced pressure to yield a brown oil (388 g with THF).

Intermediate 3:
2-(Trifluoromethyl)-1,2,3-propanetriol

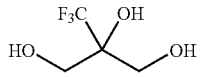

A solution of 1,1,1-trifluoro-3-[(benzyl)oxy]-2-{[(benzyl)oxy]methyl}-2-propanol (98.9 g, 290.9 mmol) in ethanol (1750 ml) was added to 5% palladium on carbon (9.73 g, wet, Degussa, E101 No/W) under nitrogen. The mixture was then stirred under an atmosphere of hydrogen using a Wright valve in a 5 liter hydrogenation vessel. After approximately 3 hours most of the theoretical volume of hydrogen had been taken up. After stirring under hydrogen overnight (approximately a further 1 liter of hydrogen had been taken up overnight), the catalyst was filtered off through a pad of celite and the pad washed with ethanol. The filtrate and washings were then concentrated under reduced pressure and the residue azeotroped (×2) with dichloromethane whereupon the residue became solid. This material was left on the vacuum pump to give the title compound (48.56 g) as an off white solid.

$^1$H NMR (400 MHz, DMSO-d$_6$) δ ppm 5.65 (s, 1H) 4.89 (t, 2H) 3.54 (d, J=5.8 Hz, 4H).

LC-MS Retention Time 0.42 mins, ES$^-$ 159.

Alternative Preparation A of Intermediate 3

The title compound was prepared employing the Thales H-Cube hydrogenator and milligat pump in full hydrogen mode. A solution of 1,1,1-trifluoro-3-[(phenylmethyl)oxy]-2-{[(phenylmethyl)oxy]methyl}-2-propanol (58 g) in ethanol (580 ml) was prepared. The flow rate was 1.3 ml/min, the temperature was set to 80° C. and the cartridge employed was a 10% Pd/C Cat Cart 70 which was replaced every 2 hours. Any fractions which still contained starting material and the mono benzyl intermediate were reprocessed. All pure fractions were combined and evaporated to give the title compound (26.48 g).

Alternative Preparation B of Intermediate 3

1,1,1-Trifluoro-3-[(benzyl)oxy]-2-{[(benzyl)oxy]methyl}-2-propanol (1.3 kg, 3.82 mol, 1.0 eq.) was placed in a 10 L flange flask equipped with a overhead stirrer, followed by ethanol (4.5 L). 10% palladium on carbon (27 g) was added under Argon atmosphere. The reaction was then subjected to hydrogenolysis at atmospheric pressure (6 balloons) and stirred overnight at 50° C. (the balloons were topped up repeatably during the day). $^1$H NMR showed completion of reaction had been reached after 1 week, required additional 10% palladium on carbon (4 g). The reaction mixture was filtered through a pad of celite and washed with ethanol (2.5 L). The filtrate was concentrated under reduced pressure to give an oil. This was placed under high vacuum overnight to obtain a solid material. Toluene (1.5 L) was added and the mixture heated until the solid dissolved (~60° C.), 2 layers were observed. The mixture was stirred using a magnetic stirrer and cooled using an ice-water bath, where a solid precipitated. The solid was broken up and stirred for a further 30 minutes, then isolated by filtration. The solid was washed with toluene (250 ml) and petroleum ether (250 ml). The solid was dried under high vacuum overnight to yield desired product (465 g).

Intermediate 4: 3,3,3-Trifluoro-2-hydroxy-2-({[(4-methylphenyl)sulfonyl]oxy}methyl)propyl 4-methylbenzenesulfonate

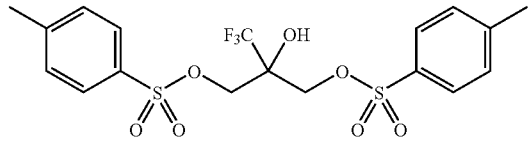

To a stirred solution of 2-(trifluoromethyl)-1,2,3-propanetriol (18.9 g, 118 mmol) in pyridine (200 ml) which had been cooled in an ice bath was added p-toluenesulphonyl chloride (67 g, 351 mmol) to give an orange solution. The ice bath was removed after 45 minutes and stirring was continued for 21 hours during which time a solid formed. Most of the pyridine was removed under reduced pressure and the residue was partitioned between ethyl acetate (500 ml) and water (300 ml). The separated aqueous phase was further extracted with ethyl acetate (1×250 ml) and the combined organic extracts were washed with 2M hydrochloric acid (1×200 ml), water (1×200 ml), saturated sodium bicarbonate (1×200 ml), water (1×200 ml) and saturated brine (1×200 ml) before being dried over sodium sulphate and concentrated under reduced pressure to give an oil (72.8 g). This oil was purified on a Flash silica column (800 g) eluting with cyclohexane:ethyl acetate (5:1) to give the title product (49 g, 95%) as an oil which crystallised on standing.

$^1$H NMR (400 MHz, CHLOROFORM-d) δ ppm 7.78 (d, J=8.3 Hz, 4H) 7.38 (d, J=8.3 Hz, 4H) 4.18 (s, 4H) 3.66 (s, 1H) 2.48 (s, 6H).

LC-MS Retention Time, 3.62 mins, MNH$_4^+$ 486, ES$^-$ 467.

Alternative Preparation A of Intermediate 4

The title compound was prepared via a 'flow' process using the following starting materials and solvents.

Two solutions were prepared. Solution A—2-(trifluoromethyl)-1,2,3-propanetriol (4.5 g, 27.8 mmol), N,N,N',N'-tetramethyl-1,6-hexanediamine (30 ml, 139 mmol), dichloromethane (550 ml). Solution B—p-toluenesulphonyl chloride (21.4 g, 111 mmol), dichloromethane (550 ml).

Solutions A and B were pumped through a CPC Cytos reactor (reactor volume 47 ml) at a flow rate each of 2.35 ml/min. It was noted that the pressure for the pump containing solution B was fluctuating. After 110 minutes, the reaction was abandoned as it was evident that the pumps were not operating 1:1. The collected material was extracted with dichloromethane (×3) before being washed with brine, dried (MgSO$_4$), filtered and concentrated to give a residue which was discarded. The pump was replaced and the remainder of the reagents were reacted. The collected material was extracted with dichloromethane (×3) before being washed with brine, dried (MgSO$_4$), filtered and concentrated to give a residue. It was adsorbed onto silica and eluted over a silica column (12 g) with dichloromethane:hexane (1:1). Four fractions were eluted and fraction 4 gave the title compound (2.31 g).

Alternative Preparation B of Intermediate 4

2-(Trifluoromethyl)-1,2,3-propanetriol (300 g, 1.86 mol, 1.0 eq.) was dissolved in pyridine (2.0 L) in a 10 L flange flask fitted with an overhead stirrer, thermoprobe under argon. This was cooled to 0° C. with a solid CO$_2$-acetone bath. Tosyl chloride (809 g, 4.1 mol, 2.2 eq) was added portionwise, maintaining temperature <10° C. On completion of addition, the cold bath was removed and reaction mixture allowed to stir at room temperature overnight. The reaction mixture was filtered and concentrated under reduced pressure. The resulting brown oil was partitioned between EtOAc (4.0 L) and 2M HCl (4.0 L), stirred for 5 minutes and separated. The aqueous layer was further extracted with EtOAc (2×2.5 L). The combined organics were washed with saturated NaHCO$_3$ (3.5 L, 5 mins stir period), brine (2.5 L) and dried over MgSO$_4$. This was concentrated under reduced pressure to give a thick brown oil. The crude material was taken to the next step without further purification (950 g, overweight, assume 100%).

Intermediate 5:
[2-(Trifluoromethyl)-2-oxiranyl]methyl 4-methylbenzenesulfonate

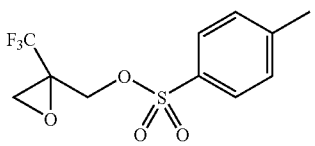

A solution of the 3,3,3-trifluoro-2-hydroxy-2-({[(4-methyl phenyl) sulfonyl]oxy}methyl)propyl 4-methylbenzenesulfonate (186.5 g, 398.5 mmol) in dichloromethane (2500 ml) was stirred under nitrogen whilst polymer supported carbonate resin (ex Fluka, ca. 3.5 mmoles carbonate/g resin) (232 g) was added. The mixture was stirred at room temperature overnight. The resin was filtered off and the resin was washed with dichloromethane. The combined filtrate and washings were concentrated under reduced pressure to give the title compound (116.2 g) as a brown oil.

$^1$H NMR (400 MHz, CHLOROFORM-d) δ ppm 7.80 (d, J=8.3 Hz, 2H) 7.38 (d, J=8.0 Hz, 2H) 4.41 (d, J=11.9 Hz, 1H) 4.29 (d, J=11.9 Hz, 1H) 3.14 (d, J=4.8 Hz, 1H) 3.01 (dd, J=4.5, 1.5 Hz, 1H) 2.47 (s, 3H).

LC-MS Retention Time 3.2 mins, MNH$_4^+$ 314.

Alternative Preparation A of Intermediate 5

3,3,3-Trifluoro-2-hydroxy-2-({[(4-methylphenyl) sulfonyl]oxy}methyl)propyl 4-methylbenzenesulfonate (14.29 g, 29 mmol) in dichloromethane (75 ml) was pumped through a cartridge containing PS-carbonate resin (not pre-swelled) (3 mmol/g, 25 g, 75 mmol) at 675 microliters/min. The temperature was set to approx. 50° C. by wrapping a Whatman thin film heater around the cartridge. The pressure was regulated at 40 psi. After all the reagent had been aspirated, the column was washed through with dichloromethane—at this point the column started to leak slightly and the back pressure regulator had to be removed to reduce the pressure. The collected solution was concentrated in vacuo to afford the title compound (7.25 g).

Alternative Preparation B of Intermediate 5

Bis tosylate, 3,3,3-trifluoro-2-hydroxy-2-({[(4-methylphenyl) sulfonyl]oxy}methyl)propyl 4-methylbenzenesulfonate (1.047 kg, 2.24 mol, 1.0 eq.) was dissolved in dichloromethane (9.0 L) in a 20 L flange flask, fitted with overhead stirrer under argon. Potassium carbonate (1.24 kg, 8.95 mol, 4.0 eq.) was added portionwise over 8 hours and stirred overnight at room temperature. $^1$H NMR showed ~41% completion of reaction. Additional potassium carbonate (600 g, 2.0 eq.) was added over 8 hours and stirred overnight. $^1$H NMR showed 89% completion of reaction. Additional potassium carbonate (300 g, 1.0 eq.) was added over 8 hours and stirred overnight. $^1$H NMR showed completion of reaction reached. The reaction mixture was filtered on two glass sinters with a pad of celite and washed with dichloromethane. The filtrate was washed with NaHCO$_3$ (3.5 L), brine (2.5 L) and dried over MgSO$_4$. The filtrate was then concentrated under reduced pressure to give a dark red oil. The crude product was purified by suction chromatography (~13 cm silica on 4 L sinter, collected ~1.5 L fractions, starting with 95:5 petroleum ether/EtOAc as eluent until all the tosyl chloride was removed, the polarity of the eluent was then increased slowly to 90:10, 80:20 and 70:30. TLC was run with 70:30 Petroleum ether/EtOAc giving Rf tosyl chloride=0.55, Product=0.5, impurity=0.3. Some mixed fractions were obtained, they were re-columned using same conditions as above. This gave clean product (417 g, 63%) as an orange oil, which solidified with high vacuum overnight.

Intermediate 6: 3,3,3-Trifluoro-2-{[(phenylmethyl) amino]methyl}-1,2-propanediol

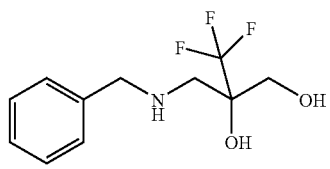

To a stirred solution of the [2-(trifluoromethyl)-2-oxiranyl] methyl 4-methylbenzenesulfonate (10.07 g, 34 mmol) in anhydrous 1,4-dioxan (70 ml) cooled in an ice bath under nitrogen was added benzylamine (4.1 ml, 37.4 mmol) in small portions over 10 minutes. The mixture was stirred at ice bath temperature for a further hour before being allowed to warm to 21° C. and then stirred for 18 hours. 2M Sodium hydroxide (50 ml) and 1,4-dioxan (50 ml) were added and stirred for 2 hours at room temperature before being heated at 90° C. for 22 hours. The mixture was allowed to cool before being concentrated to low volume and partitioned between ethyl acetate (250 ml) and water (100 ml). The separated aqueous layer was further extracted with ethyl acetate (1×250 ml) and the combined organic extracts were washed with water (1×100 ml), saturated brine (1×100 ml), dried over sodium sulphate and concentrated under reduced pressure to give an oil (9.4 g). This was purified on 3×100 g SPE cartridges using a 0-100% cyclohexane-ethyl acetate gradient over 60 mins. This gave upon concentration of the relevant fractions under reduced pressure, the title compound (5.09 g) as an oil.

$^1$H NMR (400 MHz, CHLOROFORM-d) δ ppm 7.30-7.35 (m, 2H) 7.23-7.29 (m, 3H) 3.75-3.86 (m, 4H) 3.57 (d, J=11.6 Hz, 1H) 3.06 (d, J=13.1 Hz, 1H) 2.86 (d, J=13.1 Hz, 1H), OH & NH are very broad 2.5-3.0 ppm.

LC-MS Retention Time 1.45 mins, MH$^+$ 250.

Intermediate 7:
2-(Aminomethyl)-3,3,3-trifluoro-1,2-propanediol

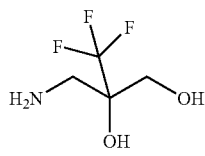

A solution of 3,3,3-trifluoro-2-{[(phenylmethyl)amino]methyl}-1,2-propanediol (8.33 g, 33.4 mmol) in ethanol (550 ml) containing palladium hydroxide on carbon (20%, 800 mg) was stirred under an atmosphere of hydrogen for 24 hours. The catalyst was filtered off via a pad of celite and the filtrate was concentrated under reduced pressure, toluene was added and the solution evaporated again under reduced pressure to give the title compound (5.06 g) as an oil.

$^1$H NMR (400 MHz, MeOD) δ ppm 3.69-3.69 (m, 2H) 2.96 (d, J=13.5 Hz, 1H) 2.87 (d, J=13.5 Hz, 2H).

LC-MS Retention Time 0.32 mins, MH$^+$ 160.

Intermediate 8: Ethyl 5-amino-1-(4-fluorophenyl)-1H-pyrazole-4-carboxylate

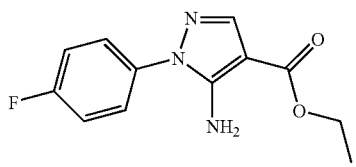

To a stirred suspension of 4-fluorophenylhydrazine hydrochloride (9.76 g, 60 mmol) in ethanol (250 ml) was added triethylamine (9.2 ml, 62 mmol) and to the resulting amber solution was added ethyl 2-cyano-3-ethoxyacrylate (10.15 g, 60 mmol). The solution was heated at reflux temperature for 3.5 hours. The solution was allowed to cool to room temperature and after standing overnight the resultant solid was filtered off, washed with small amount of ethanol and then ether before being dried under vacuum to give the title compound (12.1 g) as an off white solid.

$^1$H NMR (400 MHz, DMSO-d$_6$) δ ppm 7.70 (s, 1H) 7.55 (s, J=5.0 Hz, 2H) 7.34-7.41 (m, 2H) 6.34 (br. s., 2H) 4.21 (q, J=7.0, 7.0 Hz, 2H) 1.26 (t, J=7.0 Hz, 3H).

Intermediate 9: 5-Amino-1-(4-fluorophenyl)-1H-pyrazole-4-carboxylic acid

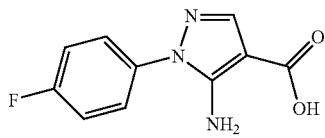

To a suspension of ethyl 5-amino-1-(4-fluorophenyl)-1H-pyrazole-4-carboxylate (12.1 g, 48.5 mmol) in ethanol (250 ml) was added a solution of lithium hydroxide (5.8 g, 242 mmol) in water (100 ml). The mixture was stirred at reflux for 2.5 hours. It was allowed to cool and concentrated to 50% of its volume before 5M hydrochloric acid (47 ml) was added. After stirring for 15 minutes, the resulting white solid was filtered off and further 5M hydrochloric acid (3 ml) was added to the filtrate and the resulting solid was filtered and the combined solids were washed with water and diethyl ether and then dried under vacuum to give the title compound (10.27 g).

$^1$H NMR (400 MHz, DMSO-d$_6$) δ ppm 12.09 (br. s., 1H) 7.67 (s, 1H) 7.54-7.60 (m, 2H) 7.34-7.41 (m, 2H) 6.29 (br. s., 2H).

LC-MS Retention Time 2.20 mins, MH$^+$ 222.

Intermediate 10: 5-Amino-1-(4-fluorophenyl)-N-[3,3,3-trifluoro-2-hydroxy-2-(hydroxymethyl)propyl]-1H-pyrazole-4-carboxamide

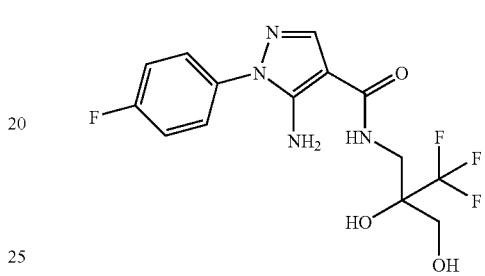

A solution of 5-amino-1-(4-fluorophenyl)-1H-pyrazole-4-carboxylic acid (5.86 g, 26.5 mmol) in anhydrous dimethylformamide (60 ml) and diisopropylethylamine (17.5 ml, 100 mmol) was cooled in an ice bath for 5 minutes before O-(7-azabenzotriazol-1-yl)-N,N,N',N'-tetramethyluronium hexafluorophosphate (HATU) (11.1 g, 29.2 mmol) was added. After 5 minutes, the solution was removed from the ice bath and stirred under nitrogen for 20 minutes. The stirred mixture was recooled in ice for 5 minutes before a solution of the amine, 2-(aminomethyl)-3,3,3-trifluoro-1,2-propanediol (5 g, 31.4 mmol) in anhydrous dimethylformamide (20 ml) was added. The ice bath was again removed and stirring continued for 2.5 hours. The mixture was then partitioned between ethyl acetate (500 ml) and water (500 ml) and the separated aqueous phase was reextracted with ethyl acetate (300 ml). The combined organic extracts were washed with water (1×500 ml, 1×300 ml), 1M hydrochloric acid (1×400 ml), concentrated lithium chloride (2×200 ml), saturated sodium hydrogen carbonate (1×200 ml), water (200 ml) and saturated brine (2×200 ml) before being dried over sodium sulphate and concentrated under vacuum to give a foam (9.5 g). Ethyl acetate (5 ml) was added followed by dichloromethane (50 ml) and the mixture was swirled to initiate crystallisation. It was left to stand in the fridge for 15 hours and the resultant solid was filtered off and washed with small amounts of dichloromethane and then heptane before being dried under vacuum to give the title compound (7.0 g, 73%) as a white solid.

$^1$H NMR (400 MHz, DMSO-d$_6$) δ ppm 8.17 (t, J=6.1 Hz, 1H) 7.99 (s, 1H) 7.54-7.60 (m, 2H) 7.33-7.40 (m, 2H) 6.37 (br. s., 2H) 6.30 (s, 1H) 5.19 (t, J=6.4 Hz, 1H) 3.51-3.69 (m, 2H) 3.38-3.50 (m, 2H).

LC-MS Retention Time 2.20 mins, MH$^+$ 363.

Intermediate 11: 2[({[5-Amino-1-(4-fluorophenyl)-1H-pyrazol-4-yl]carbonyl}amino)methyl]-3,3,3-trifluoro-2-hydroxypropyl 4-methylbenzenesulfonate

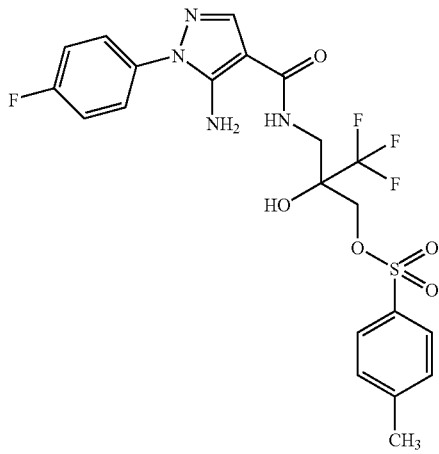

To a stirred solution of 5-amino-1-(4-fluorophenyl)-N-[3,3,3-trifluoro-2-hydroxy-2-(hydroxymethyl)propyl]-1H-pyrazole-4-carboxamide (2.47 g, 6.82 mmol) in anhydrous dichloromethane (20 ml) and anhydrous pyridine (20 ml) cooled in an ice bath under a nitrogen atmosphere was added p-toluenesulphonyl chloride (1.7 g, 8.9 mmol). The mixture was stirred for 6 hours at ice bath temperature before being allowed to warm to room temperature and stirred overnight. The solution was evaporated under vacuum and the residue was partitioned between ethyl acetate (100 ml) and water (30 ml). The separated organic phase was washed with 2M hydrochloric acid (2×30 ml), water (30 ml), saturated sodium hydrogen carbonate (30 ml), water (30 ml) and saturated brine (50 ml) before being dried over sodium sulphate and evaporated under reduced pressure to give a foam (3.45 g). This foam was purified on a Flashmaster column of Silica (100 g) using a 0-100% ethyl acetate in cyclohexane gradient over 1 hour. This afforded the title compound (2.8 g, 79%) as a foam.

$^1$H NMR (400 MHz, DMSO-$d_6$) δ ppm 8.04 (t, J=6.3 Hz, 1H) 7.90 (s, 1H) 7.78 (d, J=8.1 Hz, 2H) 7.55-7.60 (m, 2H) 7.45 (d, J=8.1 Hz, 2H) 7.34-7.41 (m, 2H) 3.97-4.06 (m, 2H) 3.63 (dd, J=14.7, 6.6 Hz, 1H) 3.45 (dd, 1H) 2.38 (s, 3H).

LC-MS Retention Time 3.41 mins, MH$^+$ 517.

Intermediate 12: 5-Amino-1-(4-fluorophenyl)-N-{[2-(trifluoromethyl)-2-oxiranyl]methyl}-1H-pyrazole-4-carboxamide

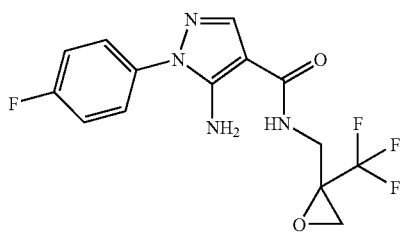

A solution 2-[({[5-amino-1-(4-fluorophenyl)-1H-pyrazol-4-yl]carbonyl}amino)methyl]-3,3,3-trifluoro-2-hydroxypropyl 4-methylbenzenesulfonate (2.8 g, 5.4 mmol) in anhydrous tetrahydrofuran (150 ml) was shaken with polymer supported carbonate resin (ex Fluka, 5 g, 3.5 mmol/g, 17.5 mmol) which had been pre washed with tetrahydrofuran (5×). After shaking for 15 hours, the resin was filtered off and the filtrate was evaporated under reduced pressure to give a semi-solid (1.986 g). Diethyl ether (ca 10 ml) was added and after standing for 3 hours, the resultant crystallised solid (1 g) was filtered off and washed with heptane. The filtrate and precipitate were evaporated under reduced pressure and the residue, dissolved in dichloromethane, was purified on a Flashmaster silica column (100 g) eluting with 0-100% ethyl acetate in cyclohexane over 60 minutes to afford a cream solid (0.46 g). This was combined with the crystallised solid to give the title compound (1.46 g).

$^1$H NMR (400 MHz, DMSO-$d_6$) δ ppm 8.15 (t, J=6.1 Hz, 1H) 7.94 (s, 1H) 7.53-7.60 (m, 2H) 7.36 (t, J=8.8 Hz, 2H) 6.38 (s, 2H) 3.88 (dd, J=14.9, 6.1 Hz, 1H) 3.69 (dd, J=14.8, 6.0 Hz, 1H) 3.17 (d, J=4.3 Hz, 1H) 2.90-2.98 (m, J=4.0 Hz, 1H).

LC-MS Retention Time 2.83 mins, MH$^+$ 345.

Intermediate 13: 1,1,1-Trifluoro-3-[(phenylmethyl)amino]-2-{[(phenylmethyl)amino]methyl}-2-propanol

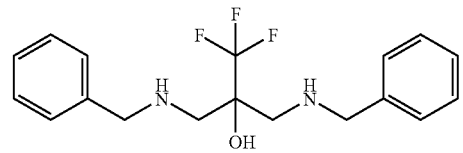

To a solution of [2-(trifluoromethyl)-2-oxiranyl]methyl 4-methylbenzenesulfonate (17.3 g, 58.4 mmol) in anhydrous dioxan (130 ml) stirred, under a nitrogen atmosphere in an ice/water bath, was added benzylamine (8.8 ml, 80 mmol) portionwise over 20 minutes. The cooling bath was removed and the solution was stirred for 23 hours. 2M Sodium hydroxide (90 ml, 180 mmol) and dioxan (70 ml) were added to the suspension and stirred for 1 hour to give a yellow cloudy solution. It was then heated at 100° C. for 23 hours before being concentrated under reduced pressure and the residue partitioned between ethyl acetate (2×250 ml) and water (100 ml). The combined organic extracts were washed with water (100 ml), saturated brine (100 ml), dried over sodium sulphate and concentrated under reduced pressure to give a yellow oil (17 g). This was purified on a Biotage column (800 g) with cyclohexane:ethyl acetate (2:1) as eluent to give the title compound (8.15 g).

$^1$H NMR (400 MHz, MeOD) δ ppm 7.21-7.30 (m, 10H) 3.79 (d, J=13.1 Hz, 2H) 3.73 (d, J=13.1 Hz, 2H) 2.85 (d, J=12.6 Hz, 2H) 2.80 (d, J=12.6 Hz, 2H).

LC-MS Retention Time 2.36 mins, MH$^+$ 339.

Intermediate 14:
3-Amino-2-(aminomethyl)-1,1,1-trifluoro-2-propanol

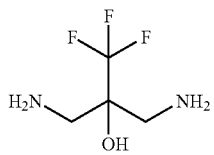

A solution of 1,1,1-trifluoro-3-[(phenylmethyl)amino]-2-{[(phenylmethyl)amino]methyl}-2-propanol (8.15 g, 24.1 mmol) in ethanol (200 ml) was stirred under a hydrogen atmosphere over Pearlman's catalyst (500 mg) for 24 hours. The catalyst was filtered off and the filtrate concentrated under reduced pressure. The residue was redissolved in methanol and concentrated under reduced pressure to give an oil (4.825 g). This oil was redissolved in ethanol (200 ml) and stirred under a hydrogen atmosphere over Pearlman's catalyst (500 mg) for 24 hours. The catalyst was filtered off and the filtrate concentrated under reduced pressure to give the title compound (3.07 g) as an oil.

$^1$H NMR (400 MHz, DMSO-$d_6$) δ ppm 2.68-2.79 (m, 4H).

Intermediate 15: 5-Amino-N-[2-(aminomethyl)-3,3,3-trifluoro-2-hydroxypropyl]-1-(4-fluorophenyl)-1H-pyrazole-4-carboxamide

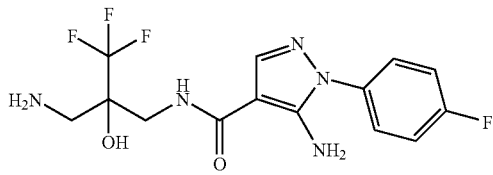

To a solution of 5-amino-1-(4-fluorophenyl)-1H-pyrazole-4-carboxylic acid (1.8 g, 8 mmol) in anhydrous dimethylformamide (30 ml) and diisopropylethylamine (7 ml, 40 mmol) was added O-(7-azabenzotriazol-1-yl)-N,N,N',N'-tetramethyluronium hexafluorophosphate (HATU) (3.34 g, 8.8 mmol). After 20 minutes, a solution of 3-amino-2-(aminomethyl)-1,1,1-trifluoro-2-propanol (1.79 g, 11.3 mmol) in dimethylformamide (5 ml) was added. The mixture was stirred at 21° C. for 15 hours before the solvent was evaporated under reduced pressure and the resulting gum was partitioned between ethyl acetate (150 ml) and water (100 ml). The separated organic phase was washed with water (100 ml), aqueous lithium chloride (50 ml) and saturated brine (100 ml). It was then dried over sodium sulphate and evaporated under reduced pressure to give a glass (5.2 g). This was triturated with dichloromethane (ca. 25 ml) and the solid (2.41 g) was filtered off. This solid was partitioned between ethyl acetate (50 ml) and 2M hydrochloric acid (40 ml) and the separated organic phase washed with water (20 ml). The combined aqueous phases were made alkaline via the addition of solid sodium hydrogen carbonate and then were extracted with ethyl acetate (50 ml). The combined organic phases were washed with water (25 ml), saturated brine (25 ml), dried over sodium sulphate and concentrated under reduced pressure to give the title compound (936 mg) as a white foam.

$^1$H NMR (400 MHz, DMSO-$d_6$) d ppm 8.15 (t, J=6 Hz, 1H), 7.98 (s. 1H) 7.57 (dd, J=9, 5 Hz, 2H) 7.37 (t, J=9 Hz, 2H) 6.39 (s, 2H) 3.61-3.49 (m, 2H) 3.34 (br. s., 2H) 2.83 (d, J=3 Hz, 2H).

LC-MS Retention Time 2.00 mins, MH$^+$ 362.

Alternative Preparation A of Intermediate 15

5-Amino-1-(4-fluorophenyl)-1H-pyrazole-4-carboxylic acid (0.67 g) was dried by co-evaporation of THF/toluene (1:1) followed by high vacuum for 18 hours, 0.67 g became 0.47 g after drying. Thionyl chloride (6 ml) was added to the acid (0.634 g, 2.9 mmol) and the resultant mixture was stirred at room temperature for 2 hours. The mixture was evaporated to dryness then co-evaporated with dichloromethane followed by toluene. 2-(Aminomethyl)-3,3,3-trifluoro-1,2-propanediol (0.47 g) was dissolved in THF (5 ml) and cooled to <5° C. in an ice-bath under an atmosphere of nitrogen. Pyridine (0.47 ml, 0.459 g, 5.8 mmol) was added followed by a solution of the acid chloride in THF (5 ml). The reaction was allowed to warm to room temperature slowly then stirred overnight—total time 20 hours. The reaction mixture was partitioned between ethyl acetate (25 ml) and saturated aqueous sodium hydrogen carbonate (25 ml). The organic phase was washed with aqueous hydrochloric acid (25 ml) followed by saturated aqueous sodium chloride solution. The organic phase was dried (MgSO$_4$), filtered and evaporated. The product was obtained as a pale orange foam (0.86 g).

Alternative Preparation B of Intermediate 15

5-amino-1-(4-fluorophenyl)-N-(3,3,3-trifluoro-2-hydroxy-2-{[(phenylmethyl)amino]methyl}propyl)-1H-pyrazole-4-carboxamide (20.47 g) was dissolved in ethanol (100 ml) and hydrogenated over 10% palladium on carbon (2 g). A small portion was filtered using celite to give an orange yellow solution and LC/MS analysis indicated complete reaction. Therefore the remainder of the suspension was then filtered and the orange yellow solution concentrated in vacuo to give a pale yellow solid. This was dried on the vacuum line overnight to give the title compound (14.64 g) as a white solid.

$^1$H NMR (400 MHz, CHLOROFORM-d) ∂ ppm 7.62 (s, 1H), 7.51 (m, 2H), 7.21 (m, 2H), 6.1 (br. t., 1H), 5.46 (br. s., 2H), 3.85 (dd, 1H), 3.54 (dd, 1H), 3.1 (d, 1H), 2.78 (d, 1H).

LC-MS Retention Time 2.10 mins, MH$^+$ 362.

Intermediate 16: 5-Amino-1-(4-fluorophenyl)-N-{3,3,3-trifluoro-2-hydroxy-2-[(methylamino)methyl]propyl}-1H-pyrazole-4-carboxamide

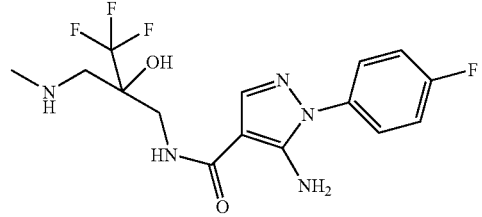

To a solution of 5-amino-1-(4-fluorophenyl)-N-{[2-(trifluoromethyl)-2-oxiranyl]methyl}-1H-pyrazole-4-carboxamide (750 mg, 2.18 mmol) in anhydrous tetrahydrofuran (10 ml) was added methylamine (2M in tetrahydrofuran, 4 ml, 8 mmol) and stirred at 21° C. for 15 hours. It was evaporated to give a foam which was triturated with diethyl ether (ca. 5 ml).

The resulting solid was filtered off and washed with a little diethyl ether and then petroleum ether)(40-60° to give the title compound (465 mg).

¹H NMR (400 MHz, CHLOROFORM-d) δ ppm 7.62 (s, 1H) 7.50-7.57 (m, 2H) 7.19-7.25 (m, 2H) 6.11-6.21 (m, 1H) 5.46 (s, 2H) 3.85 (dd, J=14.4, 7.7 Hz, 1H) 3.56 (dd, J=14.3, 5.0 Hz, 1H) 3.03 (d, J=13.3 Hz, 1H) 2.62 (d, J=13.1 Hz, 1H) 2.45-2.51 (m, 3H).

LC-MS Retention Time 1.79 mins, MH⁺ 376.

Intermediate 17: 5-Amino-N-{2-[(ethylamino)methyl]-3,3,3-trifluoro-2-hydroxypropyl}-1-(4-fluorophenyl)-1H-pyrazole-4-carboxamide

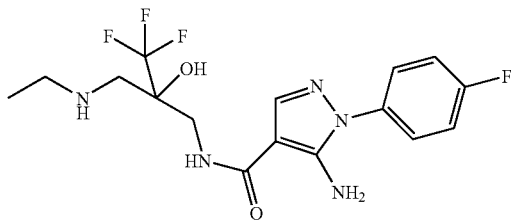

To a solution of 5-amino-1-(4-fluorophenyl)-N-{[2-(trifluoromethyl)-2-oxiranyl]methyl}-1H-pyrazole-4-carb oxamide (2 g, 5.8 mmol) in acetonitrile (25 ml) was added ethylamine (5 ml, 23 mmol). The solution was stirred at room temperature for 24 hours under nitrogen before further ethylamine (2 ml) was added. The solution was concentrated under reduced pressure to give the title compound (2.290 g).

¹H NMR (400 MHz, CHLOROFORM-d) δ ppm 7.64 (s, 1H) 7.50-7.56 (m, 2H) 7.19-7.25 (m, 2H) 6.29 (br. s., 1H) 5.46 (s, 2H) 3.83 (dd, J=14.4, 7.6 Hz, 1H) 3.60 (dd, J=14.3, 4.7 Hz, 1H) 3.08 (d, J=13.4 Hz, 1H) 2.63-2.84 (m, 3H) 1.13 (t, 3H).

LC-MS Retention Time 2.06 mins, MH⁺ 390.

Alternative Preparation A of Intermediate 17

A solution of 5-amino-N-(2-{[ethyl(phenylmethyl)amino]methyl}-3,3,3-trifluoro-2-hydroxypropyl)-1-(4-fluorophenyl)-1H-pyrazole-4-carboxamide (0.39 g, 0.813 mmol) in ethanol (35 ml) was stirred under an atmosphere of hydrogen over Pearlman's catalyst (45 mg) for 7 hours (32 ml of hydrogen taken up). The catalyst was filtered off and the filtrate was evaporated to give the title compound (0.313 g) as a white solid.

¹H NMR (400 MHz, DMSO-d₆) δ ppm 8.10 (t, 1H) 7.94 (s, 1H) 7.54-7.61 (m, 2H) 7.33-7.40 (m, 2H) 6.37 (br. s., 2H) 3.65 (dd, J=6.3 Hz, 1H) 3.46 (dd, J=14.0, 5.7 Hz, 1H) 2.72 (dd, J=5.6 Hz, 2H) 2.52-2.62 (m, 2H) 1.01 (t, J=7.1 Hz, 3H).

LC-MS Retention Time 2.00 mins, MH⁺ 390.

Intermediate 18: 3-Amino-2-{[ethyl(phenylmethyl)amino]methyl}-1,1,1-trifluoro-2-propanol

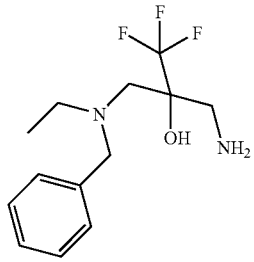

To a solution of [2-(trifluoromethyl)-2-oxiranyl]methyl 4-methylbenzenesulfonate (4.15 g, 14 mmol) in anhydrous dioxan (35 ml) was added N-ethyl benzylamine (2.4 ml, 16.1 mmol). The mixture was stirred under nitrogen at 21° C. for 24 hours. 0.5M Ammonia in dioxan (200 ml, 100 mmol) was added, stirred for 30 minutes and then heated at 100° C. for 24 hours. It was allowed to cool, the solid filtered off and the filtrate evaporated under reduced pressure to give a residue (4.7 g). This was purified on Flashmaster (3×100 g silica cartridges) using a gradient of 0-25% methanol in dichloromethane over 60 minutes to give the title compound (2.64 g) as an oil.

¹H NMR (400 MHz, DMSO-d₆) δ ppm 7.17-7.38 (m, 5H) 3.84 (d, J=13.8 Hz, 1H) 3.56 (d, J=13.8 Hz, 1H) 2.79 (s, 2H) 2.62-2.76 (m, 2H) 2.53-2.61 (m, 1H) 2.38-2.48 (m, J=13.4, 6.9, 6.8 Hz, 1H) 0.94 (t, J=7.0 Hz, 3H).

LC-MS Retention Time 2.18 mins, MH⁺ 277.

Intermediate 19: 5-Amino-N-(2-{[ethyl(phenylmethyl)amino]methyl}-3,3,3-trifluoro-2-hydroxypropyl)-1-(4-fluorophenyl)-1H-pyrazole-4-carboxamide

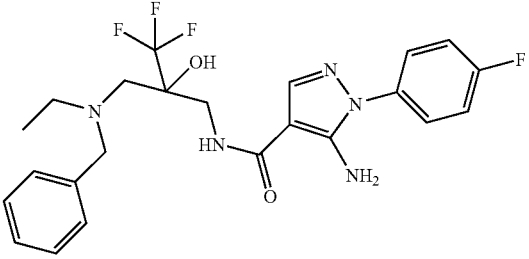

Diisopropylethylamine (0.175 ml, 1 mmol) was added to a mixture of 5-amino-1-(4-fluorophenyl)-1H-pyrazole-4-carboxylic acid (0.119 g, 0.54 mmol) and 0-(7-azabenzotriazol-1-yl)-N,N,N',N'-tetramethyluronium hexafluorophosphate (HATU) (0.205 g, 0.54 mmol) in dimethylformamide (1 ml). The resultant mixture was stirred at room temperature for 20 minutes, then a solution of 3-amino-2-{[ethyl(phenylmethyl)amino]methyl}-1,1,1-trifluoro-2-propanol (0.296 g, 1.07 mmol) in dimethylformamide (1 ml) was added. The reaction mixture was stirred at room temperature for 4 hours. The reaction mixture was partitioned between ethyl acetate (30 ml) and water (30 ml) and the separated organic phase washed with saturated aqueous sodium chloride solution, dried over magnesium sulphate, filtered and evaporated under reduced pressure. The residue was purified by chromatography on silica (10 g) using 0-100% ethyl acetate in cyclohexane gradient over 15 minutes to give the title compound (0.39 g).

¹H NMR (400 MHz, CHLOROFORM-d) δ ppm 7.50-7.55 (m, 2H) 7.49 (s, 1H) 7.25-7.36 (m, 5H) 7.19-7.24 (m, 2H) 5.83-5.89 (m, 1H) 5.71 (br. s., 1H) 5.46 (br. s., 2H) 3.78-3.87 (m, 2H) 3.63 (d, J=13.4 Hz, 1H) 3.48 (dd, J=14.1, 4.5 Hz, 1H) 2.98 (d, J=14.9 Hz, 1H) 2.77 (d, J=15.2 Hz, 1H) 2.56-2.72 (m, 2H) 1.06 (t, J=7.1 Hz, 3H).

LC-MS Retention Time 2.58 mins, MH⁺ 480.

Intermediate 20: (S)-3,3,3-Trifluoro-2-hydroxy-2-(hydroxymethyl)Propyl butanoate

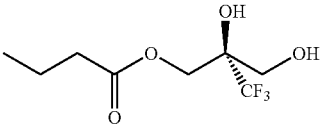

Preparation of Lipase Amano PS Precipitate

Amano PS (available from Amano Enzymes) (10 g) was suspended in water (30 ml) and filtered through a Varian bond elute filter tube, washing with water (20 ml). After precipitation with propan-2-ol (200 ml), the suspension was allowed to settle and the supernatant decanted to leave a 50 ml volume of suspension that was centrifuged at 4000 rpm for 5 minutes and the supernatant decanted to leave the title compound.

Lipase Catalysed Desymmetrisation using Amano PS Precipitate

Vinyl butyrate (1 ml) was added to a stirred mixture of 4 Å molecular sieves (2 g), lipase Amano PS precipitate (100 mg) and 2-(trifluoromethyl)-1,2,3-propanetriol (1 g) suspended in 1,1-dimethylethyl methyl ether (10 ml) and the mixture stirred at room temperature. The mixture was filtered through celite after 21.5 hours, washing with dichloromethane, concentrated, diluted with toluene (20 ml) and washed with saturated aqueous sodium chloride (2×20 ml), dried ($Na_2SO_4$) and evaporated to give a light yellow oil. $^{19}$F NMR spectroscopy displayed a 20:1 mixture of monoester/diester with no starting triol. The yellow oil was purified by chromatography over silica using a 1:1 mixture of dichloromethane/cyclohexane as eluent to remove the side products followed by elution with dichloromethane/ethyl acetate to afford the title compound as a pale yellow oil (0.64 g).

$^1$H NMR (400 MHz, CHLOROFORM-d) δ ppm 4.45 (d, 1H) 4.35 (d, 1H) 3.85 (dd, 1H) 3.73 (dd, 1H) 2.37 (t, 2H) 1.64-1.74 (m, 2H) 0.98 (t, 3H).

Enantiomeric Excess Determination (R)-(−)-α-Methoxy-α-trifluoromethylphenylacetyl chloride (45 µl) and (S)-(+)-α-methoxy-α-trifluoromethylphenylacetyl chloride (45 µl) were added to two parallel reactions containing mixtures of the title compound (20 mg) in pyridine (22 µl) and dichloromethane (1 ml) and the resultant mixtures stirred at room temperature. After 1 hour, the mixtures were washed with a saturated aqueous solution of sodium bicarbonate (1 ml) then a 2M aqueous solution of HCl (1 ml) and finally water (1 ml) and the organic portions concentrated and the crude mixtures analysed by $^{19}$F NMR from which the title compound was found to have an enantiomeric excess of 88% and 86% respectively.

Alternative Preparation A of Intermediate 20

Preparation of Amano PS Solution

Amano lipase PS (100 g) was suspended in 1M pH 7 potassium phosphate solution (400 ml) and filtered, washing the cake with further buffer solution (100 ml) to give a yellow/brown solution as the filtrate.

Immobilisation of Amano PS onto Sepabeads

Amano PS solution (100 ml) was added to sepabeads EC-EP (available from Mitzubishi-Resindion) (40 g) and the mixture shaken at room temperature. After 23 hours as much liquid as possible was removed by pipette and the liquid replaced by an equal volume of a 1M pH10 potassium phosphate solution and shaking continued. After 92 hours the mixture was filtered and the residue washed with water (3×50 ml), suspended in a saturated solution of octadecylamine in toluene (50 ml) and shaken at room temperature for a further 25 hours. The mixture was filtered, washed with toluene (2×100 ml) and acetone (25 ml) and left under suction to afford a free flowing powder. The immobilised enzyme was obtained as pale brown beads (17.29 g).

Lipase Catalysed Desymmetrisation using Amano PS on Sepabeads

In parallel reactions, a mixture of 2-(trifluoromethyl)-1,2,3-propanetriol (100 mg), Amano PS onto Sepabeads (100 mg), vinyl butyrate (0.3 ml) and solvent (as shown in table 1 below) (1 ml) was shaken at room temperature. The reactions were analysed by $^{19}$F NMR after 42 hours to give 2-(trifluoromethyl)-1,2,3-propanetriol (triol)/title compound/2-[(butanoyloxy)methyl]-3,3,3-trifluoro-2-hydroxypropyl butanoate (diester) peak ratios shown in table 1 below.

TABLE 1

| | | | | | Composition after 42 hours ($^{19}$F NMR - % peak area) | | |
|---|---|---|---|---|---|---|---|
| Entry | Triol/mg | Catalyst/mg | Vinyl butyrate/ml | Solvent/ 1 ml | Diester | Title compound | Triol starting material |
| 1* | 100 | 100 | 0.3 | TBME | 3 | 47 | 39 |
| 2 | 100 | 100 | 0.3 | TBME | 4 | 80 | 16 |
| 3 | 100 | 100 | 0.3 | THF | Not run | 47 | 53 |
| 4 | 100 | 100 | 0.3 | Toluene | 16 | 4 | 78 |
| 5 | 100 | 100 | 0.3 | $^t$BuOH | 1 | 47 | 53 |
| 6 | 100 | 100 | 0.3 | MeCN | 3 | 28 | 69 |

*10 beads of 4 Å molecular sieves were also added at the start of the reaction.

Enantiomeric Excess Determination

To parallel reactions, (R)-(−)-α-methoxy-α-trifluoromethylphenylacetyl chloride (45 µl) was added to mixtures of crude title compound (20 mg) in pyridine (22 µl) and dichloromethane (1 ml) and the resultant mixtures were stirred at room temperature. After 1 hour, the mixtures were washed with 2M HCl (1 ml), separated and the organic portions washed with a saturated aqueous solution of sodium bicarbonate (1 ml), the organic portions were then concentrated under a stream of nitrogen and analysed by $^{19}$F NMR from which the title compound enantiomeric excesses were obtained.

TABLE 2

| Reaction | % ee ($^{19}$F NMR) |
|---|---|
| 1 | 61 |
| 2 | 74 |
| 3 | 55 |
| 4 | Not tested |
| 5 | 52 |
| 6 | 32 |

Alternative Preparation B of Intermediate 20

A 10 g/L solution of 2-(trifluoromethyl)-1,2,3-propanetriol in vinyl butyrate/TBME (1:9) was prepared and passed through an Omnifit column (10 cm×0.6 cm) for Entries 1-3 and 2 parallel Omnifit columns (10 cm×1.2 cm) for Entries 4 and 5, all packed to full capacity with lipase Amano PS on sepabeads at room temperature using an HPLC pump and a pulse damper fitted after the column. The column was allowed to equilibrate for 1 hour on changing the conditions for each Entry before sampling (about 5 ml samples taken) from the column outlet. Each sample taken was evaporated and analysed by $^{19}$F NMR.

TABLE 3

| Entry | [Triol] g/dm$^{-3}$ | Column size/cm | N° of parallel columns | Flow rate/ cm$^3$min$^{-1}$ | TLC appearance | Composition (19F NMR - % Peak Area) | | |
|---|---|---|---|---|---|---|---|---|
| | | | | | | Diester | Monoester (title compound) | Triol |
| 1 | 10 | 10 × 0.6 | 1 | 0.5 | <50% monoester | 2 | 32 | 42 |
| 2 | 10 | 10 × 0.6 | 1 | 0.2 | >50% monoester | 4 | 69 | 28 |
| 3 | 1 | 10 × 0.6 | 1 | 0.5 | ~50% monoester | 4 | 46 | 50 |
| 4 | 10 | 10 × 1.2 | 2 | 0.5 | Monoester only | 2 | 89 | 7 |
| 5 | 10 | 10 × 1.2 | 2 | 1 | Monoester + trace of diester | 2 | 63 | 35 |

Enantiomeric Excess Determination (R)-(−)-α-Methoxy-α-trifluoromethylphenylacetyl chloride (40 μl) or (S)-(+)-α-methoxy-α-trifluoromethylphenylacetyl chloride was added to parallel reactions containing mixtures of monoesters (20 mg) shown in Table 4 below in pyridine (20 μl) and dichloromethane (1 ml) and the resultant mixtures stirred at room temperature. After 1 hour the mixtures were washed with a 2M aqueous solution of HCl (1 ml) then a saturated aqueous solution of sodium bicarbonate (1 ml), the organic portions were concentrated and the crude mixtures analysed by $^{19}$F NMR from which the title compound enantiomeric excesses were obtained.

TABLE 4

| Entry | % ee ($^{19}$F NMR) |
|---|---|
| 1 | 74 |
| 2 | 70 |
| 3 | Not tested |
| 4 | 78 |
| 5 | 67 |
| 1A | 72 |
| 5A | 66 |

*Samples 1A, 5 and 5A were reacted with (S)-(+)-α-methoxy-α-trifluoromethylphenylacetyl chloride.

Intermediate 21: (R)-3,3,3-Trifluoro-2-hydroxy-2-({[(4-methylphenyl)sulfonyl]oxy}methyl)propyl butanoate

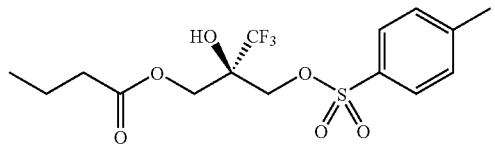

(S)-3,3,3-trifluoro-2-hydroxy-2-(hydroxymethyl)propyl butanoate (372 mg) was dissolved in dry dichloromethane (4 ml) and dry pyridine (3 ml) and cooled in an ice bath under nitrogen. P-Toluenesulphonyl chloride (0.4 g) was added and the reaction was stirred at ice bath temperature for 1 hour and then at room temperature overnight. The reaction was left stirring at room temperature under nitrogen for a further 2 days. The solvent was evaporated and the residue was partitioned between ethyl acetate and water. The organic layer was washed with 1M hydrochloric acid, water, sodium bicarbonate, brine, dried using a hydrophobic frit and evaporated to give an orange oil (0.68 g). This was dissolved in dichloromethane and applied to a 50 g SPE cartridge and eluted with dichloromethane followed by 10% methanol in dichloromethane. The relevant fractions were combined and evaporated to give the title compound as a pale yellow oil (0.36 g).

$^1$H NMR (400 MHz, CHLOROFORM-d) ∂ ppm 7.82 (d, 2H) 7.39 (d, 2H) 4.32-4.41 (m, 2H) 4.16-4.22 (m, 2H) 3.68-3.69 (m, 1H) 2.48 (s, 3H) 2.34 (t, 2H) 1.60-1.69 (m, 2H) 0.95 (t, 3H).

LC-MS Retention Time 3.33 mins, MNH$_4^+$ 402.

Four further fractions which contained product by TLC (eluted with 10% MeOH/DCM) were combined and evaporated to give an orange oil (0.39 g) which was dissolved in DCM and applied to a 20 g SPE column and purified on the Flashmaster eluting with a 0-50% ethyl acetate/cyclohexane 20 minute gradient. The fractions containing the product were evaporated to give a colourless oil (0.3 g). Total yield (0.66 g).

LC-MS Retention Time 3.48 mins, MNH$_4^+$ 402.

Intermediate 22: (S)-3,3,3-Trifluoro-2-hydroxy-2-{[(phenylmethyl)amino]methyl}propyl butanoate

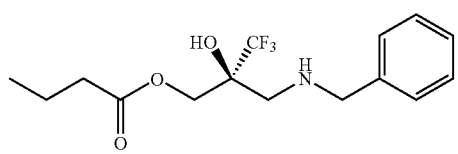

Polymer Supported Carbonate Resin (ex Fluka, 3.5 mmol/g, 0.96 g) was washed thoroughly with dry tetrahydrofuran (5 times). (R)-3,3,3-trifluoro-2-hydroxy-2-({[(4-methylphenyl)sulfonyl]oxy}methyl)propyl butanoate (0.43 g) was dissolved in dry tetrahydrofuran (5 ml) and shaken with the polymer supported carbonate overnight.

The resin was filtered off and the reaction solution was treated with benzylamine (122 μl). The reaction was stirred at room temperature under nitrogen, overnight. A further portion of benzylamine (24 μl) was added and the reaction was stirred at room temperature for 2 hours. The solvent was evaporated to give the title compound as a colourless liquid (0.38 g).

$^1$H NMR (400 MHz, CHLOROFORM-d) ∂ ppm 7.27-7.38 (m, 5H) 4.28-4.32 (m, 1H) 4.16-4.20 (m, 1H) 3.82-3.92 (m, 4H) 3.01-3.06 (m, 1H) 2.71-2.77 (m, 1H) 2.28-2.32 (m, 2H) 1.60-1.69 (m, 2H) 0.91-0.99 (m, 3H).

LC-MS Retention Time 2.72 mins, MH$^+$ 320.

Intermediate 23: (S)-3,3,3-Trifluoro-2-{[(phenylmethyl)amino]methyl}-1,2-propanediol

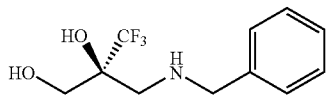

(S)-3,3,3-Trifluoro-2-hydroxy-2-{[(phenylmethyl)amino]methyl}propyl butanoate (0.32 g) was dissolved in 5M hydrochloric acid (5 ml) and ethanol (5 ml) and heated at 100° C. for 3 hours. After cooling, the ethanol was evaporated and the remaining aqueous was basified with 2M sodium hydroxide and extracted with ethyl acetate (2 times). The combined organics were dried using a hydrophobic frit and evaporated to give the title compound as a pale yellow oil (0.26 g).

$^1$H NMR (400 MHz, CHLOROFORM-d) ∂ ppm 7.28-7.40 (m, 5H) 3.82-3.91 (m, 3H) 3.61 (d, 1H) 3.52 (s, 1H) 3.12 (d, 1H) 2.91 (d, 1H).

LC-MS Retention Time 1.65 mins, MH$^+$ 250.

Intermediate 24: (S)-2-(Aminomethyl)-3,3,3-trifluoro-1,2-propanediol

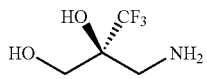

(S)-3,3,3-Trifluoro-2-{[(phenylmethyl)amino]methyl}-1,2-propanediol (160 mg) was dissolved in methanol (1.5 ml) and hydrogenated using 10% palladium on carbon as the catalyst and the H-cube (Thales) as the hydrogen source. The solvent was carefully evaporated to give a pinkish volatile oil (112 mg) which by $^1$H NMR still contained 13% starting material. Therefore this was re-dissolved in methanol (2 ml) and re-hydrogenated using the H-cube. The solvent was evaporated to give the title compound as a pink/brown oil (93 mg).

$^1$H NMR (400 MHz, CHLOROFORM-d) ∂ ppm 3.85 (d, 1H) 3.57 (d, 1H) 3.50 (s, 4H) 3.15 (s, 1H) 2.98 (d, 1H).

LC-MS Retention Time 0.41 mins, MH$^+$ 160.

Intermediate 25: (S)-5-Amino-1-(4-fluorophenyl)-N-[3,3,3-trifluoro-2-hydroxy-2-(hydroxymethyl)propyl]-1H-pyrazole-4-carboxamide

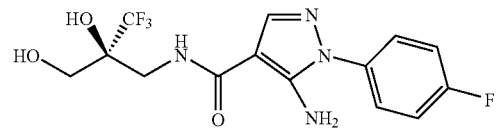

5-Amino-1-(4-fluorophenyl)-1H-pyrazole-4-carboxylic acid (104 mg) was dissolved in dry dimethylformamide (3 ml) and diisopropylethylamine (0.33 ml) was added followed by the addition of O-(7-Azabenzotriazol-1-yl)-N,N,N',N'-tetramethyl uronium hexafluorophosphate (196 mg). The reaction was stirred at room temperature, under nitrogen, for 20 minutes. (S)-2-(Aminomethyl)-3,3,3-trifluoro-1,2-propanediol (90 mg) in dry dimethylformamide (2 ml) was added and the reaction was stirred at room temperature for 3 hours. The reaction was partitioned between ethyl acetate (50 ml) and water (50 ml) and the separated aqueous phase was re-extracted with ethyl acetate (50 ml). The combined organics were washed with water, 1M hydrochloric acid, 10% lithium chloride solution (2 times), bicarbonate and brine. The organics were dried using a hydrophobic frit and evaporated to give a pale yellow oil (200 mg). This was dissolved in dichloromethane (ca. 5 ml) and left to stand at room temperature for 4 hours wherein a precipitate formed. The precipitate was filtered and washed with a small amount of dichloromethane to give the title compound as a white solid (93 mg).

$^1$H NMR (400 MHz, DMSO-d$_6$) δ ppm 8.15-8.22 (m, 1H) 8.01 (s, 1H) 7.55-7.60 (m, 2H) 7.34-7.40 (m, 2H) 5.76 (s, 2H) 5.17-5.21 (m, 1H) 3.40-3.68 (m, 4H).

LC-MS Retention Time 2.47 mins, MH$^+$ 363.

The filtrate from above was evaporated and the residue was dissolved in DMSO/MeOH (1 ml 1:1) and purified on the MDAP. Fractions containing product were combined and evaporated to give the title compound as a colourless oil (28 mg) (total yield 121 mg)

$^1$H NMR showed pure product.

LC/MS Retention Time 2.51 mins, MH$^+$ 363.

Intermediate 26: (S)-2-[({[5-Amino-1-(4-fluorophenyl)-1H-pyrazol-4-yl]carbonyl}amino)methyl]-3,3,3-trifluoro-2-hydroxypropyl 4-methylbenzenesulfonate

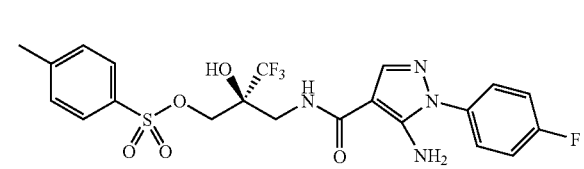

(S)-5-Amino-1-(4-fluorophenyl)-N-[3,3,3-trifluoro-2-hydroxy-2-(hydroxymethyl)propyl]-1H-pyrazole-4-carboxamide (90 mg) was dissolved in dry dichloromethane (3 ml) and dry pyridine (3 ml) and cooled in an ice bath under nitrogen. p-Toluenesulphonyl chloride (62 mg) was added and the reaction was stirred at ice bath temperature for 1 hour and then at room temperature for 24 hours. p-Toluenesulphonyl chloride (25 mg) was added and the reaction was stirred at room temperature, under nitrogen over the weekend. p-Toluenesulphonyl chloride (25 mg) was added and the reaction was stirred at room temperature under nitrogen for 2 hours and heated at 50° C. for 2 hours and left stirring at room temperature overnight. The solvent was evaporated and the residue was partitioned between dichloromethane and water. The organic layer was washed with 1M hydrochloric acid, water, sodium bicarbonate and brine, dried using a hydrophobic frit and evaporated to give a beige foam (94 mg). This was dissolved in dichloromethane and applied to a 10 g SPE cartridge and purified on the Flashmaster eluting with a 0-50% ethyl acetate in cyclohexane over a 20 minute gradient. The appropriate fraction was evaporated to give the title compound as a colourless oil (83 mg).

$^1$H NMR (400 MHz, CHLOROFORM-d) ∂ ppm 7.79-7.83 (m, 2H) 7.71 (s, 1H) 7.50-7.55 (m, 2H) 7.37-7.41 (m, 2H) 7.20-7.26 (m, 2H) 6.60-6.68 (m, 1H) 6.56 (s, 1H) 5.46 (s, 2H) 4.17-4.24 (m, 1H) 3.98-4.07 (m, 1H) 3.60-3.70 (m, 1H) 3.45-3.55 (m, 1H) 2.47 (s, 3H).

LC-MS Retention Time 3.33 mins, MH$^+$ 517.

Intermediate 27: (S)-5-Amino-1-(4-fluorophenyl)-N-{[2-(trifluoromethyl)-2-oxiranyl]methyl}-1H-pyrazole-4-carboxamide

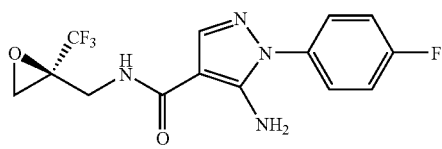

Polymer Supported carbonate resin (3.5 mmol/g, 137 mg) was washed thoroughly with dry tetrahydrofuran (5 times). (S)-2-[({[5-amino-1-(4-fluorophenyl)-1H-pyrazol-4-yl]carbonyl}amino)methyl]-3,3,3-trifluoro-2-hydroxypropyl 4-methyl benzene sulfonate (83 mg) was dissolved in dry tetrahydrofuran (5 ml) and shaken with the polymer supported resin overnight. The resin was filtered off and the solution was evaporated to give the title compound as a beige solid (60 mg).

$^1$H NMR (400 MHz, CHLOROFORM-d) ∂ ppm 7.60 (s, 1H) 7.50-7.55 (m, 2H) 7.19-7.25 (m, 2H) 5.73 (br. s., 1H) 5.47 (br. s., 2H) 4.21-4.31 (m, 1H) 3.73-3.78 (m, 1H) 3.13 (d, 1H) 2.95-2.98 (m, 1H).

LC-MS Retention Time 2.84 mins, MH$^+$ 345.

Intermediate 28:
1-Chloro-3-[(difluoromethyl)oxy]-2-methylbenzene

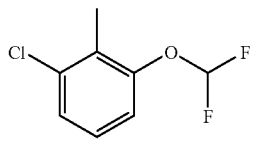

Difluorochloromethane was bubbled into a stirred mixture of 3-chloro-2-methyl phenol (5 g), sodium hydroxide (4.8 g) and tetraethylammonium bromide (0.92 g) in dioxane:water (100 ml:10 ml) heated at 75-80° C. An initial exotherm was noted which ceased after ca. 10 minutes, a white precipitate was also observed. After ca. 15 minutes, the addition of difluorochloromethane was stopped and the reaction mixture allowed to cool to room temperature. The reaction mixture was partitioned between ether (200 ml) and water (200 ml). The organic phase was washed with saturated aqueous sodium chloride solution, dried (MgSO$_4$), filtered and evaporated. The residue was purified by chromatography on silica (100 g cartridge) eluting with 0-50% ethyl acetate in cyclohexane over 40 minutes. Appropriate fractions were combined and evaporated to give the title compound as a colourless oil.

$^1$H NMR (400 MHz, CHLOROFORM-d) ∂ ppm 7.28 (d, 1H), 7.16 (t, 1H), 7.05 (d, 1H), 6.53 (t, 1H, J=75 Hz), 2.38 (s, 3H).

LC-MS Retention Time 3.59 mins.

Intermediate 29:
2-Chloro-6-[(difluoromethyl)oxy]benzoic acid

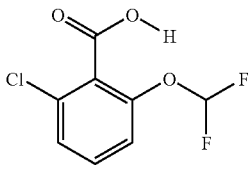

Potassium permanganate (1.64 g) was added portionwise over a period of 4 hours to a stirred mixture of 1-chloro-3-[(difluoromethyl)oxy]-2-methylbenzene (0.999 g) in t-butanol/water (20 ml, 1:1) heated at 100° C. The reaction mixture was heated for a further 4 hours—total heating time was 8 hours. The reaction mixture was allowed to cool to room temperature and then allowed to stand overnight. Aqueous sodium metabisulphite solution (5%) was added dropwise until the purple colour disappeared and the resultant mixture was filtered. The filtrate was adjusted to pH 10 using aqueous sodium carbonate solution and extracted with ether (100 ml). The aqueous portion was acidified using aqueous hydrochloric acid (2M) to pH 1 and then extracted with ether (100 ml). The ether layer was washed with saturated aqueous sodium chloride solution, dried (MgSO$_4$), filtered and evaporated. The title compound was obtained as a colourless oil (0.538 g).

$^1$H NMR (400 MHz, CHLOROFORM-d) ∂ ppm 7.42 (t, 1H), 7.34 (dd, 1H), 7.20 (dd, 1H), 6.55 (t, 1H, J=75 Hz), 5.9 (br. s., 1H).

LC-MS Retention Time 1.90 mins, MNH$_4^+$ 240, ES$^-$ 221.

Intermediate 30: Methyl
2-[(difluoromethyl)oxy]-6-fluorobenzoate

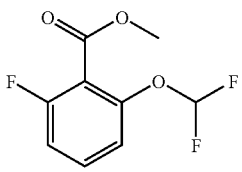

To a solution of methyl 6-fluorosalicilate (1.07 g) in anhydrous DMF (25 ml) stirred at 21° C. was added potassium carbonate (4.15 g) and cesium carbonate (3.26 g). The reaction mixture was stirred for 30 minutes and then cooled in ice for 20 minutes. Iododifluoromethane (5 g) was added, the ice-bath was removed and stirring continued for 18 hours. The reaction mixture was partitioned between ether (250 ml) and water (250 ml). The organic phase was washed with water (100 ml), 2M hydrochloric acid (100 ml), lithium chloride (100 ml), water (100 ml) and saturated brine (100 ml), dried over magnesium sulphate and evaporated to give an oil (1.68 g). The crude product was purified on 2 prepacked Flash silica columns (100 g) eluting with 0-50% ethyl acetate and cyclohexane for 60 minutes. Appropriate fractions were combined and evaporated to give the title compound as an oil (800 mg).

$^1$H NMR (400 MHz, CHLOROFORM-d) ∂ ppm 7.43 (m, 1H), 7.04 (m, 2H), 6.54 (t, 1H, J=72 Hz), 3.96 (s, 3H).

LC-MS Retention Time 1.18 mins.

Intermediate 31:
2-[(Difluoromethyl)oxy]-6-fluorobenzoic acid

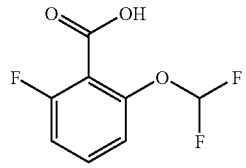

To a solution of methyl 2-[(difluoromethyl)oxy]-6-fluorobenzoate (800 mg) in anhydrous dioxane (20 ml) was added a solution of lithium hydroxide (260 mg) in water (10 ml). It was stirred for 15 hours, evaporated, dissolved in water (25 ml) and extracted with ethyl acetate (25 ml) and ether (25 ml). The aqueous phase was acidified with 5M hydrochloric acid and extracted with ethyl acetate (2×25 ml). The combined organic phases were washed with water (10 ml) and saturated brine (10 ml), dried over $Na_2SO_4$ and evaporated to give an oil which crystallised (616.3 mg). It was triturated with heptane (ca. 10 ml) and filtered off to give the title compound (456 mg).

$^1$H NMR (400 MHz, DMSO-$d_6$) ∂ ppm 7.57 (m, 1H), 7.28 (t, 1H, J=72 Hz), 7.23 (t, 1H), 7.16 (d, 1H).

LC-MS Retention Time 1.41 mins, ES$^-$ 205.

Intermediate 32: 1,1-Dimethylethyl[(2,6-dichlorophenyl)carbonyl]carbamate

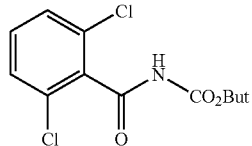

A stirred suspension of 2,6-dichlorobenzamide (4.7 g) in dichloromethane (80 ml) was treated with di-t-butyl dicarbonate (10.1 g) followed by 4-dimethylamino pyridine (350 mg). The solution, which formed after 15 minutes and after noticeable nitrogen evolution, was stirred for 20 hours before being diluted with dichloromethane (150 ml) and washed with 1M hydrochloric acid (1×100 ml), water (1×80 ml) and then passed through a hydrophobic frit. The organic phase was concentrated in vacuo to give a colourless oil (8.5 g). This oil was dissolved in ethanol (80 ml) before being treated with 2M sodium hydroxide (12.5 ml). The mixture was stirred for 90 hours before further 2M sodium hydroxide (10 ml) was added and stirring continued for a further 22 hours. The solvent was concentrated in vacuo and the residue was partitioned between ethyl acetate (200 ml) and water (150 ml). The separated organic phase was further washed with water (2×50 ml), passed through a hydrophobic frit and concentrated in vacuo to give the title compound (6.25 g) as a white solid.

$^1$H NMR (400 MHz, CHLOROFORM-d) δ ppm 7.62 (br. s., 1H) 7.25-7.37 (m, 3H) 1.37 (s, 9H)

LC-MS Retention Time 3.25 mins, $MNH_4^+$ 307.

Intermediate 33: 1,1-Dimethylethyl[(2,6-dichlorophenyl)carbonyl]{[2-(trifluoromethyl)-2-oxiranyl]methyl}carbamate

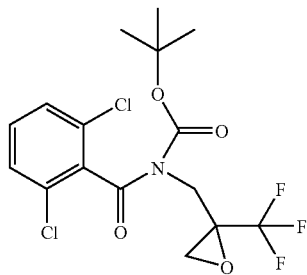

A stirred solution of 1,1-dimethylethyl[(2,6-dichlorophenyl) carbonyl]carbamate (6.25 g) in 1,2-dimethoxyethane (100 ml) was treated with sodium hydride (60% dispersion, 880 mg) portionwise over 15 minutes. After stirring for 45 minutes, the cloudy solution was transferred to a 100 ml dropping funnel and added dropwise to a stirred solution of [2-(trifluoromethyl)-2-oxiranyl]methyl 4-methylbenzenesulfonate (6.6 g) in 1,2-dimethoxyethane (100 ml). The mixture was stirred at room temperature for 19 hours. Propan-2-ol (1.5 ml) was added and after 15 minutes the whole mixture was partitioned between ethyl acetate (300 ml), water (100 ml) and brine (50 ml). The separated organic phase was then washed with water (2×50 ml), brine (1×50 ml), passed through a hydrophobic frit, concentrated in vacuo and re-evaporated in vacuo with ethanol (2×50 ml) to give a yellow oil (11.1 g). This was dissolved in dichloromethane (10 ml) and applied to a 70 g SPE cartridge. Elution with ethyl acetate: petroleum ether (1:9) then (1:6) gave two colourless oils (6.8 g) and (1.9 g). Repurification on a 70 g SPE cartridge with ethyl acetate:petroleum ether (1:19) then (1:9) as eluent gave the title compound (5.4 g).

$^1$H NMR (400 MHz, CHLOROFORM-d) δ ppm 7.28-7.26 (m, 3H) 4.76 (d, J=4.5 Hz, 1H) 4.39 (d, J=4.5 Hz 1H), 3.09-3.04 (m, 2H), 1.56 (s, 1H) 1.27 (s, 9H).

LC-MS Retention Time 3.78 mins, $MNH_4^+$ 431.

Intermediate 34: N-[2-(Azidomethyl)-3,3,3-trifluoro-2-hydroxypropyl]-2,6-dichlorobenzamide

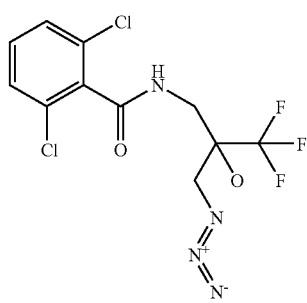

A stirred solution of 1,1-dimethylethyl[(2,6-dichlorophenyl)carbonyl]{[2-(trifluoromethyl)-2-oxiranyl]
methyl}carbamate (0.66 g) in dimethylformamide (12 ml) and water (0.2 ml) was treated with sodium azide (0.305 g). The mixture was stirred at room temperature overnight before being partitioned between ethyl acetate (50 ml) and water (40 ml). The separated aqueous phase was further extracted with ethyl acetate (2×30 ml) and the combined organic extracts were washed with water (3×25 ml), brine (1×20 ml), passed through a hydrophobic frit and concentrated in vacuo to give a colourless gum (0.71 g).

This gum was dissolved in dichloromethane (2 ml) and applied to a 50 g SPE cartridge. Purification via the Flashmaster 2 system using 0-25% ethyl acetate in dichloromethane gradient over 60 minutes gave, upon combination and concentration in vacuo of the relevant fractions, gave the title compound (235 mg) as a colourless gum. $^1$H NMR (400 MHz, CHLOROFORM-d) δ ppm 7.30-7.44 (m, 3H) 6.21 (br. s., 1H), 4.64 (s, 1H) 3.95-3.82 (m, 2H), 3.69 (ABq, J=12.0 Hz, 2H).

LC-MS Retention Time 3.03 mins, MNH$_4^+$ 374.

Intermediate 35: N-[2-(Aminomethyl)-3,3,3-trifluoro-2-hydroxypropyl]-2,6-dichlorobenzamide

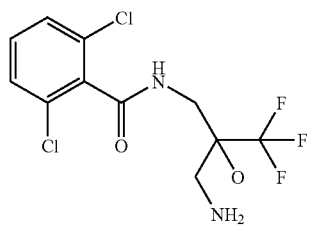

A stirred solution of N-[2-(azidomethyl)-3,3,3-trifluoro-2-hydroxypropyl]-2,6-dichlorobenzamide (0.06 g) in dry tetrahydrofuran (30 ml) was treated with polymer bound triphenylphosphine (3 mmol/g, 2.01 g). The mixture was vigorously stirred at room temperature for 19 hours before water (3 ml) was added. Stirring was continued at room temperature for a further 24 hours. The suspension was then diluted with tetrahydrofuran (50 ml) and then filtered through a pad of hyflo. The pad was washed with further tetrahydrofuran (2×30 ml). The combined filtrate and washings were partitioned between ethyl acetate (100 ml) and water (50 ml). The separated organic phase was further washed with water (2×50 ml), passed through a hydrophobic frit and concentrated in vacuo and then re-evaporated in vacuo with ethanol (1×20 ml) to give the title compound (0.84 g) as a near colourless gum.

$^1$H NMR (400 MHz, CHLOROFORM-d) δ ppm 7.24-7.40 (m, 3H) 6.15 (br. s., 1H) 3.95 (dd, J=15, 8 Hz, 1H) 3.58 (dd, J=15, 4 Hz, 1H) 3.19 (d, J=14 Hz, 1H) 2.99 (d, J=14 Hz, 1H) 1.5 (br. 2H).

LC-MS Retention Time 1.75 mins, MH$^+$ 331, 333.

Intermediate 36: 2-Bromo-1,3-bis(dibromomethyl)benzene

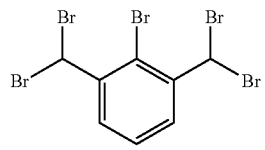

To a suspension of N-bromosuccinimide (28.5 g) in carbon tetrachloride (250 ml) were added 2-bromo-1,3-dimethylbenzene (2.66 ml) and AIBN (20 mg). The mixture was stirred and heated at reflux under nitrogen for 16 hours. More N-bromo succinimide (5.6 g) and AIBN (20 mg) were added and heating at reflux was continued for 3 hours. It was allowed to cool and the solid was filtered off and washed with carbon tetrachloride (2×100 ml). The filtrate was evaporated to give a white solid (9.8 g) which was triturated with heptane (150 ml) and filtered to give the title compound (8.3 g).

$^1$H NMR (400 MHz, CHLOROFORM-d) ∂ ppm 8.05 (d, 2H) 7.53 (t, 1H) 7.15 (s, 2H).

LC-MS Retention Time 3.96 mins.

Intermediate 37—2-Bromo-1,3-benzenedicarbaldehyde

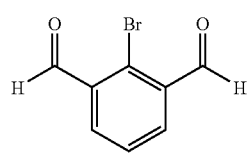

A mixture of 2-Bromo-1,3-bis(dibromomethyl)benzene (8.5 g) in formic acid (130 ml) and water (15 ml) was stirred and heated at reflux under nitrogen for 20 hours during which time the solid dissolved. It was concentrated in vacuo to give a suspension which was partitioned between water (150 ml) and dichloromethane (2×200 ml). The combined organic layers were washed with saturated brine (100 ml), dried over magnesium sulphate and evaporated to give a solid (4.25 g). Attempted crystallisation from ethanol (ca. 70 ml) failed and therefore 2M hydrochloric acid (25 ml) was added and heated at reflux for 1.5 hours. The mixture was allowed to cool overnight and evaporated to low volume plus some solid. This was then partitioned between ethyl acetate (150 ml) and water (50 ml) and the organic phase was washed with water (50 ml), saturated sodium bicarbonate (30 ml), water (30 ml) and saturated brine (30 ml). It was then dried over magnesium sulphate and evaporated to give a solid (3.8 g). This was purified on the Flashmaster using 2×100 g cartridges with 0-50% ethyl acetate in cyclohexane gradient over 1 hour. The pure fractions were combined and evaporated to give the title compound (2.38 g).

$^1$H NMR (400 MHz, CHLOROFORM-d) ∂ ppm 10.52 (s, 2H) 8.16 (d, 2H) 7.59 (t, 1H)

LC-MS Retention Time 2.40 & 2.64 mins.

Intermediate 38: 2-Bromo-1,3-bis(difluoromethyl)benzene

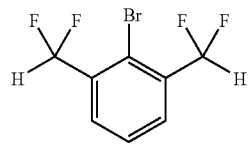

To a solution of 2-bromo-1,3-benzenedicarbaldehyde (1.4 g) in anhydrous dichloromethane (10 ml) was added bis(2-methoxyethyl)aminosulphur trifluoride (50% solution in tetrahydrofuran, 16 ml) over 10 minutes under nitrogen. Ethanol (70 µl) was then added, an exotherm was observed and the solution was stirred at 21° C. for 3 days. The solution was then heated at reflux at 75° C. for 20 hours. The solution was poured onto ice and partitioned between saturated sodium bicarbonate (50 ml) and ethyl acetate (100 ml). The aqueous layer was back extracted with ethyl acetate (50 ml). The organic layers were combined, washed with water (50 ml) and saturated brine (50 ml). It was then dried over magnesium sulphate, filtered and concentrated to give a residue (2.97 g). This was purified on the Flashmaster 2 column (100 g) eluting with 0-100% dichloromethane in cyclohexane gradient over 60 minutes. This gave a white solid (0.38 g). To a solution of this white solid (285 mg) in anhydrous toluene (3 ml) was added ethanol (20 μl) followed by bis(2-methoxyethyl)aminosulphur trifluoride (50% solution, 3 ml). The solution was stirred at 100° C. under nitrogen for three days. It was allowed to cool and poured onto ice and saturated sodium bicarbonate (50 ml). It was extracted with ether (50 ml), washed with sodium chloride, 2M hydrochloric acid, water and saturated brine. It was then dried over magnesium sulphate and evaporated to give a dark oil and some solid (335 mg). This was treated with heptane (3 ml) and some insoluble material was discarded to give upon evaporation an oil and solid (280 mg).

Kugelrohr distillation (3 Torr at ca. 125° C.) gave the title compound (124 mg).

$^1$H NMR (400 MHz, CHLOROFORM-d) ∂ ppm 7.80 (d, 2H) 7.57 (t, 1H) 7.00 (t, 2H).

LC-MS Retention Time 1.21 mins, MH$^+$ 290.

Intermediate 39: 2,6-Bis(difluoromethyl)benzoic acid

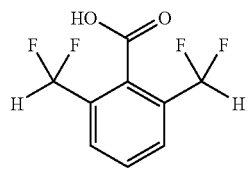

Lithium chloride (33 mg) (dried in vacuo at 80° C.) was suspended in anhydrous tetrahydrofuran (0.4 ml) under nitrogen followed by isopropyl magnesium chloride (2M in tetrahydrofuran, 0.4 ml). This was stirred for 1 hour and then a solution of 2-bromo-1,3-bis(difluoromethyl)benzene (124 mg) in anhydrous tetrahydrofuran (0.4 ml) was added. This was stirred under nitrogen at 21° C. for 3 hours and then solid $CO_2$ (1 small lump) was added causing vigorous bubbling. It was then allowed to stand overnight, then diluted with ethyl acetate (10 ml) and then washed with 2M hydrochloric acid (5 ml), water (5 ml) and saturated brine (10 ml). It was then dried over magnesium sulphate and evaporated to give a yellow glass (86.6 mg). This was purified by MDAP to give a residue which was dissolved in dichloromethane, dried over sodium sulphate and blown down to give the title compound (22.3 mg).

$^1$H NMR (400 MHz, DMSO-d$_6$) ∂ ppm 13.95 (br. s., 1H) 7.60 (d, 2H) 7.51 (t, 1H) 7.01 (t, 2H).

LC-MS Retention Time 0.71 mins, MH$^-$ 121.0.

Alternative Preparation of Intermediate 39

To a solution of methyl 2,6-bis(difluoromethyl)benzoate (205 mg) in methanol (3 ml) was added a solution of lithium hydroxide (48 mg) in methanol (3 ml). It was stirred at 21° C. and the initial oily suspension slowly cleared over ca. 2 hours but insoluble material remained. It was stirred for a total of 20 hours and then evaporated to dryness. It was partitioned between ethyl acetate (10 ml) and water (10 ml), washed with ether (10 ml), acidified with 2M hydrochloric acid and extracted with ethyl acetate (2×10 ml). This was washed with water (10 ml) and saturated brine (10 ml), dried over sodium sulphate and evaporated to give the title compound (146 mg).

$^1$H NMR (400 MHz, DMSO-d$_6$) ∂ ppm 14.21 (br. s., 1H) 7.87 (d, 2H) 7.80 (t, 1H) 7.18 (t, 2H).

Intermediate 40: 2,6-Bis(dibromomethyl)benzoic acid

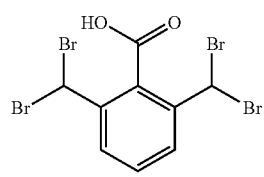

A solution of 2,6-dimethylbenzoic acid (5 g) in carbon tetrachloride (250 ml) was heated to gentle reflux and then the heat source was removed. Under a powerful spotlight, a solution of bromine (7.2 ml, 22.5 g) in carbon tetrachloride (100 ml) was added over 45 minutes. Vigorous evolution of hydrogen bromide occurred with gentle reflux. Stirring under the light was continued for another 30 minutes during which time a white solid precipitated. The mixture was allowed to cool overnight, the solid was filtered off, washed with carbon tetrachloride and then heptane and then dried in vacuo to give the title compound (4.38 g).

$^1$H NMR (400 MHz, DMSO-d$_6$) ∂ ppm 8.03 (d, 2H) 7.77 (t, 1H) 7.16 (s, 2H).

LC-MS Retention Time 1.00 mins, MH$^-$ 463.

Intermediate 41: 1-Hydroxy-3-oxo-1,3-dihydro-2-benzofuran-4-carbaldehyde

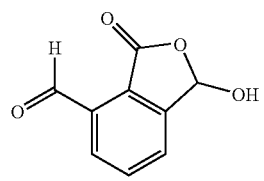

Aqueous sodium carbonate (5%, 70 ml) was brought to reflux and 2,6-bis(dibromomethyl)benzoic acid (4.38 g) was added portionwise. It was stirred and heated for 1.5 hours, most of the solid dissolved. The solution was decanted from an insoluble tan solid, allowed to cool and acidified with concentrated hydrochloric acid. No solid precipitated and thus it was cooled in ice and scratched to give the title compound (724 mg).

$^1$H NMR (400 MHz, DMSO-d$_6$) ∂ ppm 10.87 (s, 1H) 8.39 (s, 1H) 7.98 (m, 3H), 6.8 (br. s., 1H).

LC/MS Retention Time 0.60 mins, MH$^+$ 179.

Intermediate 42: Methyl 2,6-diformylbenzoate

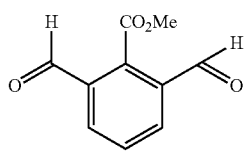

To a solution of 1-hydroxy-3-oxo-1,3-dihydro-2-benzofuran-4-carbaldehyde (720 mg) in anhydrous dimethylformamide (4 ml) was added potassium carbonate (613 mg). It was stirred for 30 minutes to give a thick white suspension. Iodomethane (0.4 ml) was added and stirred for 3 days. More methyl iodide (0.4 ml) was added and stirring continued for 24 hours. Most of the dimethylformamide was evaporated in vacuo. The pale yellow residue was partitioned between ethyl acetate (25 ml) and water (25 ml) and the organic phase was washed with aqueous lithium chloride (50 ml) and saturated brine (25 ml), dried over sodium sulphate and evaporated to give a pale yellow solid (645 mg).

This was purified on the Flashmaster 2 using 0-100% ethyl acetate in cyclohexane gradient over 60 minutes to give the title compound (532 mg) in 85% purity.

$^1$H NMR (400 MHz, CHLOROFORM-d) ∂ ppm 10.10 (s, 2H) 8.16 (d, 2H) 7.76-7.86 (m, 1H) 4.07 (s, 3H).

LC-MS Retention Time 2.20 mins, MH$^+$ 193.

Intermediate 43: Methyl 2,6-bis(difluoromethyl)benzoate

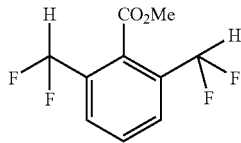

To a solution of methyl 2,6-diformylbenzoate (192 mg) in anhydrous toluene (3 ml) was added ethanol (10 µl) followed by bis(2-methoxyethyl)aminosulphur trifluoride (50% solution in toluene, 2 ml). The solution was stirred under nitrogen at 100° C. After ca. 1 hour a brown oil separated and this increased with time. Heating was continued for 19 hours. It was allowed to cool and partitioned between ethyl acetate (25 ml) and saturated sodium bicarbonate (10 ml). The organic phase was washed with water (20 ml), saturated brine (10 ml), 2M hydrochloric acid (20 ml), water (20 ml) and saturated brine (20 ml). It was dried over sodium sulphate and evaporated to give the title compound (207 mg).

$^1$H NMR (400 MHz, CHLOROFORM-d) ∂ ppm 7.84 (d, 2H) 7.70 (t, 1H) 7.08 (t, 2H) 3.99 (s, 3H).

LC-MS Retention Time 0.96 and 0.98 mins.

Intermediate 44: 5-Amino-1-(4-fluorophenyl)-N-(3,3,3-trifluoro-2-{[(2-fluoroethyl)amino]methyl}-2-hydroxypropyl)-1H-pyrazole-4-carboxamide

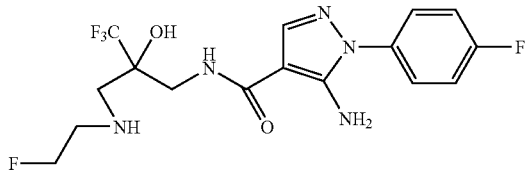

To a solution of 5-amino-1-(4-fluorophenyl)-N-{[2-(trifluoromethyl)-2-oxiranyl]methyl}-1H-pyrazole-4-carboxamide (1.03 g, 3 mmol) in anhydrous acetonitrile (10 ml) was added 2-fluoroethylamine hydrochloride (650 mg, 6 mmol, ca. 90% purity) and triethylamine (0.98 ml, 7 mmol) and the resulting suspension was shaken for 4 days. It was partitioned between ethyl acetate (70 ml) and water (20 ml), washed with saturated brine (20 ml), dried over sodium sulphate and evaporated to give a gum (1.57 g). This was purified on 100 g SiO$_2$ using the Flashmaster 2 with 0-100%/0 ethyl acetate in cyclohexane 60 minute gradient as eluent. This gave the title compound (924 mg).

$^1$H NMR (400 MHz, DMSO-d$_6$) ∂ ppm 7.98-8.08 (m, 1H) 7.94 (s, 1H) 7.53-7.61 (m, 2H) 7.32-7.40 (m, 2H) 6.37 (s, 2H) 4.53 (t, 1H) 4.41 (t, 1H) 3.61-3.72 (m, 1H) 3.43-3.53 (m, 1H) 2.74-2.92 (m, 4H).

LC-MS Retention Time 2.12 mins, MH$^+$ 408.

Intermediate 45: 1,1-Dimethylethyl[(2-chloro-6-fluorophenyl)carbonyl]carbamate

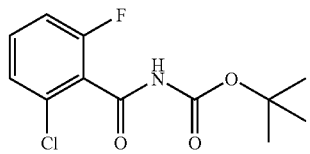

A solution of lithium bis(trimethylsilyl)amide in tetrahydrofuran (20 ml, 1M solution) was added dropwise to a stirred solution of t-butyl carbamate (1.17 g) in tetrahydrofuran (20 ml) cooled to <–70° C. under an atmosphere of nitrogen. A solution of 2-chloro-6-fluorobenzoyl chloride (1.93 g) in tetrahydrofuran (5 ml) was added dropwise. After the addition, a sample was removed via a syringe, a portion was quenched and the remainder allowed to warm to room temperature. Both samples were analysed by LC-MS. The reaction mixture was allowed to stir and gently warmed for 2 hours, the temperature of bath reached –40° C. The reaction mixture was partitioned between ethyl acetate (200 ml) and water (200 ml).

The aqueous phase was extracted with ethyl acetate (200 ml) and the combined organic phases washed with saturated aqueous sodium chloride solution, dried (MgSO$_4$), filtered and evaporated. The title compound was obtained as a white solid (2.65 g).

$^1$H NMR (400 MHz, CHLOROFORM-d) ∂ ppm 7.65 (br. s., 1H), 7.35 (m, 1H), 7.23 (d, 1H), 7.16 (t, 1H), 1.4 (s, 9H).

LC-MS Retention Time 3.08 mins, MNH$_4^+$ 291.

Intermediate 46: 5-Amino-1-(4-fluorophenyl)-N-(3,3,3-trifluoro-2-hydroxy-2-{[(phenylmethyl)amino]methyl}propyl)-1H-pyrazole-4-carboxamide

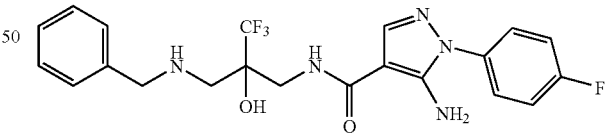

To 5-amino-1-(4-fluorophenyl)-N-{[2-(trifluoromethyl)-2-oxiranyl]methyl}-1H-pyrazole-4-carboxamide (15.3 g) in dioxane (250 ml) was added benzylamine (5.76 ml). The mixture was stirred at room temperature for 16 hours and then for a further 4 hours to ensure the reaction was complete. The orange solution was concentrated in vacuo to give an orange oil (which still contained some solvent). The oil was dried on the vacuum line to give the title compound (20.50 g) as an orange solid.

$^1$H NMR (400 MHz, CHLOROFORM-d) ∂ ppm 7.52 (m, 2H), 7.47 (s, 1H), 7.26 (m, 8H), 6.24 (t, 1H), 5.47 (br. s., 2H), 3.81 (m, 3H), 3.55 (dd, 1H), 3.02 (d, 1H), 2.71 (d, 1H).

LC-MS Retention Time 2.70 mins, MH$^+$ 452.

Example 1

5-Amino-N-(2-{[[(2,6-dichlorophenyl)carbonyl](methyl)amino]methyl}-3,3,3-trifluoro-2-hydroxypropyl)-1-(4-fluorophenyl)-1H-pyrazole-4-carboxamide

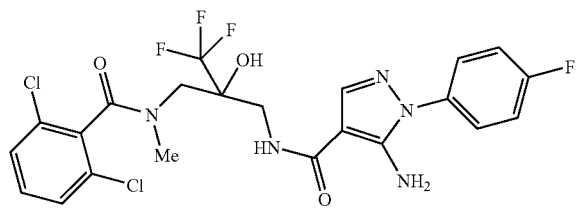

To a solution of 5-amino-1-(4-fluorophenyl)-N-{3,3,3-trifluoro-2-hydroxy-2-[(methylamino)methyl]propyl}-1H-pyrazole-4-carboxamide (56 mg, 0.15 mmol) in anhydrous tetrahydrofuran (2 ml) cooled in ice was added diisopropylethylamine (0.052 ml, 0.3 mmol) followed by 2,6-dichlorobenzoyl chloride (0.023 ml, 0.164 mmol). After 20 minutes, the mixture was removed from the ice and left at 21° C. for 19 hours. The mixture was blown down, the residue was dissolved in dichloromethane (3 ml) and washed with 2M hydrochloric acid (1 ml) and water (1 ml). It was again blown down and purified on a 5 g SPE cartridge, eluting with dichloromethane and then mixtures of cyclohexane/ethyl:acetate (10:1), (5:1), (3:1) and finally (2:1) to give the title compound (55.6 mg).

$^1$H NMR (400 MHz, DMSO-$d_6$) δ ppm 8.04 (t, J=6.1 Hz, 1H) 7.85 (s, 1H) 7.51-7.62 (m, 5H) 7.33-7.40 (m, 2H) 6.37 (s, 2H) 4.21 (d, J=14.3 Hz, 1H) 3.95-4.05 (m, 1H) 3.56 (d, J=14.3 Hz, 1H) 3.47 (dd, J=14.6, 5.3 Hz, 1H) 2.98 (s, 3H).

LC-MS Retention Time 3.41 mins, MH$^+$ 548.

Example 1 was further preparatively separated into its enantiomers (Isomers A and B) using a 2×25 cm Chiralpak AD column eluting with 30% ethanol in heptane at a flow rate of 1 ml/min.

Enantiomer 1 (Isomer A)

Analytical Chiral HPLC (25×0.46 cm Chiralpak AD column, 30% ethanol in heptane eluting at 1 ml/min)—Retention time 10.7 mins.

Circular Dichroism (MeCN, RT, 0.000144M, v=350-200 nm, cell length=0.2 cm)

204.6 nm (de=−8.03).

218.4 nm (de=1.69).

232.0 nm (de=−2.53).

262.0 nm (de=−3.18).

Enantiomer 2 (Isomer B)

Analytical Chiral HPLC (25×0.46 cm Chiralpak AD column, 30% ethanol in heptane eluting at 1 ml/min)—Retention time 14.6 mins.

Circular Dichroism (MeCN, RT, 0.000136M, v=350-200 nm, cell length=0.2 cm)

204.6 nm (de=7.88).

218.8 nm (de=−2.07).

231.4 nm (de=2.12).

262.6 nm (de=2.96).

Example 2

5-Amino-N-(2-{[[(2,6-dichlorophenyl)carbonyl](ethyl)amino]methyl}-3,3,3-trifluoro-2-hydroxypropyl)-1-(4-fluorophenyl)-1H-pyrazole-4-carboxamide

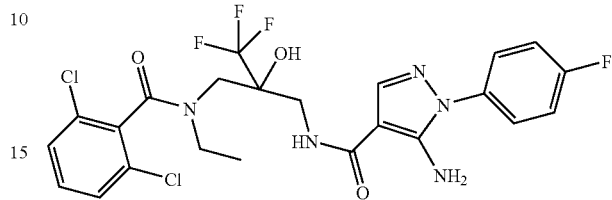

To a solution of 5-amino-N-{2-[(ethylamino)methyl]-3,3,3-trifluoro-2-hydroxypropyl}-1-(4-fluorophenyl)-1H-pyrazole-4-carboxamide (56 mg, 0.15 mmol) in anhydrous tetrahydrofuran (2 ml) cooled in ice was added diisopropylethylamine (0.052 ml, 0.3 mmol) followed by 2,6-dichlorobenzoyl chloride (0.023 ml, 0.164 mmol). After 20 minutes, the mixture was removed from the ice and left at 21° C. for 19 hours. The mixture was blown down, the residue was dissolved in dichloromethane (3 ml) and washed with 2M hydrochloric acid (1 ml) and water (1 ml). It was again blown down and purified on a 5 g SPE cartridge, eluting with dichloromethane and then mixtures of cyclohexane/ethyl:acetate (10:1), (5:1), (3:1) and finally (2:1) to give the title compound (73.5 mg).

$^1$H NMR (400 MHz, DMSO-$d_6$) δ ppm 8.07 (t, J=5.9 Hz, 1H) 7.85 (s, 1H) 7.52-7.63 (m, 5H) 7.33-7.44 (m, 2H) 6.37 (s, 2H) 4.22 (d, J=14.1 Hz, 1H) 3.96-4.05 (m, 1H) 3.46-3.57 (m, 3H) 3.21-3.32 (m, 1H) 1.08 (t, J=7.2 Hz, 3H).

LC-MS Retention Time 2.97 mins, MH$^+$ 562.

Example 2 was further preparatively separated into its enantiomers (Isomers A and B) using a 2×25 cm Chiralpak AD column eluting with 40% ethanol in heptane at a flow rate of 1 ml/min.

Enantiomer 1 (Isomer A)

Analytical Chiral HPLC (25×0.46 cm Chiralcel OD column, 40% ethanol in heptane eluting at 1 ml/min)—Retention time 4.60 mins.

Circular Dichroism (MeCN, RT, 0.000116M, v=350-200 nm, cell length=0.2 cm)

206.4 nm (de=13.58).

231.0 nm (de=5.52).

262.2 nm (de=3.33).

Enantiomer 2 (Isomer B)

Analytical Chiral HPLC (25×0.46 cm Chiralcel OD column, 40% ethanol in heptane eluting at 1 ml/min)—Retention time 6.50 mins.

Circular Dichroism (MeCN, RT, 0.000131M, v=350-200 nm, cell length=0.2 cm)

207.0 nm (de=−13.04).

229.0 nm (de=−5.64).

260.8 nm (de=−3.39).

Example 3

5-Amino-N-[2-({[(2,6-dichlorophenyl)carbonyl]amino}methyl)-3,3,3-trifluoro-2-hydroxypropyl]-1-(4-fluorophenyl)-1H-pyrazole-4-carboxamide

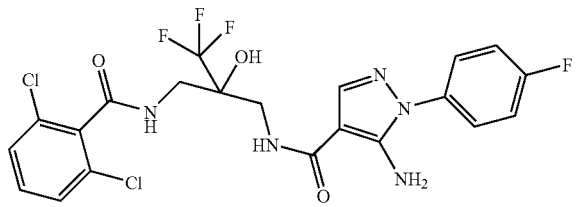

To a solution of 5-amino-N-[2-(aminomethyl)-3,3,3-trifluoro-2-hydroxypropyl]-1-(4-fluorophenyl)-1H-pyrazole-4-carboxamide (0.93 g, 2.57 mmol) in anhydrous tetrahydrofuran (12 ml) was added diisopropylethylamine (0.91 ml, 5.2 mmol) followed by 2,6-dichlorobenzoyl chloride (0.38 ml, 1.05 equiv). There was an immediate exotherm and therefore the mixture was placed in an ice/solid carbon dioxide bath for 20 minutes and then stirred at 21° C. for 17 hours. It was then partitioned between ethyl acetate (100 ml) and 2M hydrochloric acid (20 ml) and the organic phase was washed with water (20 ml), saturated brine (20 ml), saturated sodium bicarbonate (20 ml), water (20 ml) and saturated brine (20 ml) before being dried over magnesium sulphate and evaporated under reduced pressure to give a foam. This was purified on a Flashmaster column of silica (100 g) with a gradient of 0-100% ethyl acetate in cyclohexane over 60 minutes to give the title compound (1.07 g).

$^1$H NMR (400 MHz, DMSO-$d_6$) δ ppm 9.07 (t, J=6.4 Hz, 1H) 8.04 (t, J=6.1 Hz, 1H) 7.91 (s, 1H) 7.51-7.59 (m, 4H) 7.44-7.48 (m, 1H) 7.34-7.40 (m, 2H) 6.37 (s, 2H) 3.69-3.84 (m, 2H) 3.47-3.58 (m, 2H).

LC-MS Retention Time 3.26 mins, MH$^+$ 534.

Example 3 was further preparatively separated into its enantiomers (Isomers A and B) using a 2×20 cm Chiralpak AD column eluting with 20% propan-2-ol in heptane at a flow rate of 75 ml/min.

Enantiomer 1 (Isomer A)

Analytical Chiral HPLC (25×0.46 cm Chiralpak AD column, 30% ethanol in heptane eluting at 1 ml/min)—Retention time 6.34 mins.

Circular Dichroism (MeCN, RT, 0.000106M, v=350-200 nm, cell length=0.2 cm)

205.8 nm (de=−3.39).

240.8 nm (de=−2.59).

259.6 nm (de=−2.80).

Enantiomer 2 (Isomer B)

Analytical Chiral HPLC (25×0.46 cm Chiralpak AD column, 30% ethanol in heptane eluting at 1 ml/min)—Retention time 12.53 mins.

Circular Dichroism (MeCN, RT, 0.000133M, v=350-200 nm, cell length=0.2 cm)

205.4 nm (de=4.66).

240.4 nm (de=3.12).

259.6 nm (de=3.05).

Example 4

5-Amino-N-(2-{[[(2-chloro-6-fluorophenyl)carbonyl](ethyl)amino]methyl}-3,3,3-trifluoro-2-hydroxypropyl)-1-(4-fluorophenyl)-1H-pyrazole-4-carboxamide

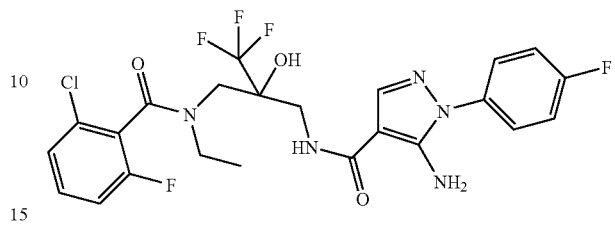

To a solution of 5-amino-N-{2-[(ethylamino)methyl]-3,3,3-trifluoro-2-hydroxypropyl}-1-(4-fluorophenyl)-1H-pyrazole-4-carboxamide (0.1885 g, 0.484 mmol) in dichloromethane (2 ml) was added diisopropylethylamine (0.253 ml, 1.45 mmol). After 5 minutes stirring, 2-chloro-6-fluorobenzoyl chloride (0.103 g, 0.533 mmol) was added. After stirring for 40 hours, the reaction mixture was concentrated to give a residue (0.371 g). Purification on a column of silica (20 g) gave the title compound (0.152 g) as a yellow solid.

$^1$H NMR (400 MHz, CHLOROFORM-d) δ ppm 7.75 (s, 1H) 7.49-7.56 (m, 2H) 7.41 (tt, J=8.5, 6.5 Hz, 1H) 7.18-7.25 (m, 2H) 6.97-7.04 (m, 2H) 5.47 (br. s., 1H) 4.00-4.18 (m, 2H) 3.67 (d, J=14.6 Hz, 1H) 3.54 (dd, J=14.8, 5.8 Hz, 1H) 3.41-3.49 (m, 1H) 3.23-3.34 (m, J=14.7, 7.3, 7.2, 7.0 Hz, 1H) 1.10 (t, J=7.2 Hz, 3H).

LC-MS Retention Time 3.33 mins, MH$^+$ 546.

Example 4 was further preparatively separated into its enantiomers (Isomers A (mixture of rotamers 1 and 2 and atropisomers 1 and 2) and B (mixture of rotamers 3 and 4 and atropisomers 3 and 4)) using a 2"×23 cm Chiralpak AD column eluting with 20% propan-2-ol in heptane at a flow rate of 15 ml/min.

Enantiomer 1 (Mixture of Rotamers 1 and 2 and Atropisomers 1 and 2)

Analytical Chiral HPLC (25×0.46 cm Chiralpak AD column, 20% propan-2-ol in heptane eluting at 1 ml/min)—Retention time 22.47 mins and 24.75 mins.

Enantiomer 2 (Mixture of Rotamers 3 and 4 and Atropisomers 3 and 4)

Analytical Chiral HPLC (25×0.46 cm Chiralpak AD column, 20% propan-2-ol in heptane eluting at 1 ml/min)—Retention time 30.23 mins and 34.68 mins.

Example 5

5-Amino-N-(2-{[[(2,6-difluorophenyl)carbonyl](ethyl)amino]methyl}-3,3,3-trifluoro-2-hydroxypropyl)-1-(4-fluorophenyl)-1H-pyrazole-4-carboxamide

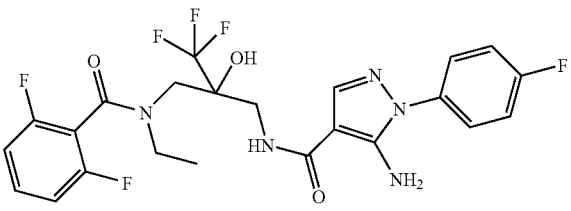

To a solution of 5-amino-N-{2-[(ethylamino)methyl]-3,3,3-trifluoro-2-hydroxypropyl}-1-(4-fluorophenyl)-1H-pyrazole-4-carboxamide (0.277 g, 0.712 mmol) in dry dichloromethane (ca. 11 ml), diisopropylethylamine (0.245 ml, 1.42 mmol) was added and then cooled in a freezer to −10 to −15° C. before a similarly cooled solution of 2,6-difluorobenzoyl chloride (0.123 g, 0.712 mmol) in dichloromethane (2 ml) was added with stirring. The mixture was stirred for 1 minute and then allowed to stand in the fridge for approx. 2 hours and then allowed to warm to room temperature. The next day the mixture was evaporated under reduced pressure and purified on a column of silica. Elution with 2% ethanol in chloroform gave, upon evaporation under reduced pressure, a clear glass (0.421 g) which, upon scraping, gave the title compound (0.356 g) as a white solid.

$^1$H NMR (400 MHz, CHLOROFORM-d) δ ppm 7.50-7.58 (m, 2H) 7.37-7.46 (m, 1H) 7.18-7.25 (m, 2H) 6.98-7.05 (m, 2H) 5.47 (br. s., 1H) 4.04-4.15 (m, 2H) 3.65 (d, J=14.8 Hz, 1H) 3.49-3.58 (m, 1H) 3.40-3.49 (m, 1H) 3.24-3.34 (m, 1H) 1.12 (t, J=7.2 Hz, 3H).

LC-MS Retention Time 3.07 mins, MH$^+$ 530.

Example 5 was further preparatively separated into its enantiomers (Isomers A and B) using a 4.6 mmid×25 cm Chiralcel OD column eluting with 20% ethanol in heptane at a flow rate of 1 ml/min.

Enantiomer 1 (Isomer A)

Analytical Chiral HPLC (25×4.6 cm Chiralpak AD column, 20% ethanol in heptane eluting at 1 ml/min)—Retention time 10.0 mins.

Circular Dichroism (MeCN, RT, 0.000138M, v=350-200 nm, cell length=0.2 cm)
204.0 nm (de=7.59).
229.0 nm (de=3.09).
263.2 nm (de=3.71).

Enantiomer 2 (Isomer B)

Analytical Chiral HPLC (25×0.46 cm Chiralpak AD column, 20% ethanol in heptane eluting at 1 ml/min)—Retention time 12.01 mins.

Circular Dichroism (MeCN, RT, 0.000143M, v=350-200 nm, cell length=0.2 cm)
203.2 nm (de=−6.51).
229.8 nm (de=−2.53).
262.6 nm (de=−3.49).

Example 6

5-Amino-N-[2-({[(2,6-difluorophenyl)carbonyl]amino}methyl)-3,3,3-trifluoro-2-hydroxypropyl]-1-(4-fluorophenyl)-1H-pyrazole-4-carboxamide

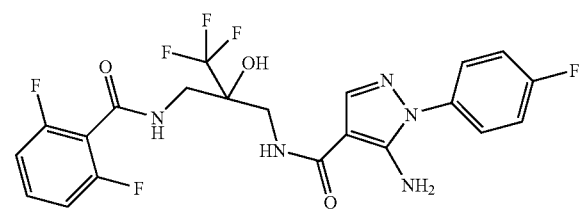

2,6-Difluorobenzoic acid (0.069 mmol) was weighed into a micronic tube. To this O-(7-azabenzotriazol-1-yl)-N,N,N',N'-tetramethyluronium hexafluorophosphate (HATU) (0.069 mmol, 26 mg) was added as a solution in DMF (200 μl). Diisopropylethylamine was then added (0.20 mmol, 36 μl) and the solution shaken for 5 minutes. 5-Amino-N-[2-(aminomethyl)-3,3,3-trifluoro-2-hydroxypropyl]-1-(4-fluorophenyl)-1H-pyrazole-4-carboxamide (0.069 mmol, 25 mg) was then added as a solution in DMF (200 μl). The solution was then shaken for a further 10 minutes and left to stand overnight at room temperature. LC-MS was taken after this time, the sample (20 μl) was diluted in acetonitrile (100 μl). LC-MS showed product present. The crude mixture was filtered and purified by mass directed HPLC. The products seemed to crash out when introduced to 90% H$_2$O (0.1% TFA)/10% MeCN (0.1% TFA) (of CAT-norm method) resulting in high back pressure. Method Cat-GR was used instead as 70% H$_2$O (0.1% TFA)/30°/0 MeCN (0.1% TFA) ensured no solid crashed out on introduction to column. The collected solution from the purification was transferred to a scintillation vial where MeCN/H$_2$O/TFA was removed in Genevac. The dried compound was then transferred to pre-tared vial. Weight obtained for desired product 22.7 mg.

$^1$H NMR (400 MHz, DMSO-d$_6$) δ ppm 8.98 (t, J=6.4 Hz, 1H) 8.11 (t, J=6.1 Hz, 1H) 7.95 (s, 1H) 7.60-7.51 (m, 3H) 7.39-7.35 (t, 2H) 7.22-7.16 (t, 2H) 6.85 (s, 1H) 6.40-6.30 (br. s., 2H) 3.79-3.71 (m, 2H) 3.58-3.47 (m, 2H).

LC-MS Retention Time 2.9 mins, MH$^+$ 502.

Example 7

5-Amino-N-[2-({[(2-chloro-6-fluorophenyl)carbonyl]amino}methyl)-3,3,3-trifluoro-2-hydroxypropyl]-1-(4-fluorophenyl)-1H-pyrazole-4-carboxamide

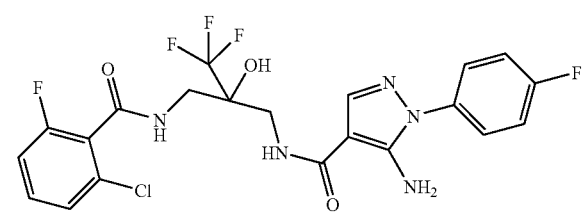

A solution of 2-chloro-6-fluorobenzoyl chloride (0.169 g) in dry tetrahydrofuran (1 ml) was added to a stirred mixture of 5-amino-N-[2-(aminomethyl)-3,3,3-trifluoro-2-hydroxypropyl]-1-(4-fluorophenyl)-1H-pyrazole-4-carboxamide (0.289 g) and diisopropylethylamine (0.21 ml) in a mixture of dichloromethane (4 ml) and tetrahydrofuran (3 ml) cooled to <5° C. After the addition, the cooling bath was removed and the reaction mixture stirred at room temperature for 20 minutes. Water (10 ml) and dichloromethane (10 ml) were added to the reaction mixture and the resultant mixture stirred vigorously. The phases were separated using a hydrophobic frit and the aqueous phase washed with additional dichloromethane (10 ml). The organic phase was evaporated and the residue purified by chromatography on silica (20 g cartridge) eluting with 0-100% ethyl acetate in cyclohexane. Appropriate fractions were combined and evaporated to give the title compound (0.409 g).

$^1$H NMR (400 MHz, DMSO-d$_6$) δ ppm 9.05 (br. s., 1H) 8.11 (br. s., 1H) 7.85 (s, 1H) 7.68-7.60 (m, 2H) 7.55-7.43 (m, 1H) 7.41-7.28 (m, 4H) 6.68 (br. s., 1H) 6.46-6.30 (br. s., 2H) 3.79-3.72 (m, 2H) 3.58-3.47 (m, 2H).

LC-MS Retention Time 3.08 mins, MH$^+$ 518, 520.

Example 7 was further preparatively separated into its enantiomers (Isomers A and B) using a 2"×20 cm Chiralpak AD column eluting with 20% ethanol in heptane at a flow rate of 75 ml/min.

Enantiomer 1 (Isomer A)
Analytical Chiral HPLC (25×0.46 cm Chiralpak AD column, 40% ethanol in heptane eluting at 1 ml/min)—Retention time 6.34 mins.
Circular Dichroism (MeCN, RT, 0.000135M, v=350-200 nm, cell length=0.2 cm)
203.2 nm (de=−3.92).
237.4 nm (de=−3.16).
260.0 nm (de=−2.99).
Enantiomer 2 (Isomer B)
Analytical Chiral HPLC (25×0.46 cm Chiralpak AD column, 40% ethanol in heptane eluting at 1 ml/min)—Retention time 8.95 mins.
Circular Dichroism (MeCN, RT, 0.000148M, v=350-200 nm, cell length=0.2 cm)
203.4 nm (de=4.32).
239.0 nm (de=3.32).
260.0 nm (de=3.07).

Example 8

5-Amino-N-(2-{[[(2,6-difluorophenyl)carbonyl](methyl)amino]methyl}-3,3,3-trifluoro-2-hydroxypropyl)-1-(4-fluorophenyl)-1H-pyrazole-4-carboxamide

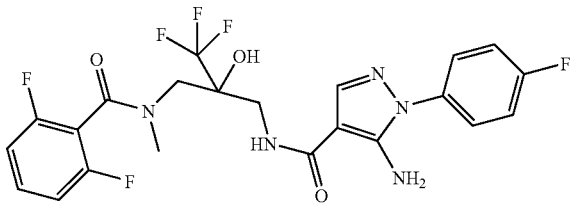

Similarly prepared to Example 6 from 5-amino-1-(4-fluorophenyl)-N-{3,3,3-trifluoro-2-hydroxy-2-[(methylamino)methyl]propyl}-1H-pyrazole-4-carboxamide and 2,6-difluorobenzoic acid.
$^1$H NMR (400 MHz, DMSO-$d_6$) δ ppm 8.05 (t, 1H) 7.88 (s, 1H) 7.55-7.61 (m, 2H) 7.37 (t, 2H) 7.25 (t, 2H) 6.95 (br. s., 1H) 6.29-6.43 (br. s., 2H) 4.10 (d, 1H) 3.81 (dd, 1H) 3.72 (d, 1H) 3.46 (dd, 1H) 3.04 (s, 3H).
LC-MS Retention Time 3.11 mins, MH$^+$ 516.

Example 9

5-Amino-N-(2-{[[(2-chloro-6-fluorophenyl)carbonyl](methyl)amino]methyl}-3,3,3-trifluoro-2-hydroxypropyl)-1-(4-fluorophenyl)-1H-pyrazole-4-carboxamide

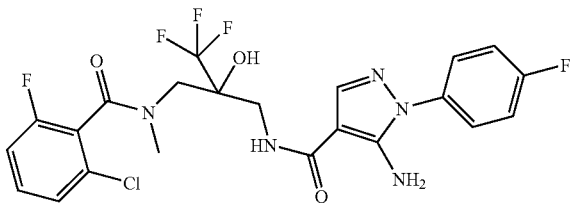

Similarly prepared to Example 6 from 5-amino-1-(4-fluorophenyl)-N-{3,3,3-trifluoro-2-hydroxy-2-[(methylamino)methyl]propyl}-1H-pyrazole-4-carboxamide and 2-chloro-6-fluorobenzoic acid.
$^1$H NMR (400 MHz, DMSO-$d_6$) δ ppm 8.05 (t, J=6.1 Hz, 1H) 7.85 (s, 1H) 7.55-7.62 (m, 2H) 7.46 (d, 1H) 7.34-7.41 (m, 3H) 7.00 (s, 0.5H) 6.94 (s, 0.5H) 6.32-6.40 (br. m., 2H) 4.20 (d, 0.5H) 4.10 (d, 0.5H) 3.94 (dd, 0.5H) 3.84 (dd, 0.5H) 3.69 (d, 0.5H) 3.60 (d, 0.5H) 3.01 (d, 3H).
LC-MS Retention Time 3.17 mins, MH$^+$ 532, 534.

Example 10

5-Amino-N-{2-[(ethyl{[2-(methylsulfonyl)phenyl]carbonyl}amino)methyl]-3,3,3-trifluoro-2-hydroxypropyl}-1-(4-fluorophenyl)-1H-pyrazole-4-carboxamide

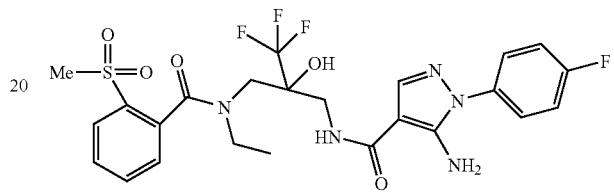

2-(Methylsulphonyl)benzoic acid (0.204 g, 1.017 mmol) was dissolved in dry dimethylformamide before diisopropylethylamine (0.531 ml, 3.05 mmol) was added. O-7-Azabenzotriazol-1-yl)-N,N,N',N'-tetramethyluronium hexafluorophosphate (HATU) (0.464 g, 1.22 mmol) was added and the reaction stirred for 10 minutes. The reaction mixture was cooled in ice and then 5-amino-N-{2-[(ethylamino)methyl]-3,3,3-trifluoro-2-hydroxypropyl}-1-(4-fluorophenyl)-1H-pyrazole-4-carboxamide (0.46 g, 1.118 mmol, 1.1 equiv) was added (washed in with dimethylformamide) (total volume of dimethylformamide used 2.5 ml). The reaction was then stirred at room temperature overnight. The reaction mixture was then concentrated under reduced pressure and the residue was partitioned between dichloromethane and water. The product was extracted into dichloromethane and concentrated under reduced pressure. The crude product was purified on silica (50 g) with a 0-100% ethyl acetate:dichloromethane over 40 minutes as gradient to give the title compound (0.53 g).
$^1$H NMR (250 MHz, DMSO-$d_6$) δ ppm 8.03 (d, 1H) 7.85 (s, 1H) 7.67-7.83 (m, 3H) 7.50-7.64 (m, 3H) 7.26-7.36 (m, 2H) 6.52 (br. s., 1H) 6.09 (br. s., 2H) 3.26-4.25 (m, 6H) 3.23 (s, 3H) 1.08 (t, 3H).
LC-MS Retention Time 3.01 mins, MH$^+$ 572.
Example 10 was further preparatively separated into its enantiomers (Isomers A and B) using a 2×25 cm Chiralpak AD column eluting with 80% ethanol in heptane at a flow rate of 1 ml/min.
Enantiomer 1 (Isomer A)
Analytical Chiral HPLC (25×0.46 cm Chiralpak AD column, 80% ethanol in heptane eluting at 1 ml/min)—Retention time 5.86 mins.
Circular Dichroism (MeCN, RT, 0.000127M, v=350-200 nm, cell length=0.2 cm)
210.2 nm (de=2.45).
226.6 nm (de=−3.43).
271.0 nm (de=−3.34).
Enantiomer 2 (Isomer B)
Analytical Chiral HPLC (25×0.46 cm Chiralpak AD column, 80% ethanol in heptane eluting at 1 ml/min)—Retention time 12.01 mins.

Circular Dichroism (MeCN, RT, 0.000125M, v=350-200 nm, cell length=0.2 cm)

209.8 nm (de=−2.04).

227.2 nm (de=3.57).

270.4 nm (de=3.20).

Example 11

5-Amino-N-[2-({[(2,6-dibromophenyl)carbonyl]amino}methyl)-3,3,3-trifluoro-2-hydroxypropyl]-1-(4-fluorophenyl)-1H-pyrazole-4-carboxamide

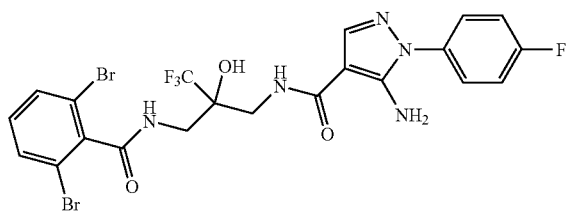

To a solution of 2,6-dibromobenzoic acid (28 mg, 0.1 mmol) in anhydrous tetrahydrofuran (1 ml) was added anhydrous dimethylformamide (4 μl) followed by oxalyl chloride (100 μl of a 1 ml solution of 87 μl of oxalyl chloride in THF; 0.1 mmol). The mixture effervesced and was stirred under nitrogen for 45 minutes. A solution of 5-amino-N-[2-(aminomethyl)-3,3,3-trifluoro-2-hydroxypropyl]-1-(4-fluorophenyl)-1H-pyrazole-4-carboxamide (25.3 mg, 0.07 mmole) in anhydrous tetrahydrofuran (0.5 ml) and diisopropylethylamine (52 μl, 0.3 mmol) was added. It was then stirred under nitrogen at 21° C. for 3 days. It was blown down, partitioned between dichloromethane (5 ml) and 2M hydrochloric acid (2 ml). The organic layer was blown down and the residue purified on a 5 g SPE silica cartridge. Elution with dichloromethane then cyclohexane:ethyl acetate (10:1), (5:1), (3:1), (2:1) (3 times) and finally (1:1) (3 times). The title product was eluted in the third (2:1) fraction and the first (1:1) fraction. These fractions were combined and evaporated to give the title product (39.6 mg).

$^1$H NMR (400 MHz, DMSO-$d_6$) δ ppm 9.06 (t, 1H) 8.03 (s, 1H) 7.91 (t, 1H) 7.71 (d, 2H) 7.54-7.61 (m, 2H) 7.34-7.40 (m, 2H) 7.30 (t, 1H) 6.68 (s, 1H) 6.37 (s, 2H) 3.79-3.89 (m, 1H) 3.66-3.76 (m, 1H) 3.55-3.65 (m, 1H) 3.43-3.52 (m, 1H).

LC-MS Retention Time 3.29 mins, MH$^+$ 622, 624, 626.

Example 11 was further preparatively separated into its enantiomers (Isomers A and B) using a 5 cm×20 cm Chiralpak AD column eluting with 25% ethanol in heptane at a flow rate of 75 ml/min.

Enantiomer 1 (Isomer A)

Analytical Chiral HPLC (25 cm Chiralpak AD column, 30% ethanol in heptane eluting at 1 ml/min)—Retention time 8.5 mins.

Circular Dichroism (MeCN, RT, 0.000159M, v=350-200 nm, cell length=0.2 cm)

207.2 nm (de=3.65).

258.8 nm (de=2.85).

Enantiomer 2 (Isomer B)

Analytical Chiral HPLC (25 cm Chiralpak AD column, 30% ethanol in heptane eluting at 1 ml/min)—Retention time 12.1 mins.

Circular Dichroism (MeCN, RT, 0.0000947M, v=350-200 nm, cell length=0.2 cm)

208.2 nm (de=−3.51).

260.8 nm (de=−2.67).

Example 12

5-Amino-N-[2-({[(2-bromo-6-chlorophenyl)carbonyl]amino}methyl)-3,3,3-trifluoro-2-hydroxypropyl]-1-(4-fluorophenyl)-1H-pyrazole-4-carboxamide

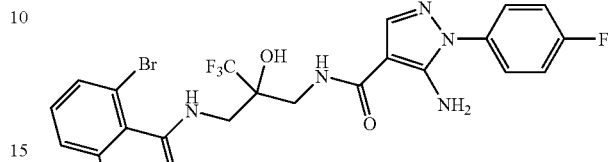

To a solution of 5-amino-N-[2-(aminomethyl)-3,3,3-trifluoro-2-hydroxypropyl]-1-(4-fluorophenyl)-1H-pyrazole-4-carboxamide (250 mg, 0.69 mmol) in tetrahydrofuran (2 ml) was added 2-bromo-6-chlorobenzoyl chloride (192.7 mg, 0.76 mmol) followed by diisopropylethylamine (178 mg, 1.38 mmol). The reaction was left stirring under nitrogen overnight. LC-MS analysis showed the reaction was complete. The reaction mixture was concentrated in vacuo. The residue was redissolved in dichloromethane and washed with 2M hydrochloric acid followed by water. The organic layer was concentrated in vacuo to give the title compound (280 mg).

$^1$H NMR (400 MHz, CHLOROFORM-d) δ ppm 7.77 (s, 1H) 7.40-7.49 (m, 3H) 7.28-7.38 (m, 1H) 7.12-7.23 (m, 3H) 6.43-6.53 (m, 1H) 4.02-4.14 (m, 2H) 3.48-3.60 (m, 1H) 3.36-3.46 (m, 1H).

LC-MS Retention Time 3.19 mins. MH$^+$ 580.

Example 12 was further preparatively separated into its enantiomers (Isomers A and B) using a 5 cm×20 cm Chiralpak AD column eluting with 25% ethanol in heptane at a flow rate of 75 ml/min.

Enantiomer 1 (Isomer A)

Analytical Chiral HPLC (25 cm Chiralpak AD column, 30% ethanol in heptane eluting at 1 ml/min)—Retention time 8.4 mins.

Circular Dichroism (MeCN, RT, 0.000130M, v=350-200 nm, cell length=0.2 cm)

206.6 nm (de=4.44).

239.8 nm (de=2.74).

260.2 nm (de=3.08).

Enantiomer 2 (Isomer B)

Analytical Chiral HPLC (25 cm Chiralpak AD column, 30% ethanol in heptane eluting at 1 ml/min)—Retention time 12.0 mins.

Circular Dichroism (MeCN, RT, 0.000155M, v=350-200 nm, cell length=0.2 cm)

206.4 nm (de=−3.85).

241.0 nm (de=−2.71).

260.4 nm (de=−2.92).

Example 13

5-Amino-N-[2-({[(2-bromo-6-fluorophenyl)carbonyl]amino}methyl)-3,3,3-trifluoro-2-hydroxypropyl]-1-(4-fluorophenyl)-1H-pyrazole-4-carboxamide

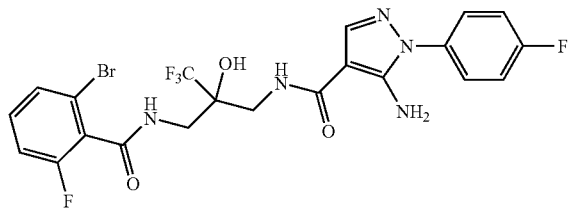

To a solution of 2-bromo-6-fluorobenzoic acid (22 mg, 0.1 mmol) in anhydrous tetrahydrofuran (1 ml) was added anhydrous dimethylformamide (4 μl) and then a 100 μl aliquot (0.1 mmol) of a solution of oxalyl chloride (87 μl, 1 mmol) in anhydrous tetrahydrofuran (0.9 ml). It was stirred for 30 minutes and then a solution of 5-amino-N-[2-(aminomethyl)-3,3,3-trifluoro-2-hydroxypropyl]-1-(4-fluorophenyl)-1H-pyrazole-4-carboxamide (29 mg, 0.08 mmol) in anhydrous tetrahydrofuran (0.5 ml) and diisopropylethylamine (54 μl) was added and washed in with tetrahydrofuran (100 μl). It was then stirred at 21° C. for 4 hours during which time a solid formed. It was blown down, dissolved in dichloromethane (5 ml) and washed successively with ca. 5 ml of water, 2M hydrochloric acid, water, saturated sodium bicarbonate, water and saturated brine. It was blown down to give a white solid (41 mg). Dichloromethane (ca. 2 ml) was added and gave the title compound as an insoluble white solid (20 mg) which was filtered off and washed with ether (1 ml). The filtrate was loaded onto a 5 g SPE SiO$_2$ column. Elution with dichloromethane, ether, cyclohexane:ethyl acetate (2:1) and (1:1) (3 times) gave upon combination and evaporation of the relevant fractions further title compound (18.6 mg).

$^1$H NMR (400 MHz, DMSO-d$_6$) δ ppm 9.02 (t, 1H) 8.04 (t, 1H) 7.91 (s, 1H) 7.51-7.60 (m, 3H) 7.33-7.44 (m, 4H) 6.65 (s, 1H) 6.36 (s, 2H) 3.71-3.82 (m, 2H) 3.45-3.57 (m, 2H).

LC-MS Retention Time 3.15 mins, MH$^+$ 564, 563.

Example 13 was further preparatively separated into its enantiomers (Isomers A and B) using a 2"×23 cm Chiralpak AD column eluting with 50% acetonitrile in water at a flow rate of 70 ml/min.

Enantiomer 1 (Isomer A)

Analytical Chiral HPLC (25×0.46 cm Chiralpak AD column, 30% ethanol in heptane eluting at 1 ml/min)—Retention time 10.20 mins.

Circular Dichroism (MeCN, RT, 0.00014M, v=350-200 nm, cell length=0.2 cm)

204.6 nm (de=−3.23).
218 nm (de=0.25).
244 nm (de=−2.72).
244 nm (de=−2.77).

Enantiomer 2 (Isomer B)

Analytical Chiral HPLC (25×0.46 cm Chiralpak AD column, 30% ethanol in heptane eluting at 1 ml/min)—Retention time 13.98 mins.

Circular Dichroism (MeCN, RT, 0.000131M, v=350-200 nm, cell length=0.2 cm)

204 nm (de=3.66).
218 nm (de=0.00).
240 nm (de=2.58)
260 nm (de=2.53)

Example 14

5-Amino-N-(2-{[({2-chloro-6-[(difluoromethyl)oxy]phenyl}carbonyl)amino]methyl}-3,3,3-trifluoro-2-hydroxypropyl)-1-(4-fluorophenyl)-1H-pyrazole-4-carboxamide

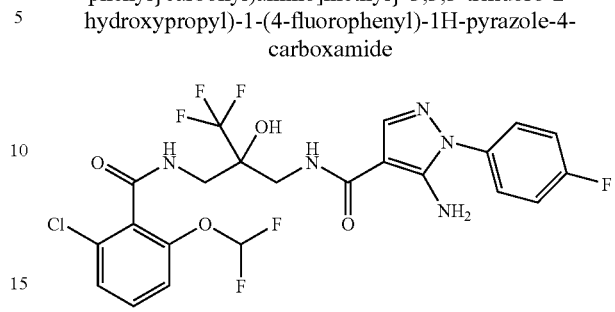

To a solution of 2-chloro-6-[(difluoromethyl)oxy]benzoic acid (220 mg) in anhydrous tetrahydrofuran (5 ml) was added anhydrous dimethylformamide (10 μl) followed by oxalyl chloride (87 μl). It was stirred under nitrogen at room temperature for 30 minutes. A solution of 5-amino-N-[2-(aminomethyl)-3,3,3-trifluoro-2-hydroxypropyl]-1-(4-fluorophenyl)-1H-pyrazole-4-carboxamide (325 mg) in anhydrous tetrahydrofuran (3 ml) and diisopropylethylamine (0.52 ml) was added washed in with further tetrahydrofuran (1 ml).

The mixture was stirred under nitrogen for 22 hours. It was added to ethyl acetate (50 ml) and washed sequentially with water (50 ml), 2M hydrochloric acid (25 ml), water (25 ml), saturated sodium bicarbonate (25 ml), water (25 ml) and saturated brine (25 ml). It was then dried over MgSO$_4$ and evaporated. The residue was purified on a 10 g silica SPE cartridge eluting with dichloromethane and then cyclohexane:ethyl acetate (4:1), (3:1) and finally (2:1) (8 times). The appropriate fractions were combined and evaporated and dissolved in methanol and blown down to give the title compound (369 mg) as a glass.

$^1$H NMR (400 MHz, DMSO) ∂ ppm 8.97 (t, 1H), 8.00 (t, 1H), 7.90 (s, 1H), 7.58 (m, 2H), 7.51 (m, 1H), 7.38 (m, 3H), 7.36 (t, 1H, J=60 Hz), 7.26 (d, 1H), 6.63 (s, 1H), 6.35 (br. s., 2H), 3.78 (m, 2H), 3.48 (m, 2H).

LC/MS Retention Time 1.08 mins, MH$^+$ 566.

Example 14 was further preparatively separated into its enantiomers (Isomers A and B) using a 5 cm×20 cm Chiralpak AD column eluting with 30% propan-2-ol in heptane at a flow rate of 75 ml/min.

Enantiomer 1 (Isomer A)

Analytical Chiral HPLC (25×0.46 cm Chiralpak AD column, 40% propan-2-ol in heptane eluting at 1 ml/min)—Retention time 5.55 mins.

Circular Dichroism (MeCN, RT, 0.000136M, v=350-200 nm, cell length=0.2 cm)

204.6 nm (de=−4.49).
217.8 nm (de=0.63).
240 nm (de=−3.28).
262 nm (de=−3.20).

Enantiomer 2 (Isomer B)

Analytical Chiral HPLC (25×0.46 cm Chiralpak AD column, 40% propan-2-ol in heptane eluting at 1 ml/min)—Retention time 7.63 mins.

Circular Dichroism (MeCN, RT, 0.000134M, v=350-200 nm, cell length=0.2 cm)

203.8 nm (de=4.55).
218.6 nm (de=−0.23).
240 nm (de=2.94).
260 nm (de=2.84).

The following Examples were similarly prepared to Example 14:

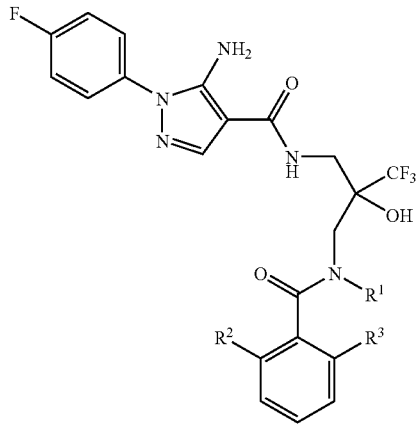

| Example Number | R¹ | R² | R³ | Compound Name |
|---|---|---|---|---|
| 15 | H | CF₃ | CF₃ | 5-amino-N-{2-[({[2,6-bis(trifluoromethyl)phenyl]carbonyl}amino)methyl]-3,3,3-trifluoro-2-hydroxypropyl}-1-(4-fluorophenyl)-1H-pyrazole-4-carboxamide |
| 15 Enantiomer 1 | H | CF₃ | CF₃ | 5-amino-N-{2-[({[2,6-bis(trifluoromethyl)phenyl]carbonyl}amino)methyl]-3,3,3-trifluoro-2-hydroxypropyl}-1-(4-fluorophenyl)-1H-pyrazole-4-carboxamide |
| 15 Enantiomer 2 | H | CF₃ | CF₃ | 5-amino-N-{2-[({[2,6-bis(trifluoromethyl)phenyl]carbonyl}amino)methyl]-3,3,3-trifluoro-2-hydroxypropyl}-1-(4-fluorophenyl)-1H-pyrazole-4-carboxamide |
| 16 | CH₃ | Cl | Br | 5-amino-N-(2-{[[(2-bromo-6-chlorophenyl)carbonyl](methyl)amino]methyl}-3,3,3-trifluoro-2-hydroxypropyl)-1-(4-fluorophenyl)-1H-pyrazole-4-carboxamide |
| 17 | CH₂CH₂F | F | F | 5-amino-N-(2-{[[(2,6-difluorophenyl)carbonyl](2-fluoroethyl)amino]methyl}-3,3,3-trifluoro-2-hydroxypropyl)-1-(4-fluorophenyl)-1H-pyrazole-4-carboxamide |
| 18 | CH₂CH₂F | F | CF₃ | 5-amino-1-(4-fluorophenyl)-N-{3,3,3-trifluoro-2-[((2-fluoroethyl){[2-fluoro-6-(trifluoromethyl)phenyl]carbonyl}amino)methyl]-2-hydroxypropyl}-1H-pyrazole-4-carboxamide |
| 19 | H | CF₃ | F | 5-amino-1-(4-fluorophenyl)-N-{3,3,3-trifluoro-2-[({[2-fluoro-6-(trifluoromethyl)phenyl]carbonyl}amino)methyl]-2-hydroxypropyl}-1H-pyrazole-4-carboxamide |
| 19 Enantiomer 1 | H | CF₃ | F | 5-amino-1-(4-fluorophenyl)-N-{3,3,3-trifluoro-2-[({[2-fluoro-6-(trifluoromethyl)phenyl]carbonyl}amino)methyl]-2-hydroxypropyl}-1H-pyrazole-4-carboxamide |
| 19 Enantiomer 2 | H | CF₃ | F | 5-amino-1-(4-fluorophenyl)-N-{3,3,3-trifluoro-2-[({[2-fluoro-6-(trifluoromethyl)phenyl]carbonyl}amino)methyl]-2-hydroxypropyl}-1H-pyrazole-4-carboxamide |
| 20 | H | OCHF₂ | OCHF₂ | 5-amino-N-(2-{[({2,6-bis[(difluoromethyl)oxy]phenyl}carbonyl)amino]methyl}-3,3,3-trifluoro-2-hydroxypropyl)-1-(4-fluorophenyl)-1H-pyrazole-4-carboxamide |
| 21 | CH₃ | CF₃ | F | 5-amino-1-(4-fluorophenyl)-N-(3,3,3-trifluoro-2-{[{[2-fluoro-6-(trifluoromethyl)phenyl]carbonyl}(methyl)amino]methyl}-2- |

-continued

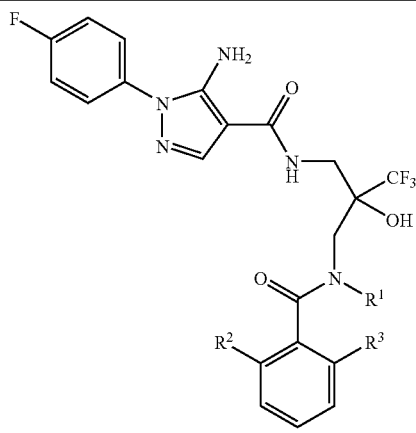

| Example Number | R¹ | R² | R³ | Compound Name |
|---|---|---|---|---|
| | | | | hydroxypropyl)-1H-pyrazole-4-carboxamide |
| 22 | CH₃ | CF₃ | CF₃ | 5-amino-N-(2-{[{[2,6-bis(trifluoromethyl)phenyl]carbonyl}(methyl)amino]methyl}-3,3,3-trifluoro-2-hydroxypropyl)-1-(4-fluorophenyl)-1H-pyrazole-4-carboxamide |
| 23 | CH₂CH₃ | CF₃ | F | 5-amino-N-{2-[(ethyl{[2-fluoro-6-(trifluoromethyl)phenyl]carbonyl}amino)methyl]-3,3,3-trifluoro-2-hydroxypropyl}-1-(4-fluorophenyl)-1H-pyrazole-4-carboxamide |
| 24 | CH₂CH₃ | Br | Cl | 5-amino-N-(2-{[[(2-bromo-6-chlorophenyl)carbonyl](ethyl)amino]methyl}-3,3,3-trifluoro-2-hydroxypropyl)-1-(4-fluorophenyl)-1H-pyrazole-4-carboxamide |
| 25 | CH₂CH₃ | OCHF₂ | Cl | 5-amino-N-(2-{[({2-chloro-6-[(difluoromethyl)oxy]phenyl}carbonyl)(ethyl)amino]methyl}-3,3,3-trifluoro-2-hydroxypropyl)-1-(4-fluorophenyl)-1H-pyrazole-4-carboxamide |
| 26 | CH₂CH₃ | OCHF₂ | OCHF₂ | 5-amino-N-(2-{[({2,6-bis[(difluoromethyl)oxy]phenyl}carbonyl)(ethyl)amino]methyl}-3,3,3-trifluoro-2-hydroxypropyl)-1-(4-fluorophenyl)-1H-pyrazole-4-carboxamide |
| 27 | CH₂CH₃ | CF₃ | CF₃ | 5-amino-N-(2-{[{[2,6-bis(trifluoromethyl)phenyl]carbonyl}(ethyl)amino]methyl}-3,3,3-trifluoro-2-hydroxypropyl)-1-(4-fluorophenyl)-1H-pyrazole-4-carboxamide |
| 28 | CH₂CH₂F | Cl | Cl | 5-amino-N-(2-{[[(2,6-dichlorophenyl)carbonyl](2-fluoroethyl)amino]methyl}-3,3,3-trifluoro-2-hydroxypropyl)-1-(4-fluorophenyl)-1H-pyrazole-4-carboxamide |
| 29 | CH₂CH₂F | Cl | F | 5-amino-N-(2-{[[(2-chloro-6-fluorophenyl)carbonyl](2-fluoroethyl)amino]methyl}-3,3,3-trifluoro-2-hydroxypropyl)-1-(4-fluorophenyl)-1H-pyrazole-4-carboxamide |
| 30 | CH₂CH₂F | Br | Cl | 5-amino-N-(2-{[[(2-bromo-6-chlorophenyl)carbonyl](2-fluoroethyl)amino]methyl}-3,3,3-trifluoro-2-hydroxypropyl)-1-(4-fluorophenyl)-1H-pyrazole-4-carboxamide |
| 31 | CH₂CH₂F | OCHF₂ | Cl | 5-amino-N-(2-{[({2-chloro-6-[(difluoromethyl)oxy]phenyl}carbonyl)(2-fluoroethyl)amino]methyl}-3,3,3-trifluoro-2-hydroxypropyl)-1-(4-fluorophenyl)-1H-pyrazole-4-carboxamide |
| 32 | CH₂CH₂F | OCHF₂ | OCHF₂ | 5-amino-N-(2-{[({2,6-bis[(difluoromethyl)oxy]phenyl}carbonyl)(2-fluoroethyl)amino]methyl}-3,3,3-trifluoro-2-hydroxypropyl)-1-(4-fluorophenyl)-1H-pyrazole-4-carboxamide |

The following Examples were similarly prepared to Example 6:

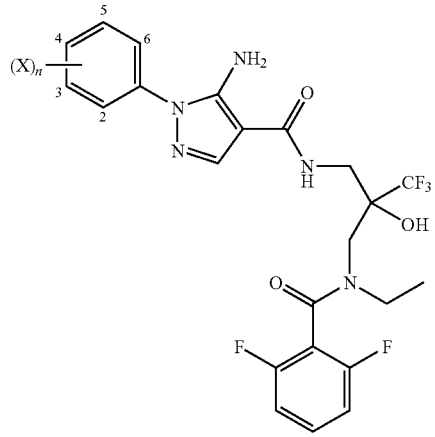

| Example Number | (X)ₙ | Compound Name |
|---|---|---|
| 33 | 3-F, 4-F | 5-amino-1-(3,4-difluorophenyl)-N-(2-{[[(2,6-difluorophenyl)carbonyl](ethyl)amino]methyl}-3,3,3-trifluoro-2-hydroxypropyl)-1H-pyrazole-4-carboxamide |
| 34 | 2-F, 4-F | 5-amino-1-(2,4-difluorophenyl)-N-(2-{[[(2,6-difluorophenyl)carbonyl](ethyl)amino]methyl}-3,3,3-trifluoro-2-hydroxypropyl)-1H-pyrazole-4-carboxamide |
| 35 | 3-F, 5-F | 5-amino-1-(3,5-difluorophenyl)-N-(2-{[[(2,6-difluorophenyl)carbonyl](ethyl)amino]methyl}-3,3,3-trifluoro-2-hydroxypropyl)-1H-pyrazole-4-carboxamide |
| 36 | 2-F, 5-F | 5-amino-1-(2,5-difluorophenyl)-N-(2-{[[(2,6-difluorophenyl)carbonyl](ethyl)amino]methyl}-3,3,3-trifluoro-2-hydroxypropyl)-1H-pyrazole-4-carboxamide |
| 37 | 2-F, 6-F | 5-amino-1-(2,6-difluorophenyl)-N-(2-{[[(2,6-difluorophenyl)carbonyl](ethyl)amino]methyl}-3,3,3-trifluoro-2-hydroxypropyl)-1H-pyrazole-4-carboxamide |
| 38 | 3-F | 5-amino-N-(2-{[[(2,6-difluorophenyl)carbonyl](ethyl)amino]methyl}-3,3,3-trifluoro-2-hydroxypropyl)-1-(3-fluorophenyl)-1H-pyrazole-4-carboxamide |
| 39 | 4-Cl | 5-amino-1-(4-chlorophenyl)-N-(2-{[[(2,6-difluorophenyl)carbonyl](ethyl)amino]methyl}-3,3,3-trifluoro-2-hydroxypropyl)-1H-pyrazole-4-carboxamide |
| 40 | 2-Cl | 5-amino-1-(2-chlorophenyl)-N-(2-{[[(2,6-difluorophenyl)carbonyl](ethyl)amino]methyl}-3,3,3-trifluoro-2-hydroxypropyl)-1H-pyrazole-4-carboxamide |
| 41 | 3-Cl | 5-amino-1-(3-chlorophenyl)-N-(2-{[[(2,6-difluorophenyl)carbonyl](ethyl)amino]methyl}-3,3,3-trifluoro-2-hydroxypropyl)-1H-pyrazole-4-carboxamide |
| 42 | 2-F | 5-amino-N-(2-{[[(2,6-difluorophenyl)carbonyl](ethyl)amino]methyl}-3,3,3-trifluoro-2-hydroxypropyl)-1-(2-fluorophenyl)-1H-pyrazole-4-carboxamide |

Example 43

5-Amino-N-{2-[({[2,6-bis(difluoromethyl)phenyl]carbonyl}amino)methyl]-3,3,3-trifluoro-2-hydroxypropyl}-1-(4-fluorophenyl)-1H-pyrazole-4-carboxamide

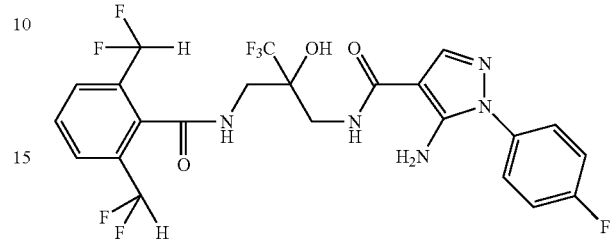

To a solution of 2,6-bis(difluoromethyl)benzoic acid (20 mg) in anhydrous tetrahydrofuran (0.8 ml) was added anhydrous dimethylformamide (5 μl) followed by oxalyl chloride (90 μl of a solution of oxalyl chloride (87 μl) in tetrahydrofuran (0.9 ml). It was left for 30 minutes and then 5-amino-N-[2-(aminomethyl)-3,3,3-trifluoro-2-hydroxypropyl]-1-(4-fluorophenyl)-1H-pyrazole-4-carboxamide (36 mg) and diisopropylethylamine (52 μl) were added. It was left at 21° C. for 17 hours, blown down, partitioned between dichloromethane (3 ml) and 2M hydrochloric acid (2 ml), washed with saturated brine (2 ml) and blown down to give (41.7 mg). This was purified on an SPE cartridge (SiO$_2$, 2 g) eluting with dichloromethane and then cyclohexane:ethyl acetate (4:1), (3:1), (2:1)(2×), (3:2)(3×) and finally (1:1)(2×).

The appropriate fractions were combined and evaporated to give the title compound (26.5 mg).

$^1$H NMR (400 MHz, MeOD) δ ppm 7.81-7.89 (m, 3H) 7.68-7.76 (m, 1H) 7.48-7.58 (m, 2H) 7.21-7.32 (m, 2H) 6.95 (t, 2H) 3.41-3.82 (m, 4H).

LC-MS Retention Time 1.08 mins, MH$^+$ 566.

Example 43 was further preparatively separated into its enantiomers (Isomers A and B) using a Chiralcel OD column eluting with 20% ethanol in heptane at a flow rate of 15 ml/min.

Enantiomer 1 (Isomer A)

Analytical Chiral HPLC (25×0.46 cm Chiralcel OD column, 25% ethanol in heptane eluting at 1 ml/min)—Retention time 5.26 mins.

Circular Dichroism (MeCN, RT, 0.000168M, v=350-200 nm, cell length=0.2 cm)

203 nm (de=3.10).

218 nm (de=−1.47).

262 nm (de=2.09).

Enantiomer 2 (Isomer B)

Analytical Chiral HPLC (25×0.46 cm Chiralcel OD column, 25% ethanol in heptane eluting at 1 ml/min)—Retention time 7.47 mins.

Circular Dichroism (MeCN, RT, 0.000166M, v=350-200 nm, cell length=0.2 cm)

202.4 nm (de=−2.20).

217 nm (de=1.68).

263 nm (de=−1.85).

Example 44

5-Amino-N-{2-[({[2-chloro-6-(trifluoromethyl)phenyl]carbonyl}amino)methyl]-3,3,3-trifluoro-2-hydroxypropyl}-1-(4-fluorophenyl)-1H-pyrazole-4-carboxamide

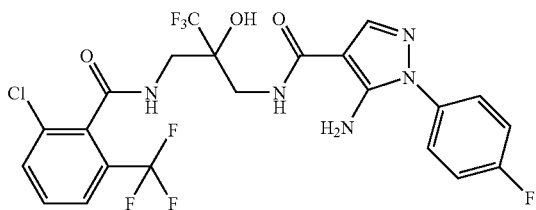

To a solution of 2-chloro-6-(trifluoromethyl)benzoic acid (27 mg) in anhydrous tetrahydrofuran (1 ml) was added anhydrous dimethylformamide (5 μl) followed by a solution of oxalyl chloride in anhydrous tetrahydrofuran (1M, 0.13 ml). The solution effervesced and was stirred under nitrogen for 30 minutes. A solution of 5-amino-N-[2-(aminomethyl)-3,3,3-trifluoro-2-hydroxypropyl]-1-(4-fluorophenyl)-1H-pyrazole-4-carboxamide (36 mg) in anhydrous tetrahydrofuran (1 ml) and diisopropylethylamine (65 μl) was added washed in with further tetrahydrofuran (0.5 ml). It was stirred under nitrogen for 16 hours, blown down, dissolved in dichloromethane (5 ml), washed with 2M hydrochloric acid (2 ml), blown down and purified on a silica SPE cartridge (5 g). Elution with dichloromethane followed by ethyl acetate:cyclohexane (1:5), (1:3), (1:2), (1:1) (4 times). Combination of the appropriate fractions and evaporation gave the title compound (50 mg).

$^1$H NMR (400 MHz, DMSO) ∂ ppm 9.02 (t, 1H), 8.03 (t, 1H), 7.91 (s, 1H), 7.87 (d, 1H), 7.79 (d, 1H), 7.67 (t, 1H), 7.57 (m, 2H), 7.36 (m, 2H), 6.65 (s, 1H), 6.35 (br. s., 2H), 3.75 (m, 2H), 3.52 (m, 2H).

LC/MS Retention Time 3.22 mins, MH$^+$ 568.

Example 44 was further preparatively separated into its enantiomers (Isomers A and B) using a Chiralpak AD column eluting with 40% propan-2-ol in heptane at a flow rate of 15 ml/min.

Enantiomer 1 (Isomer A)

Analytical Chiral HPLC (25×0.46 cm Chiralpak AD column, 40% propan-2-ol in heptane eluting at 1 ml/min)—Retention time 4.62 mins.

Enantiomer 2 (Isomer B)

Analytical Chiral HPLC (25×0.46 cm Chiralpak AD column, 40% propan-2-ol in heptane eluting at 1 ml/min)—Retention time 6.47 mins.

Example 45

5-Amino-N-{2-[({[2-bromo-6-(trifluoromethyl)phenyl]carbonyl}amino)methyl]-3,3,3-trifluoro-2-hydroxypropyl}-1-(4-fluorophenyl)-1H-pyrazole-4-carboxamide

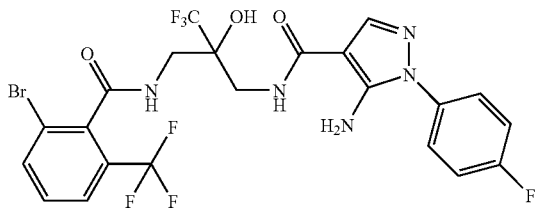

2-bromo-6-(trifluoromethyl)benzoic acid (70% pure, 60 mg) was dissolved in anhydrous tetrahydrofuran (2 ml). To this was added anhydrous dimethylformamide (5 μl) and 0.25 ml of a solution of oxalyl chloride (87 μl) in anhydrous tetrahydrofuran (0.9 ml). It was then stirred under nitrogen at 21° C. for 30 minutes and then a solution of 5-amino-N-[2-(aminomethyl)-3,3,3-trifluoro-2-hydroxypropyl]-1-(4-fluorophenyl)-1H-pyrazole-4-carboxamide (72 mg) in anhydrous tetrahydrofuran (2 ml) and diisopropylethylamine (130 μl) was added. It was stirred under nitrogen for 2 hours to give a suspension before being partitioned between ethyl acetate (20 ml) and 2M hydrochloric acid (10 ml), washed with water (10 ml) and saturated brine (10 ml), dried over MgSO$_4$ and evaporated to give a gum (128 mg). Purification of this gum via the Flashmaster 2 on SiO$_2$ (20 g) using 0-100% ethyl acetate in cyclohexane for 30 minutes gave the title compound (39.5 mg).

$^1$H NMR (400 MHz, CHLOROFORM-d) ∂ ppm 9.0 (t, 1H), 8.03 (m, 2H), 7.91 (s, 1H), 7.83 (d, 1H), 7.58 (m, 3H), 7.36 (m, 2H), 6.65 (s, 1H), 6.35 (br. s., 2H), 3.75 (m, 2H), 3.52 (m, 2H).

LC-MS Retention Time 3.32 mins, MH$^+$ 612, 614.

Example 45 was further preparatively separated into its enantiomers (Isomers A and B) using a Chiralpak AD column eluting with 40% propan-2-ol in heptane at a flow rate of 15 ml/min.

Enantiomer 1 (Isomer A)

Analytical Chiral HPLC (25×0.46 cm Chiralpak AD column, 40% propan-2-ol in heptane eluting at 1 ml/min)—Retention time 4.80 mins.

Enantiomer 2 (Isomer B)

Analytical Chiral HPLC (25×0.46 cm Chiralpak AD column, 40% propan-2-ol in heptane eluting at 1 ml/min)—Retention time 7.49 mins.

Example 48

5-Amino-N-(2-{[({2-[(difluoromethyl)oxy]-6-fluorophenyl}carbonyl)amino]methyl}-3,3,3-trifluoro-2-hydroxypropyl)-1-(4-fluorophenyl)-1H-pyrazole-4-carboxamide

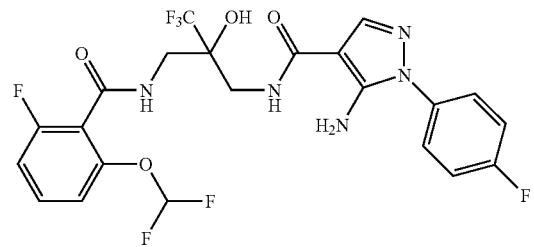

To a solution of 2-[(difluoromethyl)oxy]-6-fluorobenzoic acid (53.5 mg) in anhydrous tetrahydrofuran (2 ml) was added anhydrous dimethylformamide (5 μl) followed by oxalyl chloride (23 μl). It was stirred under nitrogen for 30 minutes and then 5-amino-N-[2-(aminomethyl)-3,3,3-trifluoro-2-hydroxypropyl]-1-(4-fluorophenyl)-1H-pyrazole-4-carboxamide (72 mg) and diisopropylethylamine (130 μl) were added. It was stirred for 23 hours and then partitioned between ethyl acetate (25 ml) and water (20 ml). It was washed with 2M hydrochloric acid (10 ml), water (10 ml), saturated sodium bicarbonate (10 ml), water (10 ml) and saturated brine (10 ml), dried over MgSO$_4$ and evaporated to give a gum (114 mg). This was purified on a SiO$_2$ cartridge (20 g) eluting with 0-100% ethyl acetate in dichloromethane over 20 minutes. Isolation of the appropriate fraction gave the title compound (65.3 mg).

$^1$H NMR (400 MHz, DMSO) δ ppm 8.92 (t, 1H), 8.02 (t, 1H), 7.91 (s, 1H), 7.56 (m, 3H), 7.36 (t, 2H), 7.24 (t, 1H, J=75 Hz), 7.21 (t, 1H), 7.12 (d, 1H), 6.62 (s, 1H), 6.35 (br. s., 2H), 3.76 (m, 2H), 3.45 (m, 2H).

LC-MS Retention Time 3.13 mins, MH$^+$ 550.

Example 48 was further preparatively separated into its enantiomers (Isomers A and B) using a Chiralcel OD column eluting with 20% ethanol in heptane at a flow rate of 15 ml/min.

Enantiomer 1 (Isomer A)

Analytical Chiral HPLC (25×0.46 cm Chiralcel OD column, 20% ethanol in heptane eluting at 1 ml/min)—Retention time 9.55 mins.

Enantiomer 2 (Isomer B)

Analytical Chiral HPLC (25×0.46 cm Chiralcel OD column, 20% ethanol in heptane eluting at 1 ml/min)—Retention time 12.81 mins.

Compounds which may also be prepared include:

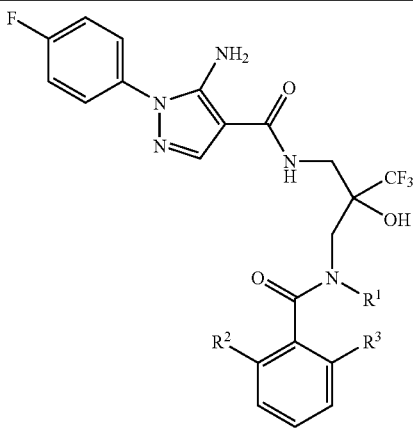

| Example Number | R$^1$ | R$^2$ | R$^3$ |
|---|---|---|---|
| 46 | H | CHF$_2$ | CF$_3$ |
| 47 | H | Br | OCHF$_2$ |

BIOLOGICAL EXAMPLES

Glucocorticoid Receptor Binding Assay

The ability of compounds to bind to the glucocorticoid receptor was determined by assessing their ability to compete with an Alexa 555 fluorescently-labelled dexamethasone derivative. Compounds were solvated and diluted in DMSO, and transferred directly into assay plates. Fluorescent dexamethasone and a partially purified full length glucocorticoid receptor were added to the plates, together with buffer components to stabilise the GR protein and incubated at room temperature for 2 hrs in the dark. Binding of each compound was assessed by analysing the displacement of fluorescent ligand by measuring the decrease in fluorescence polarisation signal from the mixture. Dose response curves were constructed from which pIC$_{50}$ values were estimated.

Example 1 (racemic), Example 1 Enantiomer 1, Example 1 Enantiomer 2, Example 2 (racemic), Example 2 Enantiomer 1, Example 2 Enantiomer 2, Example 3 (racemic), Example 3 Enantiomer 1, Example 3 Enantiomer 2, Example 4 (racemic), Example 4 Enantiomer 1, Example 4 Enantiomer 2, Example 5 (racemic), Example 5 Enantiomer 1, Example 5 Enantiomer 2, Example 7 (racemic), Example 8 (racemic), Example 9 (racemic), Example 10 (racemic), Example 10 Enantiomer 1, Example 11 (racemic), Example 11 Enantiomer 1, Example 11 Enantiomer 2, Example 12 (racemic), Example 12 Enantiomer 1, Example 12 Enantiomer 2, Example 13 (racemic), Example 13 Enantiomer 1, Example 13 Enantiomer 2, Example 14 (racemic), Example 14 Enantiomer 1, Example 14 Enantiomer 2, Example 15 (racemic), Example 15 Enantiomer 1, Example 15 Enantiomer 2, Example 16 (racemic), Example 17 (racemic), Example 18 (racemic), Example 19 (racemic), Example 19 Enantiomer 1, Example 19 Enantiomer 2, Example 20 (racemic), Example 21 (racemic), Example 22 (racemic), Example 23 (racemic), Example 24 (racemic), Example 25 (racemic), Example 26 (racemic), Example 27 (racemic), Example 28 (racemic), Example 29 (racemic), Example 30 (racemic), Example 31 (racemic), Example 32 (racemic), Example 33 (racemic), Example 34 (racemic), Example 35 (racemic), Example 36 (racemic), Example 37 (racemic), Example 38 (racemic), Example 39 (racemic), Example 40 (racemic), Example 41 (racemic), Example 42 (racemic), Example 43 (racemic), Example 43 Enantiomer 1, Example 44 (racemic), Example 44 Enantiomer 1, Example 44 Enantiomer 2, Example 45 (racemic), Example 45 Enantiomer 1, Example 45 Enantiomer 2, Example 48, Example 48 Enantiomer 1 and Example 48 Enantiomer 2 show glucocorticoid binding with a pIC$_{50}$≧6.5 in this assay.

Compounds possessing agonism in the NFkB assay, possessing reduced efficacy in the MMTV agonist assay and reduced activity at the progesterone receptor are believed to have the desired profile for providing anti-inflammatory activity with reduced side effect liability.

NFκB Assay

A549 SPAP Cells

Human caucasian lung carcinoma A549 cell line (ECACC No. 86012804) has been stably transfected in house with a plasmid containing an ELAM promoter sequence that has a NFκB response element within it. Stimulation of the cell line with TNFα results in intracellular signal transduction and ultimately translocation of NFκB into the nucleus. This activates the inserted DNA sequence resulting in transcription of the integrated SPAP gene, which is quantified using a colorimetric assay. In this assay, GR agonist compounds inhibit NFκB driven transcription resulting in a decrease in signal. The stably transfected cell line was grown as a monolayer in DMEM supplemented with FCS-HI (10%), Non-essential amino acids (1%), L-Glutamine (2 mM), Pen/Strep (1%) and Geneticin (50 mg/ml).

NFκB Agonist Assay

A 70% confluent T225 flask of A549 SPAP cells was harvested by centrifugation for 5 min at 200 g, resuspended in assay buffer (DMEM supplemented with 10% FCS 2×HI, 2 mM L-Glutamine, 1% Pen/Strep and Non essential amino acids) and diluted to 0.16×10$^6$/ml. 60 μl of cell solution was dispensed to each well of clear Nunc 384-well plates, containing compound at the required concentration. Plates were incubated for 1 h at 37° C., 95% humidity, 5% CO$_2$ before 10 μl of TNFα was added at final concentration of 3.2 ng/ml and then returned to the cell incubator for 15 h. Plates were equilibrated to room temperature for 1 h prior to the addition of 25 μl of pNPP buffer (1M Diethanolamine pH 9.8, 0.5 mM MgCl$_2$, 0.28M NaCl, 2 mg/ml pNPP) to each well of assay plates. The plates were covered to protect the reagents from light, and then incubated at room temperature for approximately 1 hour before reading them on an Ascent using a 405 nm single filter. Dose response curves were constructed from which $pIC_{50}$ values were estimated.

The $pIC_{50}$ values for Example 1 (racemic), Example 1 Enantiomer 1, Example 1 Enantiomer 2, Example 2 (racemic), Example 2 Enantiomer 1, Example 2 Enantiomer 2, Example 3 (racemic), Example 3 Enantiomer 1, Example 3 Enantiomer 2, Example 4 (racemic), Example 4 Enantiomer 1, Example 4 Enantiomer 2, Example 5 (racemic), Example 5 Enantiomer 1, Example 5 Enantiomer 2, Example 7 (racemic), Example 7 Enantiomer 1, Example 7 Enantiomer 2, Example 8 (racemic), Example 9 (racemic), Example 10 (racemic), Example 10 Enantiomer 1, Example 11 (racemic), Example 11 Enantiomer 1, Example 11 Enantiomer 2, Example 12 (racemic), Example 12 Enantiomer 1, Example 12 Enantiomer 2, Example 13 (racemic), Example 13 Enantiomer 1, Example 13 Enantiomer 2, Example 14 (racemic), Example 14 Enantiomer 1, Example 14 Enantiomer 2, Example 15 (racemic), Example 15 Enantiomer 2, Example 16 (racemic), Example 17 (racemic), Example 18 (racemic), Example 19 (racemic), Example 19 Enantiomer 1, Example 19 Enantiomer 2, Example 21 (racemic), Example 22 (racemic), Example 23 (racemic), Example 24 (racemic), Example 25 (racemic), Example 26 (racemic), Example 27 (racemic), Example 28 (racemic), Example 29 (racemic), Example 30 (racemic), Example 31 (racemic), Example 32 (racemic), Example 33 (racemic), Example 34 (racemic), Example 35 (racemic), Example 36 (racemic), Example 37 (racemic), Example 38 (racemic), Example 39 (racemic), Example 40 (racemic), Example 41 (racemic), Example 42 (racemic), Example 43 (racemic), Example 43 Enantiomer 1, Example 43 Enantiomer 2, Example 44 (racemic), Example 44 Enantiomer 1, Example 44 Enantiomer 2, Example 45 (racemic), Example 45 Enantiomer 1, Example 45 Enantiomer 2, Example 48 (racemic), Example 48 Enantiomer 1 and Example 48 Enantiomer 2 are >6 for the NFkB assay.

MMTV Assay
A549 MMTV Cells

Human caucasian lung carcinoma A549 cell line (ECACC No. 86012804) has been stably transfected in house with a plasmid containing a renilla luciferase reporter with an MMTV promoter. Stimulation of the cell line with GR agonists results in intracellular signal transduction and ultimately translocation of GR into the nucleus. This activates the inserted DNA sequence resulting in transcription of the integrated luciferase gene, which is quantified using a light emission. The stably transfected cell line was grown as a monolayer in DMEM supplemented with FCS-HI (10%), Non-essential amino acids (1%), L-Glutamine (2 mM), Pen/Strep (1%) and Geneticin (50 mg/ml).

MMTV Agonist Assay

A 90% confluent T175 flask of A549 MMTV cells was harvested by centrifugation for 5 min at 200 g, resuspended in assay buffer (DMEM supplemented with 10% FCS 2×HI, 2 mM Glutamax, Non essential amino acids and 25 mM HEPES) and diluted to $0.1 \times 10^6$/ml. 70 µl of cell solution was dispensed to each well of white Nunc 384-well plates, containing compound at the required concentration. Plates were incubated for 6 h at 37° C., 95% humidity, 5% $CO_2$. Plates were equilibrated to room temperature for 1 h prior to the addition of 10 µl of Renilla substrate to each well of assay plates. The plates were covered to protect the reagents from light, and then incubated at room temperature for approximately 15 mins before reading them on a Viewlux. Dose response curves were constructed from which $pEC_{50}$ and maximum asymptote values were estimated.

MMTV Antagonist Assay

A 90% confluent T175 flask of A549 MMTV cells was harvested by centrifugation for 5 min at 200 g, resuspended in assay buffer (DMEM supplemented with 10% FCS 2×HI, 2 mM Glutamax, Non essential amino acids and 25 mM HEPES) and diluted to $0.1 \times 10^6$1 ml. Dexamethasone was added to the cell solution to a concentration of 15 nM. From a 75 uM dexamethasone stock (DMSO solvent) 20 ul was added per 100 ml of assay media and cells. 70 µl of cell solution was dispensed to each well of white Nunc 384-well plates, containing compound at the required concentration. Plates were incubated for 24 h at 37° C., 95% humidity, 5% $CO_2$. Plates were equilibrated to room temperature for 1 h prior to the addition of 10 µl of Renilla substrate to each well of assay plates. The plates were covered to protect the reagents from light, and then incubated at room temperature for approximately 15 mins before reading them on a Viewlux. Dose response curves were constructed from which $pIC_{50}$ values were estimated.

The following examples are full agonists (i.e. have an average maximum asymptote of >85%) in the NFkB and MMTV agonist assays:
Example 1 (racemic), Example 1 Enantiomer 1, Example 2 (racemic), Example 2 Enantiomer 2, Example 4 (racemic), Example 4 Enantiomer 1, Example 5 (racemic), Example 5 Enantiomer 2, Example 8 (racemic), Example 9 (racemic), Example 10 (racemic), Example 10 Enantiomer 1, Example 16 (racemic), Example 17 (racemic), Example 18 (racemic), Example 21 (racemic), Example 22 (racemic), Example 23 (racemic), Example 24 (racemic), Example 25 (racemic), Example 26 (racemic), Example 27 (racemic), Example 28 (racemic), Example 29 (racemic), Example 30 (racemic), Example 31 (racemic), Example 33 (racemic), Example 34 (racemic), Example 35 (racemic), Example 36 (racemic), Example 37 (racemic), Example 38 (racemic), Example 39 (racemic), Example 40 (racemic), Example 41 (racemic) and Example 42 (racemic).

The following examples are partial or full agonists (i.e. have an average maximum asymptote of ≧20%) in the NFkB assay and are partial or efficacy selective agonists (i.e. have an average maximum asymptote of >20% and <85%) in the MMTV agonist assay: Example 1 Enantiomer 2, Example 2 Enantiomer 1, Example 3 (racemic), Example 3 Enantiomer 1, Example 3 Enantiomer 2, Example 4 Enantiomer 2, Example 5 Enantiomer 1, Example 7 (racemic), Example 7 Enantiomer 1, Example 7 Enantiomer 2, Example 11 (racemic), Example 11 Enantiomer 1, Example 11 Enantiomer 2, Example 12 (racemic), Example 12 Enantiomer 1, Example 12 Enantiomer 2, Example 13 (racemic), Example 13 Enantiomer 1, Example 13 Enantiomer 2, Example 14 (racemic), Example 14 Enantiomer 1, Example 14 Enantiomer 2, Example 15 (racemic), Example 15 Enantiomer 1, Example 15 Enantiomer 2, Example 19 (racemic), Example 19 Enantiomer 1, Example 19 Enantiomer 2, Example 43 (racemic), Example 43 Enantiomer 1, Example 44 (racemic), Example 44 Enantiomer 1, Example 44 Enantiomer 2, Example 45 (racemic), Example 45 Enantiomer 1, Example 45 Enantiomer 2, Example 48 Enantiomer 1 and Example 48 Enantiomer 2.

Assay for Progesterone Receptor Activity

A T225 flask of CV-1 cells at a density of 80% confluency was washed with PBS, detached from the flask using 0.25% trypsin and counted using a Sysmex KX-21N. Cells were diluted in DMEM containing 10% Hyclone, 2 mM L-Glutamate and 1% Pen/Strep at 140 cells/µl and transduced with 10% PRb-BacMam and 10% MMTV-BacMam. 70 ml of suspension cells were dispensed to each well of white Nunc 384-well plates, containing compounds at the required concentration. After 24 h 10 μl of Steadylite were added to each well of the plates. Plates were incubated in the dark for 10 min before reading them on a Viewlux reader. Dose response curves were constructed from which $pEC_{50}$ values were estimated.

Example 1 (racemic), Example 1 Enantiomer 1, Example 1 Enantiomer 2, Example 2 (racemic), Example 2 Enantiomer 1, Example 2 Enantiomer 2, Example 3 (racemic), Example 3 Enantiomer 1, Example 3 Enantiomer 2, Example 4 (racemic), Example 4 Enantiomer 1, Example 4 Enantiomer 2, Example 5 (racemic), Example 5 Enantiomer 1, Example 5 Enantiomer 2, Example 6 (racemic), Example 7 (racemic), Example 7 Enantiomer 1, Example 7 Enantiomer 2, Example 8 (racemic), Example 9 (racemic), Example 10 (racemic), Example 10 Enantiomer 1, Example 10 Enantiomer 2, Example 11 (racemic), Example 11 Enantiomer 1, Example 11 Enantiomer 2, Example 12 (racemic), Example 12 Enantiomer 1, Example 12 Enantiomer 2, Example 13 (racemic), Example 13 Enantiomer 1, Example 13 Enantiomer 2, Example 14 (racemic), Example 14 Enantiomer 1, Example 14 Enantiomer 2, Example 15 (racemic), Example 15 Enantiomer 1, Example 15 Enantiomer 2, Example 16 (racemic), Example 17 (racemic), Example 18 (racemic), Example 19 (racemic), Example 20 (racemic), Example 21 (racemic), Example 22 (racemic), Example 23 (racemic), Example 24 (racemic), Example 25 (racemic), Example 26 (racemic), Example 27 (racemic), Example 28 (racemic), Example 30 (racemic), Example 31 (racemic), Example 32 (racemic), Example 33 (racemic), Example 34 (racemic), Example 35 (racemic), Example 36 (racemic), Example 37 (racemic), Example 38 (racemic), Example 39 (racemic), Example 41 (racemic), Example 42 (racemic), Example 43 (racemic), Example 43 Enantiomer 1, Example 43 Enantiomer 2, Example 44 Enantiomer 1, Example 44 Enantiomer 2, Example 45 (racemic), Example 45 Enantiomer 1, Example 45 Enantiomer 2, Example 48 (racemic), Example 48 Enantiomer 1 and Example 48 Enantiomer 2 show $pEC_{50}$<6 in this assay.

Assay for Brain Penetrance

Each rat received a single intravenous dose at a level of 1 mg/kg. The dose was formulated in 10% DMSO/50% PEG200/40% sterile water. Terminal blood samples were taken at 5 or 15 minutes after dosing, by cardiac puncture following anaesthesia with isofluorane. The brains were removed at the same time point.

The compounds were extracted from 20 μL plasma by protein precipitation using 120 μL acetonitrile containing an analogue compound as an internal standard. The filtered extracts were collected into a 96 well plate and were diluted with an equal volume of 10% acetonitrile containing 0.1% formic acid in water (v/v). The plate was then mixed on a plate shaker for at least 5 minutes before analysis by LC-MS/MS against a calibration line prepared in control plasma.

Each brain was weighed, then homogenised in 3 ml acetonitrile:water (10:90 v/v). The compounds were extracted from 200 μL of the resulting homogenate by protein precipitation using 600 μL acetonitrile containing an analogue compound as an internal standard. The extracts were centrifuged and 150 μl of each was filtered and transferred to a 96 well plate. The aliquot was diluted with 10% acetonitrile containing 0.1% formic acid in water (v/v). The plate was mixed on a plate shaker for at least 5 minutes before analysis by LC-MS/MS against a calibration line prepared in control brain homogenate.

In this assay, Example 1 (Enantiomer 1), Example 5 (Enantiomer 1) and Example 5 (Enantiomer 2) have a brain to plasma ratio equal to or greater than 0.1 at 5 minutes.

In describing examples according to their activity in the assays above, it will be appreciated that at least one isomer, for example, an enantiomer in a mixture of isomers (such as a racemate) has the described activity. The other enantiomer may have similar activity, less activity, no activity or may have some antagonist activity in the case of a functional assay.

Throughout the specification and the claims which follow, unless the context requires otherwise, the word 'comprise', and variations such as 'comprises' and 'comprising', will be understood to imply the inclusion of a stated integer or step or group of integers but not to the exclusion of any other integer or step or group of integers or steps.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims.

The patents, patent applications and other references described in this application are herein incorporated by reference.

What is claimed is:

1. A compound of formula (I):

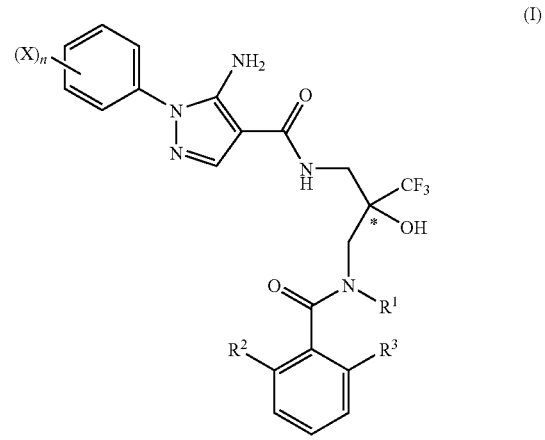

\* = chiral centre wherein
$R^1$ is hydrogen;
$R^2$ and $R^3$ are each independently selected from bromine, chlorine, fluorine, —$CHF_2$, —$CF_3$ and —$OCHF_2$, or $R^2$ is —$SO_2CH_3$ and $R^3$ is hydrogen;
n is an integer selected from 0, 1 and 2,
when n is 1, X is selected from chlorine and fluorine, and when n is 2, each X is fluorine;
or a salt thereof.

2. A compound according to claim 1 wherein $R^2$ and $R^3$ are each independently selected from the group consisting of fluorine, chlorine, bromine, —$OCHF_2$ and —$CHF_2$.

3. A compound according to claim 2 wherein $R^2$ and $R^3$ are each chlorine.

4. A compound according to claim 2 wherein $R^2$ and $R^3$ are each fluorine.

5. A compound according to claim 1 wherein n is 1.

6. A compound according to claim 5 wherein X is fluorine.

7. A compound of formula (IA):

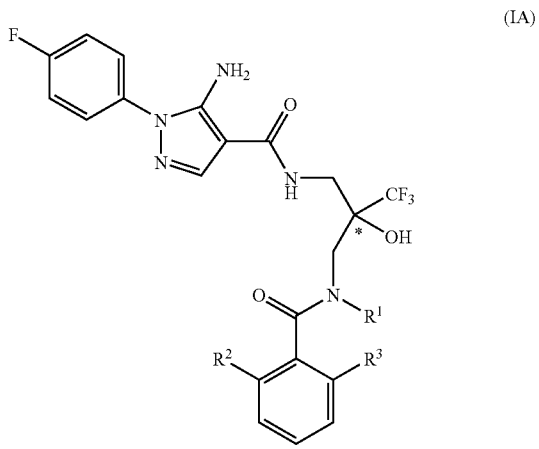

(IA)

* = chiral centre wherein
R$^1$ is selected from hydrogen, methyl and ethyl; and
when R$^1$ is hydrogen or methyl, R$^2$ and R$^3$ are each independently selected from chlorine and fluorine, or
when R$^1$ is ethyl, R$^2$ and R$^3$ are each independently selected from chlorine and fluorine, or R$^2$ is —SO$_2$CH$_3$ and R$^3$ is hydrogen;
or a salt thereof.

8. A compound selected from the group consisting of:
5-amino-N-[2-({[(2,6-dichlorophenyl)carbonyl]amino}methyl)-3,3,3-trifluoro-2-hydroxypropyl]-1-(4-fluorophenyl)-1H-pyrazole-4-carboxamide;
5-amino-N-[2-({[(2,6-dichlorophenyl)carbonyl]amino}methyl)-3,3,3-trifluoro-2-hydroxypropyl]-1-(4-fluorophenyl)-1H-pyrazole-4-carboxamide (Enantiomer 1);
5-amino-N-[2-({[(2,6-dichlorophenyl)carbonyl]amino}methyl)-3,3,3-trifluoro-2-hydroxypropyl]-1-(4-fluorophenyl)-1H-pyrazole-4-carboxamide (Enantiomer 2);
5-amino-N-(2-{[[(2,6-difluorophenyl)carbonyl](ethyl)amino]methyl}-3,3,3-trifluoro-2-hydroxypropyl)-1-(4-fluorophenyl)-1H-pyrazole-4-carboxamide;
5-amino-N-(2-{[[(2,6-difluorophenyl)carbonyl](ethyl)amino]methyl}-3,3,3-trifluoro-2-hydroxypropyl)-1-(4-fluorophenyl)-1H-pyrazole-4-carboxamide (Enantiomer 1);
5-amino-N-(2-{[[(2,6-difluorophenyl)carbonyl](ethyl)amino]methyl}-3,3,3-trifluoro-2-hydroxypropyl)-1-(4-fluorophenyl)-1H-pyrazole-4-carboxamide (Enantiomer 2);
5-amino-N-[2-({[(2-chloro-6-fluorophenyl)carbonyl]amino}methyl)-3,3,3-trifluoro-2-hydroxypropyl]-1-(4-fluorophenyl)-1H-pyrazole-4-carboxamide;
5-amino-N-[2-({[(2-chloro-6-fluorophenyl)carbonyl]amino}methyl)-3,3,3-trifluoro-2-hydroxypropyl]-1-(4-fluorophenyl)-1H-pyrazole-4-carboxamide (Enantiomer 1);
5-amino-N-[2-({[(2-chloro-6-fluorophenyl)carbonyl]amino}methyl)-3,3,3-trifluoro-2-hydroxypropyl]-1-(4-fluorophenyl)-1H-pyrazole-4-carboxamide (Enantiomer 2);
5-amino-N-[2-({[(2-bromo-6-fluorophenyl)carbonyl]amino}methyl)-3,3,3-trifluoro-2-hydroxypropyl]-1-(4-fluorophenyl)-1H-pyrazole-4-carboxamide;
5-amino-N-[2-({[(2-bromo-6-fluorophenyl)carbonyl]amino}methyl)-3,3,3-trifluoro-2-hydroxypropyl]-1-(4-fluorophenyl)-1H-pyrazole-4-carboxamide (Enantiomer 1);
5-amino-N-[2-({[(2-bromo-6-fluorophenyl)carbonyl]amino}methyl)-3,3,3-trifluoro-2-hydroxypropyl]-1-(4-fluorophenyl)-1H-pyrazole-4-carboxamide (Enantiomer 2);
5-amino-N-(2-{[({2-chloro-6-[(difluoromethyl)oxy]phenyl}carbonyl)amino]methyl}-3,3,3-trifluoro-2-hydroxypropyl)-1-(4-fluorophenyl)-1H-pyrazole-4-carboxamide;
5-amino-N-(2-{[({2-chloro-6-[(difluoromethyl)oxy]phenyl}carbonyl)amino]methyl}-3,3,3-trifluoro-2-hydroxypropyl)-1-(4-fluorophenyl)-1H-pyrazole-4-carboxamide (Enantiomer 1);
5-amino-N-(2-{[({2-chloro-6-[(difluoromethyl)oxy]phenyl}carbonyl)amino]methyl}-3,3,3-trifluoro-2-hydroxypropyl)-1-(4-fluorophenyl)-1H-pyrazole-4-carboxamide (Enantiomer 2);
5-amino-N-{2-[({[2,6-bis(difluoromethyl)phenyl]carbonyl}amino)methyl]-3,3,3-trifluoro-2-hydroxypropyl}-1-(4-fluorophenyl)-1H-pyrazole-4-carboxamide;
5-amino-N-{2-[({[2,6-bis(difluoromethyl)phenyl]carbonyl}amino)methyl]-3,3,3-trifluoro-2-hydroxypropyl}-1-(4-fluorophenyl)-1H-pyrazole-4-carboxamide (Enantiomer 1);
5-amino-N-{2-[({[2,6-bis(difluoromethyl)phenyl]carbonyl}amino)methyl]-3,3,3-trifluoro-2-hydroxypropyl}-1-(4-fluorophenyl)-1H-pyrazole-4-carboxamide (Enantiomer 2);
5-amino-N-(2-{[({2-[(difluoromethyl)oxy]-6-fluorophenyl}carbonyl)amino]methyl}-3,3,3-trifluoro-2-hydroxypropyl)-1-(4-fluorophenyl)-1H-pyrazole-4-carboxamide;
5-amino-N-(2-{[({2-[(difluoromethyl)oxy]-6-fluorophenyl}carbonyl)amino]methyl}-3,3,3-trifluoro-2-hydroxypropyl)-1-(4-fluorophenyl)-1H-pyrazole-4-carboxamide (Enantiomer 1);
5-amino-N-(2-{[({2-[(difluoromethyl)oxy]-6-fluorophenyl}carbonyl)amino]methyl}-3,3,3-trifluoro-2-hydroxypropyl)-1-(4-fluorophenyl)-1H-pyrazole-4-carboxamide (Enantiomer 2);
or a salt thereof.

9. A compound which is:
5-amino-N-[2-({[(2,6-dichlorophenyl)carbonyl]amino}methyl)-3,3,3-trifluoro-2-hydroxypropyl]-1-(4-fluorophenyl)-1H-pyrazole-4-carboxamide (Enantiomer 2); or
a salt thereof.

10. A compound which is:
5-amino-N-(2-{[[(2,6-difluorophenyl)carbonyl](ethyl)amino]methyl}-3,3,3-trifluoro-2-hydroxypropyl)-1-(4-fluorophenyl)-1H-pyrazole-4-carboxamide (Enantiomer 2); or
a salt thereof.

11. A pharmaceutical composition comprising a compound of formula (I) as claimed claim 1, or a pharmaceutically acceptable salt thereof, in admixture with one or more pharmaceutically acceptable diluents or carriers.

12. A compound according to claim 9 which is:
5-amino-N-[2-({[(2,6-dichlorophenyl)carbonyl]amino}methyl)-3,3,3-trifluoro-2-hydroxypropyl]-1-(4-fluorophenyl)-1H-pyrazole-4-carboxamide (Enantiomer 2); or
a pharmaceutically acceptable salt thereof.

13. A compound according to claim 12 which is:
5-amino-N-[2-({[(2,6-dichlorophenyl)carbonyl]amino}methyl)-3,3,3-trifluoro-2-hydroxypropyl]-1-(4-fluorophenyl)-1H-pyrazole-4-carboxamide (Enantiomer 2); or
a pharmaceutically acceptable salt.

14. A compound according to claim 12 which is:
5-amino-N-[2-({[(2,6-dichlorophenyl)carbonyl]amino}methyl)-3,3,3-trifluoro-2-hydroxypropyl]-1-(4-fluorophenyl)-1H-pyrazole-4-carboxamide (Enantiomer 2) as the free base.

15. A pharmaceutical composition according to claim 11 in the form of eye drops for topical administration.

16. A pharmaceutical composition comprising a compound of formula (I) as claimed in claim 12, or a pharmaceutically acceptable salt thereof, in admixture with one or more pharmaceutically acceptable diluents or carriers.

17. A pharmaceutical composition according to claim 16 in the form of eye drops for topical administration.

18. A pharmaceutical composition comprising a compound of formula (I) as claimed in claim 13, or a pharmaceutically acceptable salt thereof, in admixture with one or more pharmaceutically acceptable diluents or carriers.

19. A pharmaceutical composition according to claim 18 in the form of eye drops for topical administration.

20. A pharmaceutical composition comprising a compound of formula (I) as claimed in claim 14, or a pharmaceutically acceptable salt thereof, in admixture with one or more pharmaceutically acceptable diluents or carriers.

21. A pharmaceutical composition according to claim 20 in the form of eye drops for topical administration.

* * * * *